(12) United States Patent
Wengreen et al.

(10) Patent No.: US 9,707,156 B2
(45) Date of Patent: Jul. 18, 2017

(54) STORAGE SYSTEMS AND METHODS FOR MEDICINES

(71) Applicants: Sandy Wengreen, Sammamish, WA (US); Eric John Wengreen, Sammamish, WA (US)

(72) Inventors: Sandy Wengreen, Sammamish, WA (US); Eric John Wengreen, Sammamish, WA (US)

( * ) Notice: Subject to any disclaimer, the term of this patent is extended or adjusted under 35 U.S.C. 154(b) by 161 days.

(21) Appl. No.: 14/849,884

(22) Filed: Sep. 10, 2015

(65) Prior Publication Data

US 2016/0228328 A1    Aug. 11, 2016

Related U.S. Application Data

(63) Continuation-in-part of application No. 14/616,652, filed on Feb. 6, 2015, now Pat. No. 9,151,531.

(51) Int. Cl.
| | |
|---|---|
| F25D 25/00 | (2006.01) |
| A61J 1/16 | (2006.01) |
| B65B 63/08 | (2006.01) |
| A61M 5/00 | (2006.01) |
| A61J 1/18 | (2006.01) |
| B65D 81/38 | (2006.01) |
| F25D 3/00 | (2006.01) |
| F25D 3/08 | (2006.01) |

(Continued)

(52) U.S. Cl.
CPC .............. *A61J 1/165* (2013.01); *A61J 1/1412* (2013.01); *A61J 1/18* (2013.01); *A61M 5/002* (2013.01); *B65B 63/08* (2013.01); *B65D 81/383* (2013.01); *F25D 3/00* (2013.01); *F25D 3/08* (2013.01); *A61J 1/1418* (2015.05); *A61J 2200/40* (2013.01); *A61J 2200/50* (2013.01); *A61J 2200/72* (2013.01); *A61J 2205/70* (2013.01); *A61M 2005/3125* (2013.01); *A61M 2205/127* (2013.01); *A61M 2205/3368* (2013.01); *A61M 2205/3633* (2013.01); *A61M 2205/8206* (2013.01); *F25D 2303/085* (2013.01); *F25D 2303/0843* (2013.01); *F25D 2303/08222* (2013.01)

(58) Field of Classification Search
CPC . F25D 3/10; F25D 17/065; F25D 3/08; F25D 2331/804
USPC ........... 62/62, 419, 457.2, 457.5; 165/104.17
See application file for complete search history.

(56) References Cited

U.S. PATENT DOCUMENTS

| | | |
|---|---|---|
| 2,263,865 A | 11/1941 | Lewis |
| 3,034,845 A | 5/1962 | Haumann |
| 3,401,692 A | 9/1968 | Harris |

(Continued)

OTHER PUBLICATIONS

Ball Article: "How Beverage Cans are Made," downloaded Apr. 21, 2016 from www.ball-europe.com/Production-process-of-beverage-cans.htm.
PureTemp Article: "PCM Products," includes Vesl products, downloaded Apr. 21, 2016 from www.puretemp.com/stories/products.
Vesl: "TubeVesl," downloaded Apr. 21, 2016 from www.veslpcm.com/tubevesl/.
Vesl: "MatVesl," downloaded Apr. 21, 2016 from www.veslpcm.com/matvesl/.

(Continued)

*Primary Examiner* — Melvin Jones

(57) ABSTRACT

People can damage their medicines by taking them outside in hot or cold weather. On the other hand, some people need to carry their medicines with them wherever they go (even if the weather is extremely hot or cold). Specially constructed storage systems can protect medicines from damage due to hot and cold weather without requiring bulky structures or expensive components that consume electricity to regulate temperature.

19 Claims, 34 Drawing Sheets

(51) Int. Cl.
  *A61M 5/31* (2006.01)
  *A61J 1/14* (2006.01)

(56) References Cited

U.S. PATENT DOCUMENTS

| | | | |
|---|---|---|---|
| 3,872,864 A | | 3/1975 | Allen |
| 3,910,441 A | | 10/1975 | Bramming |
| 3,961,720 A | | 6/1976 | Potter |
| 4,287,943 A | | 9/1981 | Hotta |
| 4,323,066 A | | 4/1982 | Bourdon |
| 4,738,364 A | | 4/1988 | Yeager |
| 5,317,883 A | * | 6/1994 | Newman .................. F25D 17/06 62/419 |
| 5,330,810 A | | 7/1994 | Nishino |
| 5,390,791 A | | 2/1995 | Yeager |
| 5,531,255 A | | 7/1996 | Vacca |
| 5,615,772 A | | 4/1997 | Naganuma |
| 5,976,400 A | | 11/1999 | Muffett |
| 6,104,611 A | | 8/2000 | Glover |
| 6,336,340 B1 | | 1/2002 | Laby |
| 6,584,797 B1 | | 7/2003 | Smith |
| 6,634,417 B1 | | 10/2003 | Kolowich |
| 6,968,888 B2 | | 11/2005 | Kolowich |
| 7,041,123 B2 | | 5/2006 | Stapf |
| 7,059,387 B2 | | 6/2006 | Kolowich |
| 7,294,374 B2 | | 11/2007 | Romero |
| 7,328,583 B2 | | 2/2008 | Hillman |
| 7,412,846 B2 | | 8/2008 | Sekiya |
| 7,836,722 B2 | | 11/2010 | Magill |
| 7,908,870 B2 | | 3/2011 | Williams |
| 7,934,537 B2 | | 5/2011 | Kolowich |
| 8,096,975 B2 | | 1/2012 | Lewis |
| 8,205,468 B2 | | 6/2012 | Hemminger |
| 8,225,616 B2 | | 7/2012 | Wilkinson |
| 8,550,703 B2 | * | 10/2013 | Cutting .................. G01N 29/07 374/117 |
| 8,607,581 B2 | | 12/2013 | Williams |
| 9,151,531 B2 | | 10/2015 | Wengreen |
| 9,181,015 B2 | | 11/2015 | Booska |
| 2003/0012701 A1 | | 1/2003 | Sangha |
| 2005/0016895 A1 | | 1/2005 | Glenn |
| 2005/0188714 A1 | | 9/2005 | Wallace |
| 2006/0191282 A1 | | 8/2006 | Sekiya |
| 2006/0271014 A1 | | 11/2006 | Hynes |
| 2007/0000484 A1 | | 1/2007 | Magill |
| 2007/0017533 A1 | | 1/2007 | Wyrick |
| 2007/0158325 A1 | | 7/2007 | Cao |
| 2007/0210090 A1 | | 9/2007 | Sixt |
| 2009/0078708 A1 | | 3/2009 | Williams |
| 2009/0230138 A1 | | 9/2009 | Williams |
| 2011/0155621 A1 | | 6/2011 | Lindquist et al. |
| 2011/0207824 A1 | | 8/2011 | Douleau |
| 2012/0073312 A1 | * | 3/2012 | Cutting .................. G01N 29/07 62/62 |
| 2013/0025298 A1 | * | 1/2013 | Schryver ............. A01N 1/0263 62/62 |
| 2013/0134347 A1 | | 5/2013 | Edgar |
| 2013/0221013 A1 | | 8/2013 | Kolowich |
| 2013/0255824 A1 | | 10/2013 | Williams |
| 2014/0259912 A1 | | 9/2014 | Sutterlin |
| 2015/0151893 A1 | | 6/2015 | Wengreen |

OTHER PUBLICATIONS

Kool Blanket: Downloaded Jun. 3, 2016 from www.allergyapparel.com/kool-blanket.
Frio Case: Downloaded Jun. 3, 2016 from www.frioinsulincoolingcase.com/media/FRIO%20Brochure.pdf.
Wikipedia Article: "Phase Change Material," downloaded Feb. 5, 2015 from http://en.wikipedia.org/wiki/Phase-change_material.
PureTemp: "About Entropy Solutions, Inc.," downloaded Feb. 5, 2015 from http://www.puretemp.com/stories/about-entropy-solutions-inc.
Fastcoexist.com Listing: "Passive Vaccine Storage Device," downloaded Aug. 15, 2013 from http://www.fastcoexist.com/1682578/this-bill-gates-backed-super-thermos-saves-lives-with-cold-vaccines.
Howstuffworks.com Article: "How Thermoses (Vacuum Flasks) Work," downloaded Jun. 14, 2013 from http://home.howstuffworks.com/thermos2.htm.
Wikipedia Article: "Epinephrine Autoinjector," downloaded Jun. 14, 2013 from http://en.wikipedia.org/wiki/Epinephrine_autoinjector.
Aliexpress.com Listing: "Retail Medicine Storage Product Mini EpiPen Fridge," downloaded Jun. 14, 2013 from http://www.aliexpress.com/item/Retail-medicine-storage-product-mini-epipen-fridge-maintains-the-inside-temperature-at-2-8-degreeC-CE/827311928.html.
Aliexpress.com Listing: "Pharmacy Product JYK-A Portable EpiPen Fridge," downloaded Jun. 14, 2013 from http://www.aliexpress.com/item/Pharmacy-product-JYK-A-Portable-epipen-fridge-AC-DC-Ii-battery-comes-with-16-5hrs-leading/723856846.html.
Amazon.com Listing: "Epinephrine-Mate Auto-Injector Carrying Case," downloaded Jun. 14, 2013 from http://www.amazon.com/EPInephrine-Mate-Auto-Injector-Carrying-Case/dp/B000VM9HGK.
Lindongroup.com Graphic: "Epinephrine-Mate Auto-Injector Carrying Case," downloaded Jun. 14, 2013 from http://www.lindongroup.com/uploads/images/Lindon%20Design/epinephrinemate%20package.jpg.
Omaxcare.com Listing: "LegBuddy," downloaded Jun. 14, 2013 from http://omaxcare.com/LegBuddy.html.
Amazon.com Listing: "AllerMates EpiPen & Allergy Medicine Carrying Case," downloaded Jun. 14, 2013 from http://www.amazon.com/AllerMates-Allergy-Medicine-Carrying-Squares/dp/B00CBLWMRA.
Esty.com Listing: "EpiPen Case Pouch," downloaded Jun. 14, 2013 from http://www.esty.com/listing/81915096/epi-pen-pouch-carrior-insulated.
Allergyapparel.com Listing: "AllerMates EpiPen Carrying Case," downloaded Jun. 17, 2014 from http://www.allergyapparelcom/AllerMates-EpiPen-Carrying-Case-allermates-epicase-blu-pnk.html.
EpiPen.com: "EpiPen.com FAQ," downloaded Jun. 14, 2013 from http://www.epipen.com/professionals/faq.

\* cited by examiner

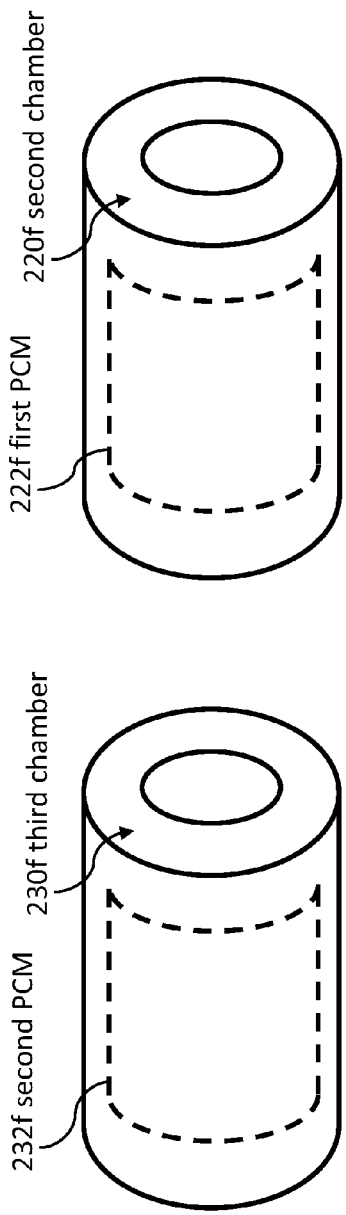
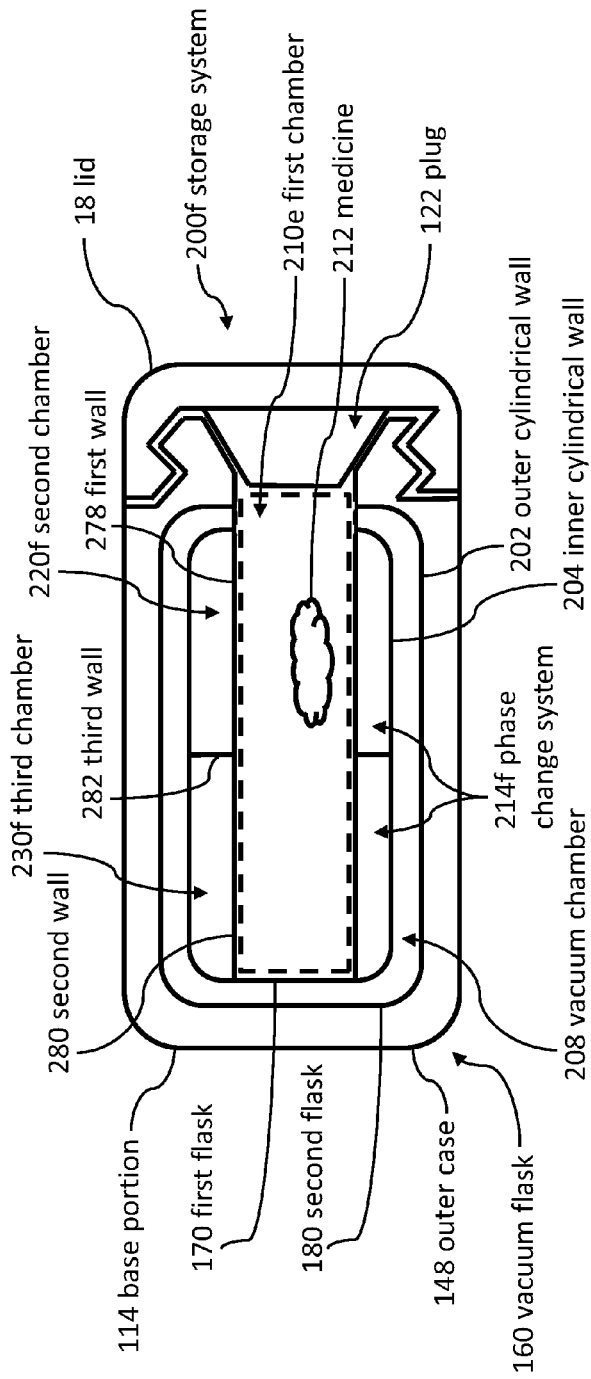
Figure 26
Figure 27
Figure 28

STORAGE SYSTEMS AND METHODS FOR MEDICINES

CROSS-REFERENCE TO RELATED APPLICATIONS

This application claims the benefit of and is a continuation-in-part of U.S. Nonprovisional patent application Ser. No. 14/616,652; filed Feb. 6, 2015; and entitled STORAGE SYSTEMS AND METHODS FOR MEDICINES. The entire contents of patent application Ser. No. 14/616,652 are incorporated by reference herein.

U.S. Nonprovisional patent application Ser. No. 14/616,652 claims the benefit of and is a continuation-in-part of U.S. Nonprovisional patent application Ser. No. 13/896,211; filed May 16, 2013; and entitled STORAGE SYSTEMS AND STORAGE METHODS FOR INJECTABLE SUBSTANCES. The entire contents of patent application Ser. No. 13/896,211 are incorporated by reference herein.

BACKGROUND

Field

Various embodiments disclosed herein relate to systems and methods to store medicines. Certain embodiments relate to maintaining medicines at a suitable temperature.

Description of Related Art

Users of medicines, such as epinephrine, adrenaline, and insulin, are faced with a difficult challenge. On one hand, physicians often advise patients to take their medicines with them wherever they go. Yet on the other hand, the temperature of many medicines typically should be maintained within a temperature range that is incompatible with outdoor temperatures. For example, a certain injectable substance might need to be stored within a temperature range of 65 degrees Fahrenheit to 85 degrees Fahrenheit. Outdoor temperatures are often colder than 65 degrees Fahrenheit or warmer than 85 degrees Fahrenheit. As a result, patients who need injectable substances sometimes must remain indoors, risk going outdoors without the safety of carrying the injectable substance, or risk reducing the efficacy of the injectable substance by carrying it into environments with temperatures outside of the recommended range.

Prior art solutions have included refrigerators set to particular temperatures to store medicines within a suitable range. (The suitable range can be the storage range recommended by the manufacturer of the medicine.) Refrigerators require substantial electrical power. Constantly having to plug a refrigerator into a power supply, changing batteries, or recharging batteries is inconvenient. In addition, users sometimes forget to provide adequate power, which can result in harming the medicine, and thereby, creating a health risk to the user. Thus, there is a need for systems and methods to store injectable substances within a suitable temperature range while requiring little or no electrical power.

Prior art solutions have also included bulky insulation systems that are inconvenient for patients to carry outside. Due to this inconvenience, many patients do not carry vital medicines when they go outside. As a result, many patients have suffered medical emergencies and some patients have died. Thus, there is a need for systems and methods that are convenient enough for patients to carry their medicines outdoors.

SUMMARY

In some embodiments, devices to store medicines can include a chamber configured to store a medicine, a thermal bank, and an insulated cover. The thermal bank can be located inside the insulated cover. At least a portion of the chamber can be located inside the thermal bank. The thermal bank can include phase change materials. Storage devices can also include innovative structures that dramatically reduce the volume and weight of the storage devices while still shielding medicines from extreme outdoor environments.

In some embodiments, devices to store injectable substances can include an outer case and a vacuum flask located inside the outer case. The devices can include a thermal bank located inside the vacuum flask. The thermal bank can include a void that extends from an inner portion of the thermal bank to an outer portion of the thermal bank. An injectable substance can be located inside the void. The devices can include a removable lid configured to allow a user to remove the injectable substance from the storage system. In some embodiments, a user unthreads or rotates the lid to remove the lid. In several embodiments, insulated containers use foam insulation, materials that capture small air pockets, or other suitable insulation rather than a vacuum flask (e.g., a Thermos).

Several embodiments include methods of storing injectable substances, inhalers, pharmaceuticals, or drugs. Some method embodiments comprise obtaining an outer case and a lid. Several methods include placing a vacuum flask inside the outer case and placing a thermal bank inside the vacuum flask. Some methods include placing an injectable substance inside the vacuum flask and closing the lid such that the outer case and the lid completely surround the injectable substance.

Some embodiments include a storage system comprising a chamber configured to store an injection device; a thermal bank; and/or an insulated cover. The thermal bank can have a heat capacity of at least 1,200 J/K. The thermal bank can be located inside the insulated cover. At least a portion of the chamber can be located inside the thermal bank. The injection device can be located inside the chamber. The injection device can comprise a syringe and a pharmaceutical agent located inside the syringe. The pharmaceutical agent can comprise epinephrine.

In some embodiments, the thermal bank comprises a hole that extends to an outer surface of the thermal bank and at least a portion of the chamber is located in the hole. The chamber can have a volume, and at least 60% of the volume of the chamber can be located inside the thermal bank.

In several embodiments, the storage system has a central axis, and the chamber is located approximately along a portion the central axis. A portion of the thermal bank can be located radially outward relative to the chamber. A portion of the insulated cover can be located radially outward relative to the thermal bank. The thermal bank can be removably coupled to the insulated cover. The thermal bank can be rigidly coupled to the insulated cover. The thermal bank can comprise a container with solid outer walls. The container can be at least partially filled with a liquid having a melting temperature between 40 degrees Fahrenheit and 100 degrees Fahrenheit.

In some embodiments, the storage system includes an outer case; a vacuum flask located inside the outer case; and/or a thermal bank located inside the vacuum flask. The thermal bank can include a heat capacity of at least 400 J/K. The thermal bank can also include a void that extends from an inner portion of the thermal bank to an outer portion of the thermal bank. The void can be at least 1 centimeter wide and at least 6 centimeters long. An injectable substance can be located inside the void. A removable lid can be configured to allow a user to remove the injectable substance from the storage system. The storage system can have a volumetric center. The volumetric center can be located inside the void. The heat capacity of the thermal bank can be at least 2,000 J/K and/or less than 12,000 J/K.

Several embodiments of storing a medicinal injectable substance include obtaining an outer case and a lid; obtaining a vacuum flask located inside the outer case; obtaining a thermal bank with a heat capacity of at least 400 J/K, wherein the thermal bank can be located inside the vacuum flask; placing an injection device inside the vacuum flask, wherein the injection device is at least partially filled with the medicinal injectable substance; and/or coupling the lid to the outer case such that the outer case and the lid surround the injection device. The injection device can include a syringe at least partially filled with epinephrine.

Some embodiments include placing the injection device inside at least a portion of the thermal bank. Embodiments can include forming the outer case around at least a portion of the vacuum flask. Several embodiments include maintaining the injectable substance within a temperature range of at least 50 degrees Fahrenheit and less than 90 degrees Fahrenheit. Inside environments can have a "room temperature" (e.g., a temperature within a typical range for a temperature-controlled home in the United States). Some embodiments include isolating the injectable substance from fluids located outside of the injection device.

Several embodiments include placing the thermal bank in a first environment, wherein the first environment has a temperature greater than 65 degrees Fahrenheit and less than 85 degrees Fahrenheit; removing the thermal bank from the first environment and transporting the thermal bank towards a second environment while the thermal bank has a temperature greater than 65 degrees Fahrenheit and less than 85 degrees Fahrenheit, wherein the second environment has a temperature less than 65 degrees Fahrenheit or greater than 85 degrees Fahrenheit; and/or moving the thermal bank from the second environment to a third environment before the temperature of the thermal bank falls below 65 degrees Fahrenheit or rises above 85 degrees Fahrenheit, wherein the third environment has a temperature greater than 65 degrees Fahrenheit and less than 85 degrees Fahrenheit. The first environment can be indoors. The second environment can be outdoors. The third environment can be indoors (e.g., at a room temperature). Some embodiments do not comprise using electricity to alter the temperature of the thermal bank while the thermal bank is located in the second environment and while the heat capacity of the thermal bank is at least 800 J/K. Embodiments can use electricity to measure temperatures even if they do not use electricity to alter the temperature.

In several embodiments, storage systems include an insulated container comprising a base and an opening configurable to enable removing a medicine from inside the insulated container; a first chamber located inside the insulated container, wherein the first chamber is configured to hold the medicine; a first phase change material located inside the insulated container; and/or a second phase change material located inside the insulated container.

In some embodiments, the first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. The first melting temperature can be at least four degrees Fahrenheit less than the second melting temperature. For example, 74 degrees Fahrenheit can be approximately equal to a typical room temperature (although room temperatures commonly range from 67 degrees Fahrenheit to 80 degrees Fahrenheit in rooms having temperature controlled environments enabled by heating and/or air conditioning).

Using a "temperature dividing line" of 74 degrees Fahrenheit helps enable some embodiments to avoid inappropriately triggering melting and/or freezing while the storage system is located in a temperature controlled room. Imagine if the second phase change material had a melting temperature of less than 74 degrees. As a result, the second phase change material could completely melt before a person even moved the storage system from a room temperature into a hot outdoor environment that is warmer than a maximum recommended storage temperature of the medicine. In this case, the phase change of the second phase change material would not help reduce the rate of temperature rise inside the first chamber in response to heat transfer caused by the hot environment. Similarly, this "temperature dividing line" helps ensure the first phase change material will have a sufficiently low melting temperature such that the first phase change material should not solidify before the storage system is moved from a room temperature to an environment that is colder than a minimum recommended storage temperature.

In some embodiments, the first phase change material can have a first melting temperature greater than 63 degrees Fahrenheit and less than 74 degrees Fahrenheit. The second phase change material can have a second melting temperature greater than 74 degrees Fahrenheit and less than 83 degrees Fahrenheit. These melting temperatures can be particularly effective to create a system that quickly responds (e.g., by changing phases) to temperature changes caused by leaving an indoor environment and entering an outdoor environment. Meridian Medical Technologies, Inc. makes a medicine called an EpiPen. EpiPens can have a minimum recommended storage temperature of 68 degrees Fahrenheit and a maximum recommended storage temperature of 77 degrees Fahrenheit. Other medicines often have different minimum and maximum recommended storage temperatures.

In some embodiments, the storage system is configured to cause the first phase change material to solidify when a first temperature of the first chamber falls below the first melting temperature, and/or the storage system is configured to cause the second phase change material to melt when the first temperature of the first chamber rises above the second melting temperature. As a result, the storage system can be configured to temporarily protect the medicine from a first environment that is colder than a safe minimum storage temperature and/or from a second environment that is hotter than a safe maximum storage temperature. Manufacturers of medicines can recommend minimum storage temperatures and/or maximum storage temperatures for medicines.

In several embodiments, the first phase change material has a first latent heat of at least 40 kJ/kg, and/or the second phase change material has a second latent heat of at least 40 kJ/kg. (The latent heats described herein are latent heats of fusion.) In some embodiments, the first phase change material has a first latent heat of at least 110 kJ/kg, and/or the second phase change material has a second latent heat of at least 110 kJ/kg. In several embodiments, the first phase change material has a first latent heat of at least 180 kJ/kg, and/or the second phase change material has a second latent heat of at least 180 kJ/kg. These latent heat properties can dramatically reduce the necessary weight of the phase change materials, which can enable dramatically reducing the overall volume of the storage system.

In some embodiments, a storage system comprises a second chamber having the first phase change material, and/or the insulated container comprises a third chamber having the second phase change material. The second chamber and the third chamber can be located inside the insulated container. The opening can be coupled to the first chamber such that the opening is configurable to provide access to the first chamber to enable removing the medicine from the insulated container.

In some embodiments, the insulated container is a flexible bag with a foil coating to reduce the rate of heat transfer in and out of the bag. The bag can have a fabric exterior. The chambers can be pliable bags. In some embodiments, the insulated container is a rigid container with foam insulation. In several embodiments, the insulated container is a vacuum flask comprising a chamber with a pressure below atmospheric pressure to reduce heat transfer through the vacuum flask.

In several embodiments, a phase change system comprises the first phase change material and the second phase change material such that the phase change system is configured to change phases at multiple temperatures greater than 40 degrees Fahrenheit and less than 100 degrees Fahrenheit. For example, the first phase change material can solidify at 68 degrees Fahrenheit, and the second phase change material can melt at 82 degrees Fahrenheit. The phase change system can include many chambers. Some embodiments include at least four phase change materials and at least ten chambers with walls separating the chambers. The phase change system can be located inside the insulated container. At least a majority of the first chamber can be located between portions of the phase change system. For example, a first phase change material can be located on one side of the first chamber and a second phase change material can be located on an opposite side of the first chamber such that the phase change system "sandwiches" the first chamber.

In some embodiments, at least the majority of the first chamber is located between a first compliant wall and a second compliant wall. The first compliant wall can separate at least the majority of the first chamber from a first side of the phase change system. The second compliant wall can separate at least the majority of the first chamber from a second side of the phase change system. The compliant walls can make the first chamber expandable.

In several embodiments, the opening that leads into the first chamber comprises a length from a first end of the opening to a second end of the opening. The first chamber can comprise a minimum thickness between the first compliant wall and the second compliant wall in a location configured to hold the medicine. Prior to inserting the medicine into the first chamber, the length can be at least five times larger than the minimum thickness. The first chamber can be configured to expand in response to inserting the medicine into the first chamber such that the first chamber is configured to hold the medicine having a thickness that is greater than the minimum thickness of the first chamber. These embodiments can enable a collapsible storage system that can more easily fit in a pocket, purse, or bag when not in use. For example, the outer walls of the storage system can contract inwards as the thickness of the first chamber is reduced.

In some embodiments, the storage system comprises a second chamber that holds the first phase change material. The second chamber can be located inside the insulated container. The opening can be coupled to the first chamber such that the opening is configurable to provide access to the first chamber to enable removing the medicine from the insulated container. When the opening is unsealed, a person can reach into the opening to grab the medicine in the first chamber.

In several embodiments, the first chamber has a longest dimension, and the second chamber has a longest dimension. The first chamber and the second chamber can be oriented such that the longest dimension of the first chamber and the longest dimension of the second chamber both point towards the same exterior side of the storage system (e.g., towards one end of the storage system or towards an opening of the storage system). When the longest dimension of the first chamber and the longest dimension of the second chamber both point towards the same exterior side of the storage system, a portion of the first chamber and at least a portion of the second chamber can run approximately alongside each other (e.g., even though a wall separates the first chamber from the second chamber). The first chamber and the second chamber can be oriented such that they extend distally in a first direction away from the opening. The insulated container can be a vacuum flask and/or a foam container.

In several embodiments, the insulated container comprises a central axis, and the first chamber extends distally away from the opening such that at least a majority of the central axis is located inside the first chamber. The second chamber can be located outside of the first chamber and radially outward from the central axis. The storage system can also comprise a third chamber having the second phase change material. The second chamber can be located inside the insulated container. The third chamber can be located outside of the first chamber and radially outward from the central axis. The insulated container can be a vacuum flask or a container with walls insulated by foam.

In several embodiments, the storage system includes a phase change system comprising the first phase change material and the second phase change material such that the phase change system is configured to change phases at multiple temperatures greater than 40 degrees Fahrenheit and less than 100 degrees Fahrenheit. The phase change system can be located inside the insulated container.

In some embodiments, the first chamber is located between a first wall and a second wall. In several embodiments, at least a majority of the first chamber is located between a first wall and a second wall. The first wall can separate the first chamber from a first side of the phase change system. The second wall separates the first chamber from a second side of the phase change system. The first and second walls can be rigid or compliant. Rigid walls can be rigid plastic or metal. Compliant walls can be made from plastic configured to bend without breaking to conform to many different shapes.

In several embodiments, a third wall passes through the central axis to separate the second chamber from the third chamber. The third wall can separate a distal portion of the phase change system from a proximal portion of the phase change system. The third wall can be perpendicular to the central axis to separate the distal portion from the proximal portion. The third wall can also be perpendicular to the central axis to separate a left half of the phase change system from a right half of the phase change system.

Some embodiments include a first wall that separates the first chamber having the medicine from the second chamber having the first phase change material. A second wall can separate the first chamber having the medicine from the third chamber having the second phase change material. The first chamber, the second chamber, and the third chamber can extend distally parallel relative to each other. The first chamber, the second chamber, and the third chamber can be oriented such that they are located next to each other while being separated by walls.

In several embodiments, the insulated container comprises a vacuum flask having a cylindrical interior wall, which forms a cylindrical interior volume that is divided into chambers by walls that can be rigid or pliable. In some embodiments, phase change materials are located in compliant bags, the walls of which separate chambers. The medicine can be located inside the first chamber.

In several embodiments, the insulated container comprises a central axis, and the phase change system can be located in a central portion of the insulated container such that at least a majority of the central axis is located inside the phase change system (e.g., while a first medicine is located radially outward from at least a portion the phase change system and a second medicine is located radially outward from at least the portion of the phase change system). A first wall can separate the first chamber having the medicine from the phase change system. A second wall can separate the phase change system from a fourth chamber. The storage system can also include a removable lid (e.g., a "screw-on" lid) coupled to the base such that removing the lid facilitates accessing both the first chamber and the fourth chamber such that an injection device can be removed from the fourth chamber.

In some embodiments, the first chamber can be located radially outward from the central axis on a first side of the phase change system. The fourth chamber can be located radially outward from the central axis on a second side of the phase change system. A third wall can pass through the central axis to separate the second chamber from the third chamber.

In several embodiments, storage systems include a phase change system comprising the first phase change material and the second phase change material such that the phase change system is configured to change phases at multiple temperatures greater than 40 degrees Fahrenheit and less than 100 degrees Fahrenheit. Some embodiments of phase change systems change phases at multiple temperatures greater than 34 degrees Fahrenheit and/or less than 110 degrees Fahrenheit; and/or change phases at multiple temperatures greater than 62 degrees Fahrenheit and/or less than 82 degrees Fahrenheit. The insulated container can comprise a central axis, and the first chamber can extend distally away from the opening such that at least a portion of the central axis is located inside the first chamber. The phase change system can be located inside the insulated container and can be located distally relative to the first chamber. The phase change system can comprise a second chamber having the first phase change material.

In some embodiments, the phase change system can comprise a third chamber. The second phase change material can be located inside the third chamber. The phase change system can comprise a wall located distally relative to the first chamber. The wall can separate the second chamber from the third chamber. The insulated container can comprise a vacuum flask having a cylindrical interior wall. The medicine can located inside the first chamber.

In several embodiments, the storage system comprises a second chamber having the first phase change material. The second chamber can be located inside the insulated container. The opening can be coupled to the first chamber such that the opening is configurable to provide access to the first chamber to enable removing the medicine from the insulated container. Closing the opening can include using a lid or closing mechanism to shut the opening (in an air-tight or non-air-tight manner).

In some embodiments, the insulated container comprises a central axis, and the first chamber extends from the opening to a distal half of the insulated container. The storage system can also comprise a second chamber having the first phase change material and a third chamber having the second phase change material. The second chamber and the third chamber can be located outside of the first chamber and radially outward relative to the central axis.

In several embodiments, a first wall separates the first chamber from the second chamber, and a second wall separates the second chamber from the third chamber. The second chamber can be located distally or proximally relative to the third chamber while being located outside of the first chamber and radially outward relative to the central axis.

All of the apparatus and system embodiments described herein can be used with any of the methods described herein. Elements from one embodiment can be combined with elements of other embodiments.

Some embodiments include using a storage system having a first chamber configured to hold a medicine, a second chamber having a first phase change material, and a third chamber having a second phase change material. The first phase change material can have a first melting temperature that is greater than 40 degrees Fahrenheit and less than 74 degrees Fahrenheit. The second phase change material can have a second melting temperature that is greater than 74 degrees Fahrenheit and less than 100 degrees Fahrenheit. The first melting temperature can be at least four degrees Fahrenheit less than the second melting temperature (e.g., to ensure there is an adequate difference between the melting temperatures to reduce the likelihood of inappropriate melting and solidifying).

A manufacturer of the medicine can recommend a minimum storage temperature and a maximum storage temperature for the medicine. For example, the medicine can include instructions for use that state to store the medicine at 68 degrees Fahrenheit to 77 degrees Fahrenheit (as can be the case with EpiPens made by Meridian Medical Technologies, Inc., a Pfizer Company).

Some embodiments include obtaining the storage system. The storage system can have a first temperature. Embodiments can include placing the storage system inside a building having a first room temperature; leaving the storage system inside the building until the first phase change material is melted and the second phase change material is solidified; placing the medicine inside the first chamber and then closing (e.g., covering an opening) the first chamber from an external environment located outside of the storage system; moving the storage system to a cold environment that is colder than the first room temperature, colder than the first melting temperature, and/or colder than the minimum storage temperature of the medicine, then returning the storage system to a second room temperature before the first phase change material is completely solidified; and/or moving the storage system to a hot environment that is warmer than the first room temperature, warmer than the second melting temperature, and/or warmer than the maximum storage temperature of the medicine. Then, embodiments can include returning the storage system to a third room temperature before the second phase change material is completely melted.

As used herein, "room temperature" is used in a very broad sense, and can include a temperature inside a building and/or a temperature in a temperature-controlled building. The first, second, and third room temperatures can be equal to each other or different from each other. The first, second, and third room temperatures can be in the same building and/or room. The first, second, and third room temperatures can be in different buildings and/or rooms.

After returning the storage system to the second room temperature, some methods include exposing the storage system to the second room temperature until the first phase change material is melted before moving the storage system to a first extreme environment that is colder than the minimum recommended storage temperature. After returning the storage system to the third room temperature, some methods include exposing the storage system to the third room temperature until the second phase change material is solidified before moving the storage system to a second extreme environment that is hotter than the minimum recommended storage temperature.

Several embodiments include continuing to cover (e.g., covering an opening) the first chamber from the external environment from a first time the storage system leaves a fourth room temperature to move to the cold environment; while the storage system is located in the cold environment; and/or until returning the storage system to an environment having a fifth room temperature. Embodiments can also include opening the first chamber to the fifth room temperature in response to returning to the fifth room temperature. Several embodiments include continuing to open the first chamber to the fifth room temperature until the first phase change material is melted and the second phase change material is solidified.

As used herein, "cover" and "covering" are used in a very broad sense to mean covering an opening (e.g., by closing the opening or placing a lid in the opening). "Cover" and "covering" can include "seal" and "sealing," but in some embodiments, "cover" and "covering" might not form an air-tight seal. For example, a lid of a cooler can cover the opening to the cooler, but the lid does not necessarily form an airtight seal.

Several embodiments include obtaining the storage system; placing the storage system in a first inside environment; leaving the storage system in the first inside environment until the first phase change material is melted and the second phase change material is solidified; placing the medicine inside the first chamber and then closing the first chamber from an external environment (e.g., covering an opening leading to the first chamber), wherein the external environment is external relative to the storage system; moving the storage system to a cold outdoor environment that is colder than the first inside environment, colder than the first melting temperature, and/or colder than the minimum storage temperature of the medicine; and then returning the storage system to a second inside environment before the first phase change material is completely solidified. Some embodiments include moving the storage system to a hot outdoor environment that is warmer than the second inside environment, warmer than the second melting temperature, and/or warmer than the maximum storage temperature of the medicine, and then returning the storage system to a third inside environment before the second phase change material is completely melted.

As used herein, an environment is a cold outdoor environment if it is colder than the first inside environment. As used herein, an environment is a hot outdoor environment if it is hotter than the second inside environment. For example, a cold outdoor environment can be colder than a room temperature and a hot outdoor environment can be hotter than the room temperature.

In several embodiments, the medicine comprises a minimum storage temperature and a maximum storage temperature configured to avoid temperature-induced damage to the medicine. (The manufacturer of the medicine can recommend the minimum and maximum storage temperatures.) The first melting temperature can be equal to or within 7 degrees Fahrenheit greater than the minimum storage temperature. The second melting temperature can be equal to or within 7 degrees Fahrenheit less than the maximum storage temperature to reduce a temperature difference between the first chamber and an outside environment during a phase change of the first phase change material or the second phase change material.

In some embodiments, the first phase change material has a first melting temperature between 33 degrees Fahrenheit and 72 degrees Fahrenheit, and the second phase change material has a second melting temperature between 78 degrees Fahrenheit and 110 degrees Fahrenheit. The first chamber can be located at least partially between a second chamber and a third chamber. A first wall can separate the first chamber from the second chamber. A second wall can separate the first chamber from the third chamber. A first pliable bag can hold the first phase change material inside the second chamber. A second pliable bag can hold the second phase change material inside the third chamber. In some embodiments, the first pliable bag is the second chamber. In several embodiments, the first pliable bag is located within a chamber with rigid walls.

In several embodiments, the first chamber comprises a first central axis, the second chamber comprises a second central axis, and the third chamber comprises a third central axis. The first central axis, the second central axis, and/or the third central axis can be oriented parallel relative to each other.

In some embodiments, the first chamber can be located at least partially between a second chamber and a third chamber. The second chamber can be located radially outward from the first central axis on a first side of the first chamber. The third chamber can be located radially outward from the central axis on a second side of the first chamber.

In several embodiments, the first chamber, the second chamber, and the third chamber are located inside a cylindrical void of the insulated container. The cylindrical void can be an interior portion of a vacuum flask with a screw-on lid.

In some embodiments, a first wall separates the first chamber from the second chamber; a second wall separates the first chamber from the third chamber; a first pliable bag holds the first phase change material inside the second chamber; and/or a second pliable bag holds the second phase change material inside the third chamber. In several embodiments, the pliable bag forms a pliable chamber.

BRIEF DESCRIPTION OF THE DRAWINGS

These and other features, aspects, and advantages are described below with reference to the drawings, which are intended to illustrate but not to limit the invention. In the drawings, like reference characters denote corresponding features consistently throughout similar embodiments.

FIGS. 26 and 27 illustrate perspective views of chambers with phase change materials, according to some embodiments.

FIG. 28 illustrates a cross-sectional view of the storage system along line A-A from FIG. 25, according to some embodiments.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. The features of each embodiment can be combined with the other embodiments.

Several embodiments of a storage system for injectable substances include a thermally insulating container. A substance with a high heat capacity can be located inside the insulating container. The substance can have a specific heat capacity of at least 2 Joules/gram*Kelvin and/or a volumetric heat capacity of at least 2 Joules/cm^3*Kelvin. A chamber configured to hold an injectable substance can also be located inside the insulating container. In some embodiments, the substance with a high heat capacity at least partially surrounds at least a portion of the chamber configured to hold the medicine (e.g., an injectable substance).

Figure 1:
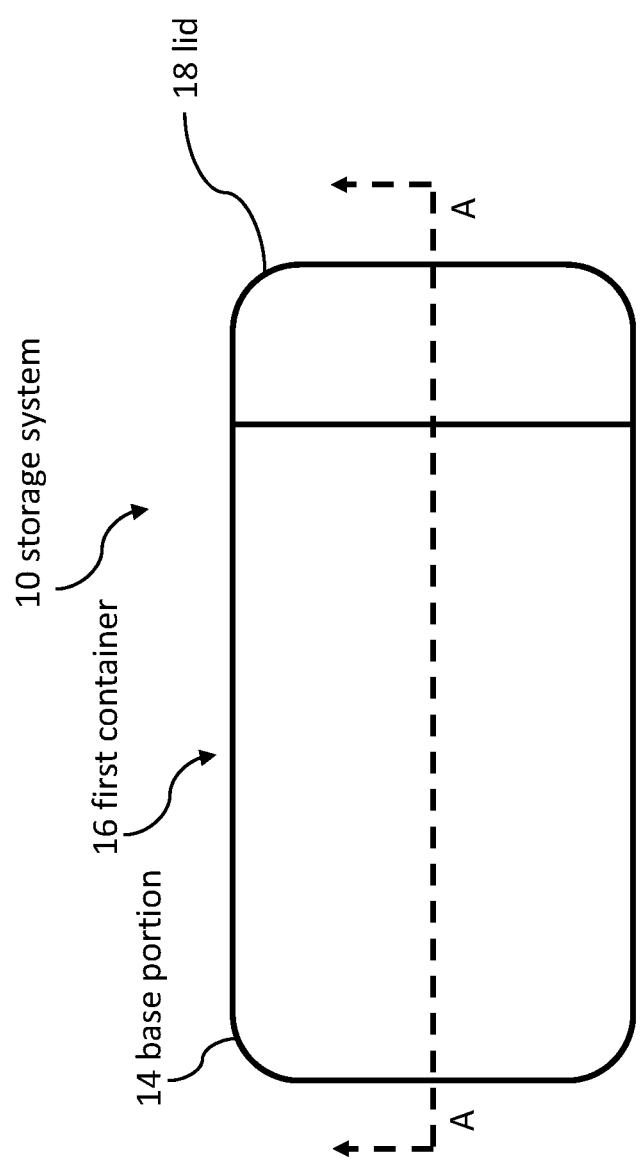
FIG. 1 illustrates a side view of a storage system, according to some embodiments.

FIG. 1 illustrates an embodiment of a storage system 10. The storage system 10 can have a base portion 14 and a lid 18. The storage system 10 can be configured to store injectable substances such as epinephrine, adrenaline, and/or insulin such that the temperature of the injectable substances is maintained within a suitable temperature range, which can be approximately room temperature or 75+/−10 degrees Fahrenheit, 75+/−15 degrees Fahrenheit, or 75+/−20 degrees Fahrenheit, according to several embodiments.

Figure 2:
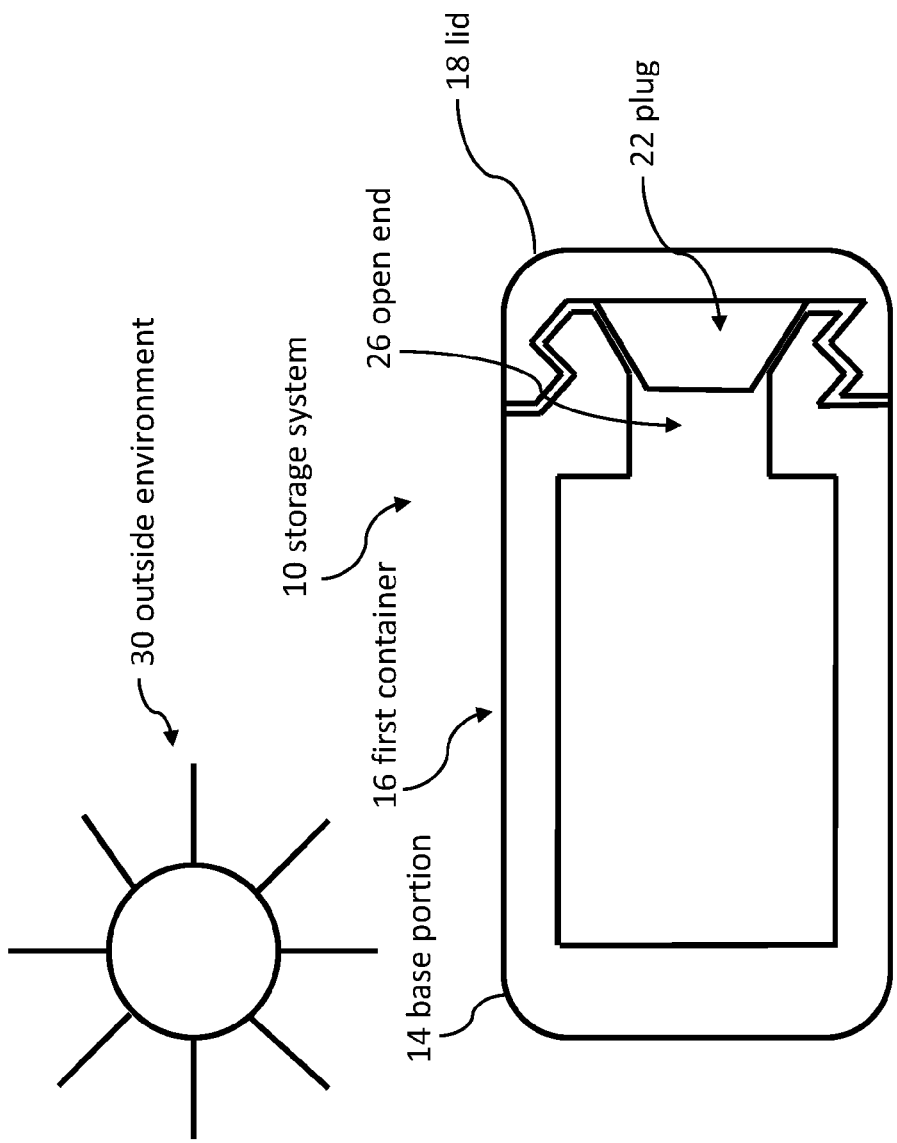
FIG. 2 illustrates a cross-sectional view of a storage system embodiment along plane A-A, which extends into the page in FIG. 1, according to some embodiments.

FIG. 2 illustrates a cross section of the storage system 10 along plane A-A, which extends into the page in FIG. 1. The lid 18 is coupled to the base portion 18 by threads such that the lid 18 can be twisted onto the base portion 14 to couple the lid 18 to the base portion 14. A plug 22 can seal and/or insulate an open end 26 of the base portion 14. Coupling the lid 18 to the base portion 14 can push the plug 22 towards the base portion 14 to seal and/or insulate an internal portion of the storage system 10 from the outside environment 30, which is represented in FIG. 2 as the sun. The outside environment 30 is the environment outside of the storage system 10. For example, the outside environment 30 could be a cold, snowy day or a hot, dry day.

Figure 3:
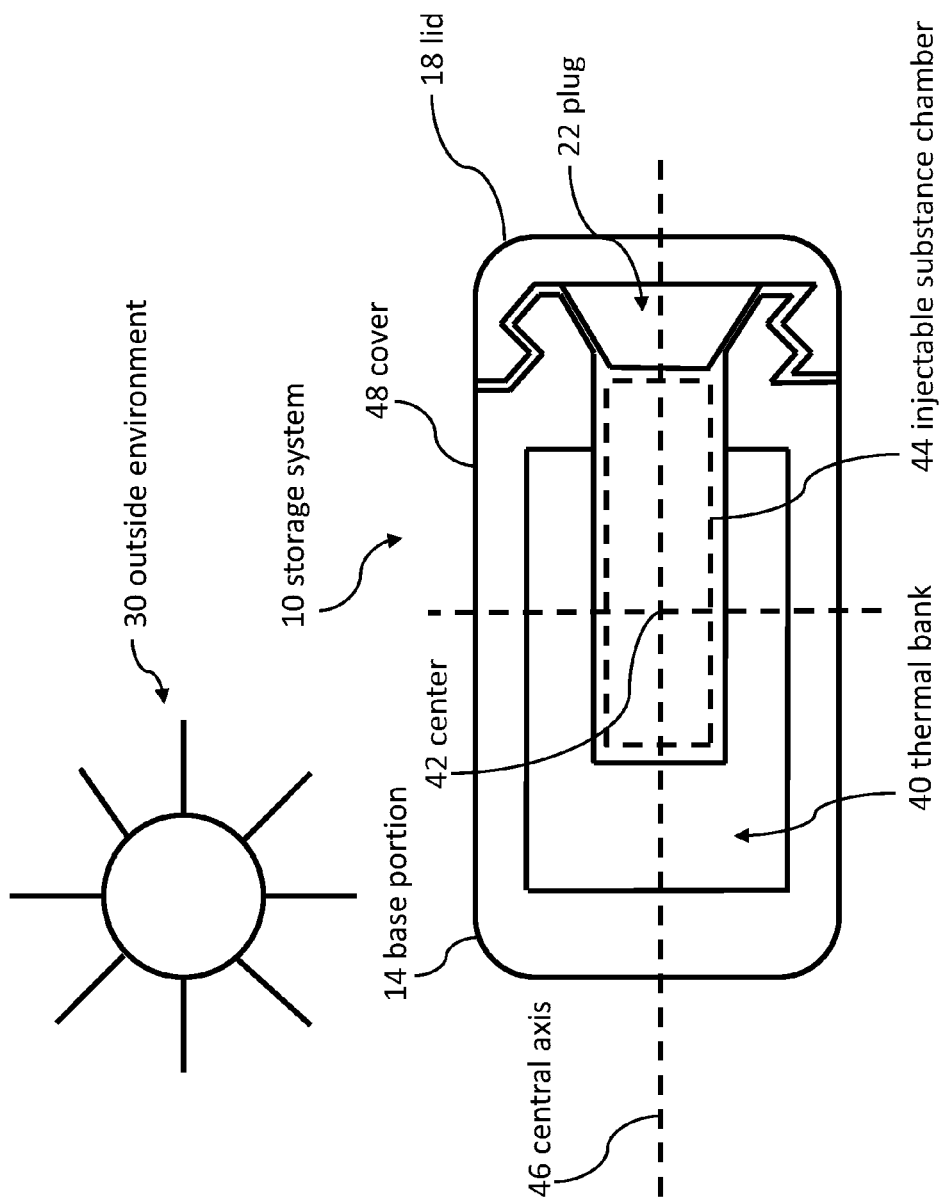
FIG. 3 illustrates the same cross section as illustrated in FIG. 2 except some items omitted from FIG. 2 to increase the clarity of FIG. 2 are visible in FIG. 3, according to some embodiments.

FIG. 3 illustrates the same cross section as illustrated in FIG. 2 except items omitted from FIG. 2 to increase the clarity of FIG. 2 are visible in FIG. 3. In some embodiments, the storage system 10 includes a thermal bank 40 that is located inside a cover 48 that insulates the thermal bank 40 from the outside environment 30. The cover 48 is configured to insulate the thermal bank 40. The cover 48 can include a vacuum chamber, a vacuum flask, foam, and/or plastic walls separated by air. In some embodiments, the cover 48 is an insulated cover. The lid 18 can also include one or more insulators such as foam, a vacuum chamber, and plastic walls separated by air. The lid 18 can include a thermometer.

In several embodiments, a "thermal bank" can be a component or assembly that has a heat capacity of at least 400 J/K. In several embodiments, thermal banks have a heat capacity that is large enough to maintain the temperature of an injectable substance chamber 44 within an acceptable temperature range for an acceptable period of time. Acceptable temperature ranges and acceptable periods of time vary widely by application and design purpose. In some embodiments, thermal banks are at least partially filled with a liquid or a solid selected to provide sufficient heat capacity. In some embodiments, thermal banks have outer walls made of metal, glass, or plastic and are filled with a substance with sufficiently high heat capacity. In some embodiments, the substance with sufficiently high heat capacity is a solid at 75 degrees Fahrenheit, so outer walls are sometimes not included in thermal banks. For example, some thermal bank embodiments are sleeves of wax or metal.

Herein, Joule is often abbreviated as J, kelvin is often abbreviated as K, gram is often abbreviated as g, cubic centimeter is often abbreviated as cm^3, and Fahrenheit is often abbreviated as F. In some embodiments, the thermal bank 40 has a heat capacity of at least 400 J/K; at least 700 J/K; at least 1,400 J/K; at least 2,400 J/K; at least 3,200 J/K; at least 4,800 J/K; at least 7,200 J/K; at least 20,000 J/K; less than 7,200 J/K; and/or less than 30,000 J/K.

In some embodiments, the thermal bank 40 comprises a substance that has a specific heat capacity of at least 1 J/(g*K) at 75 degrees Fahrenheit, at least 2 J/(g*K) at 75 degrees Fahrenheit, at least 3 J/(g*K) at 75 degrees Fahrenheit, or at least 4 J/(g*K) at 75 degrees Fahrenheit. In some embodiments, the thermal bank 40 comprises a substance with a volumetric heat capacity of at least 1 J/(cm^3*K) at 75 degrees Fahrenheit, at least 2 J/(cm^3*K) at 75 degrees Fahrenheit, at least 3 J/(cm^3*K) at 75 degrees Fahrenheit, or at least 4 J/(cm^3*K) at 75 degrees Fahrenheit.

In several embodiments, a thermal bank and/or a substance with any of the heat capacities described herein has a volume of at least 50 cm^3 and/or less than 2,000 cm^3; at least 100 cm^3 and/or less than 1,000 cm^3; and/or at least 200 cm^3 and/or less than 500 cm^3. In some embodiments, the thermal bank is a reservoir or container filled with a fluid such as water. The reservoir or container can be made of plastic and can be a shell wherein an inner portion of the shell can be at least partially filled with a liquid and/or a phase change material. The center of the reservoir or container can include a channel or void that is fluidly isolated from the liquid inside the container. The channel or void can be configured to hold or store an injectable substance or an injection device. In some embodiments, the thermal bank has a generally cylindrical shape and/or a cylindrical channel or cylindrical void.

In some embodiments, the thermal bank 40 comprises ammonia, lithium, water, wax, and/or metal. In some embodiments, the thermal bank 40 comprises iron, copper, zinc, tungsten, aluminum, paraffin wax, lithium, granite, and/or magnesium. In some embodiments, the thermal bank 40 is a chamber that is at least 40%, at least 60%, or at least 80% filled with a solid and/or liquid such as ammonia, lithium, water, wax, and/or metal.

In several embodiments, a chamber 44 configured to hold an injectable substance is located inside the storage system 10. The injectable substance chamber 44 can be located approximately along the central axis 46 of the storage system 10. In FIG. 3, the injectable substance chamber 44 is highlighted by a dashed rectangle. The injectable substance chamber 44 (e.g., a medicine chamber) can be a hole, void, or open area. The injectable substance chamber 44 can include portions of the central axis 46. The injectable substance chamber 44 can include the volumetric center 42 of the storage system 10. A least a portion of the injectable substance chamber 44 can be at least partially surrounded by the thermal bank 40. In some embodiments, the injectable substance chamber 44 is located inside a portion of the thermal bank 40. In several embodiments, at least 40%, at least 60%, or at least 80% of the volume of the injectable substance chamber 44 is located inside the thermal bank 40. As illustrated in FIG. 3, a portion of the injectable substance chamber 44 can be located inside the thermal bank 40 even if the thermal bank 40 does not completely surround the injectable substance chamber 44.

The injectable substance chamber 44 can be configured to hold an injectable substance, which may be packaged in a separate storage container such as a plastic vial, a glass jar, and/or an injection device such as a syringe. Example injectable substances can be contained in products such as EpiPens, Twinjects, Adrenaclicks, Anapens, Jexts, Allerjects, Auvi-Qs, and ComboPens. Some injectable substance chambers 44 are configured to hold multiple containers of injectable substances. Some injectable substance chambers 44 are configured to hold an inhaler and/or another drug container.

As used herein, the term injectable substance can include a container that holds a liquid that users inject into their bodies. Some embodiments are similar to other embodiments described herein except the injectable substance is replaced with a container of an injectable liquid. The container can be plastic, glass, and/or a syringe.

Figure 4:
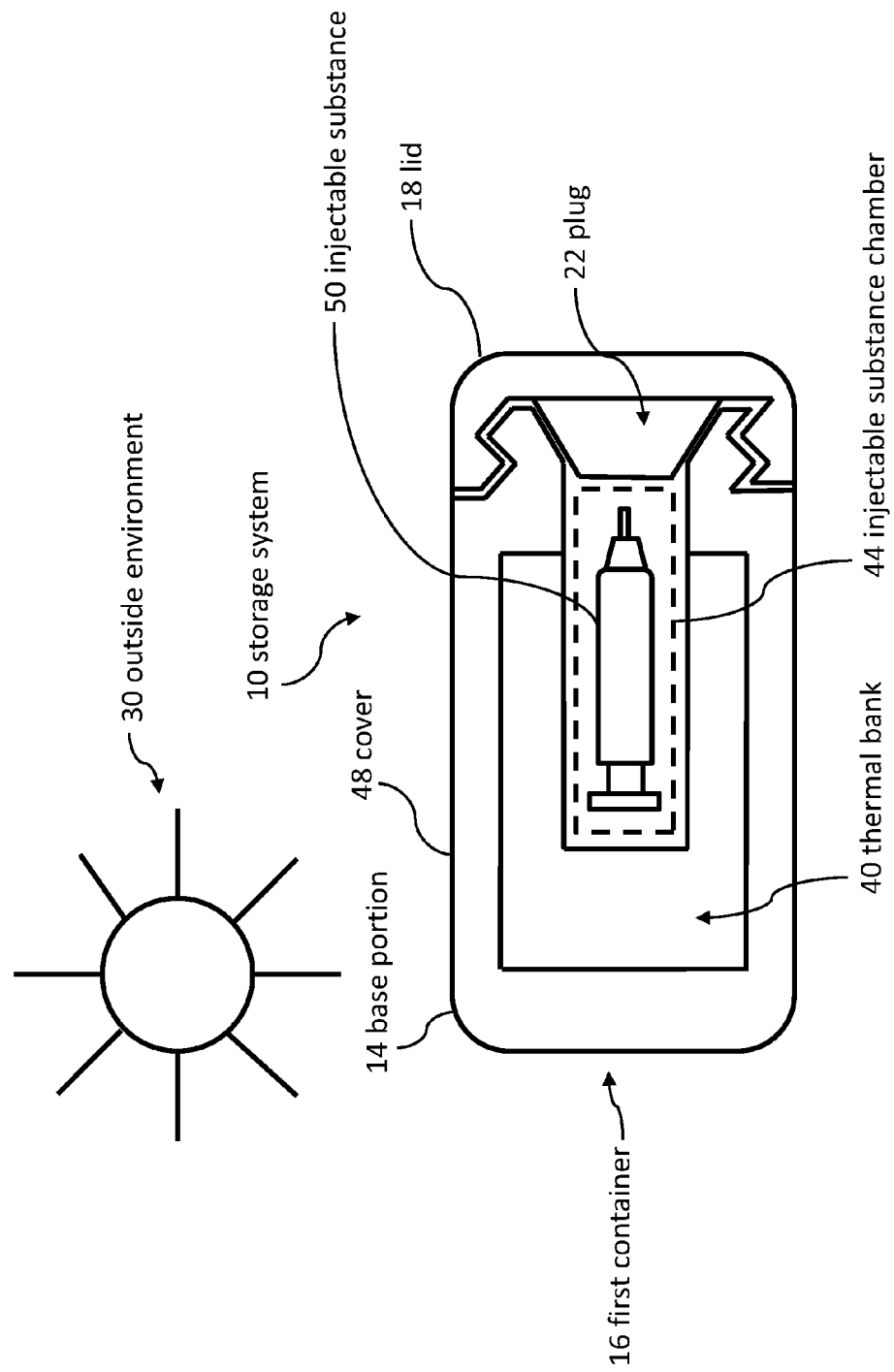
FIG. 4 illustrates a cross-sectional view wherein an injectable substance is located inside a chamber, according to some embodiments.

FIG. 4 illustrates an injectable substance 50 located inside the injectable substance chamber 44. In several embodiments, the injectable substance chamber 44 is isolated from liquids located inside the storage system 10 such that the storage system 10 is configured to keep the injectable substance 50 dry and/or away from liquids. In some embodiments, the storage system 10 does not include any liquids although some embodiments include a liquid, such as water, inside the thermal bank 40.

The injectable substance 50 can include epinephrine, adrenaline, insulin, hormones, and/or neurotransmitters. The injectable substance 50 can include liquids or gases used to treat acute allergic reactions, to avoid anaphylactic shock, and/or to treat anaphylactic shock. The injectable substance 50 can include liquids or gases used to treat diabetes. In some embodiments, the injectable substance 50 is an epinephrine auto-injector such as the EpiPen or EpiPen Jr. made by Mylan Specialty L.P. In some embodiments, the injectable substance is replaced by another pharmaceutical product or by another product that benefits from temperature stability.

Figure 5:
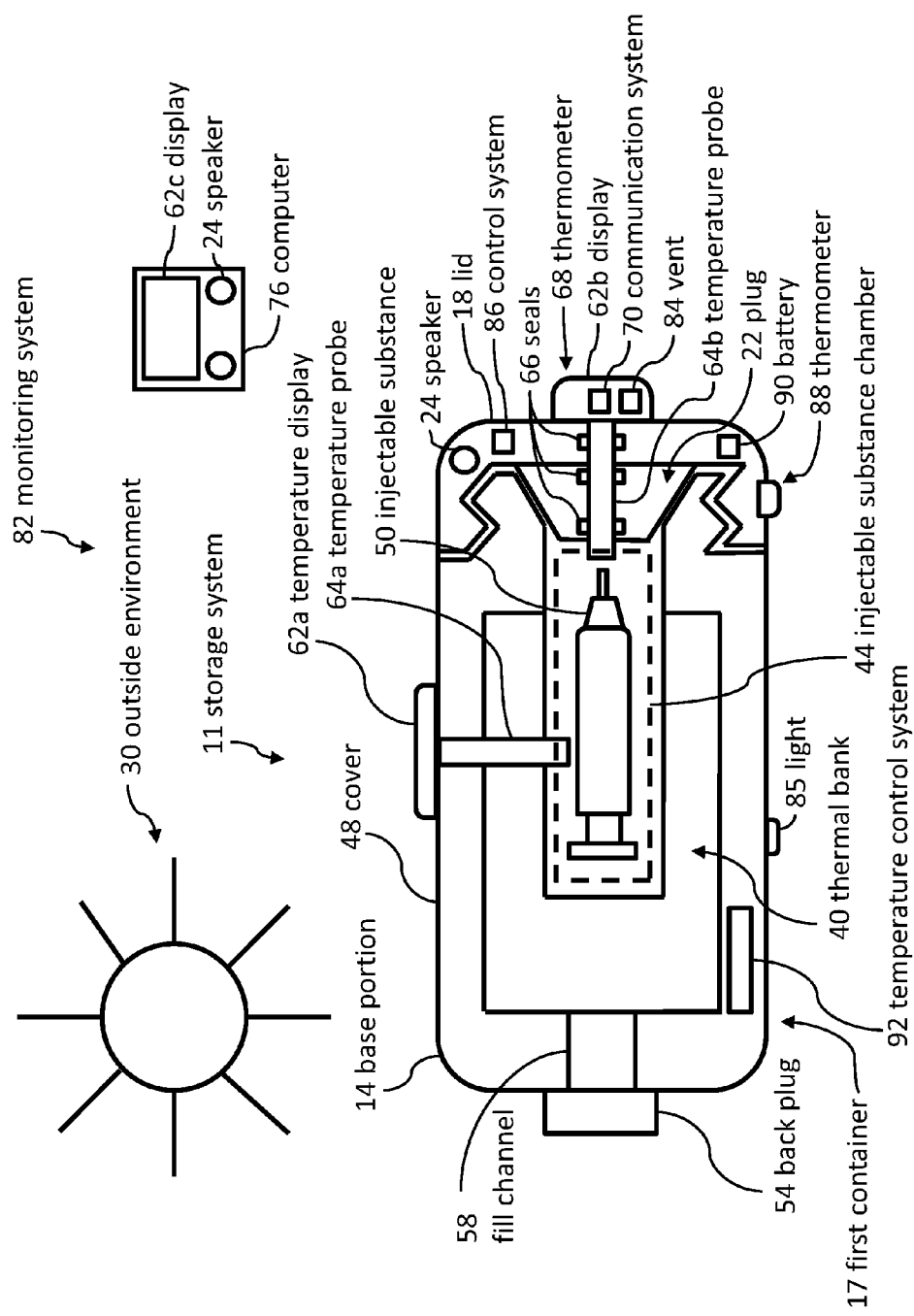
FIG. 5 illustrates a cross-sectional view of another embodiment of a storage system, according to some embodiments.

FIG. 5 illustrates another embodiment of a storage system 11. The many features described in the context of FIG. 5, including but not limited to the electronic features and the computer 76, can be combined with any of the features described in the context of FIGS. 1-4 and FIGS. 6-37. To reduce redundancy and to increase the clarity of other features in other figures, the features described in the context of FIG. 5 are not repeated for each figure. The lid 18 shown in FIG. 5 can be used with any of the storage systems described herein to combine many electrical elements with many types of storage systems.

The storage system 11 includes a back plug 54, which can be a removable plug made of rubber that threads into the base portion 14 or uses a friction fit (or interference fit) with an opening in the base portion 14. Removing the back plug 54 can expose a fill channel 58 that is configured to allow a substance with sufficient heat capacity to go into the thermal bank 40. For example, a user or a manufacturer could open the back plug 54 and pour a liquid such as water into the thermal bank 40. In some embodiments, a user can pour water with a temperature that is lower than the suitable range if the user intends to enter an outside environment 30 with a temperature that is higher than the suitable range. In some embodiments, a user can pour water with a temperature that is higher than the suitable range if the user intends to enter an outside environment 30 with a temperature that is lower than the suitable range.

Some embodiments include a thermometer, which can include a temperature probe 64a. At least a portion of the temperature probe 64a can be located inside the injectable substance chamber 44 (e.g., a first chamber) such that the temperature probe 64a is configured to measure, evaluate, test, and/or determine the temperature inside the injectable substance chamber 44 and/or the temperature of the injectable substance 50. The thermometer can also include a temperature display 62a, which can be located outside of the cover 48 such that the temperature display 62a is configured such that a user can read and/or determine the temperature on the display 62a without opening the lid 18. A speaker 24 can emit a sound to warn the user if a temperature inside the storage system 11 exceeds a predetermined temperature threshold or falls below a predetermined temperature threshold.

In some embodiments, a computer 76, a display 62b, and/or the speaker 24 warns the user if a temperature, such as the temperature of the first chamber, an injectable substance, a medicine, and/or a thermal bank, deviates outside of a predetermined temperature range.

Any of the storage systems described herein can include a thermometer 68, which can be integrated into a lid 18, 18b. The thermometer can include a temperature display 62b and a temperature probe 64b that protrudes distally to pass through portions of the lid 18 and/or the plug 22. In the interest of clearly showing other features in other figures, the thermometer 68 and related components are hidden in many of the figures. The thermometers 68, 88, the speaker 24, the control system 86, the battery 90, the seals 66, the display 62b, the communication system 70, the vent 84, the temperature probe 64b, and related components can be included in many types of storage systems 10, 11, 12, 200a, 200b, 200c, 200d, 200e, 200f, 200g, 200h, 200i, 300.

The lid 18 can be used with any of the storage system embodiments shown in the figures and/or described herein. The thermometers 68, 88, the speaker 24, the control system 86, the battery 90, the seals 66, the display 62b, the communication system 70, the vent 84, the temperature probe 64b, and related components can be integrated into the lid 18b shown in FIG. 15. Thus, the lid 18b can include all the features of the lid 18 (shown in FIG. 5).

The battery 90 can supply electrical power to the thermometers 68, 88, the speaker 24, the control system 86, the displays 62a, 62b, the communication system 70, the vent 84, the temperature probes 64a, 64b, and related components. In some embodiments, the battery 90 also supplies electrical power to a temperature control system 92, which can include a heater and/or a refrigerator. The temperature control system 92 can be included in any of the storage systems described herein (e.g., 10, 11, 12, 200a, 200b, 200c, 200d, 200e, 200f, 200g, 200h, 200i, 300), however, many storage systems do not include a temperature control system 92. The communication system 70 can show an alert on the display 62b, emit an alert sound from the speaker 24, and/or send an alert to the computer 76 if the battery's capacity (e.g., charge level) falls below a predetermined threshold.

A temperature display 62b can be coupled to the lid 18 such that the temperature display faces outward (e.g., in a proximal direction) from the lid 18 and faces outward from the proximal end of the storage system 11. A temperature probe 64b can protrude distally (e.g., through a portion of the central axis of the storage system 11) into a first chamber (e.g., the injectable substance chamber 44). A portion of the plug 22 can be hollow. The temperature probe 64b can extend through the hollow portion of the plug 22. The plug can also be filled with insulation, such as foam insulation. At least a portion of the temperature probe 64b can be surrounded by the insulation located inside the plug 22 and/or inside the proximal portion of the lid 18.

Placing the temperature probe 64b through the lid 18 and/or the plug 22 can be advantageous compared to placing the temperature probe 64b through a vacuum chamber (because the temperature probe 64b could jeopardize the airtight nature of various vacuum chambers).

Seals 66 can be located along portions of the temperature probe 64b that pass through the plug 22 and/or portions of the lid 18. The seals 66 can wrap around the probe 64b.

In some embodiments, the plug 22 is integrated into the lid 18. In some embodiments, the plug 22 is a separate component from the lid 18. Even if the plug 22 is a separate component, in several embodiments, the lid 18 presses the plug 22 distally into an opening of the first chamber.

The thermometer 68 can include a wireless communication system 70 to wirelessly communicate with a computer 76. The computer 76 can be located remotely relative to the storage system 11. Thus, the storage system 11 can send information regarding the temperature of a first chamber (e.g., the injectable substance chamber 44) to the computer 76 via any suitable wireless communication system including Bluetooth, WiFi, cellular communication, radio communication, and/or the Internet. The computer 76 can be a laptop computer, a desktop computer, a tablet computer, a watch, a smartphone, and/or any other computing device capable of receiving and then displaying temperature information.

Storage systems 10, 11, 12, 200a, 200b, 200c, 200d, 200e, 200f, 200g, 200h, 200i, 300 can be configured to send alerts to the computer 76 regarding temperatures inside chambers (e.g., an injectable substance chamber, a first chamber) that are higher than a predetermined threshold or lower than a predetermined threshold. The predetermined thresholds can be entered into software (e.g., an "app") that runs on the computer 76. The predetermined thresholds can be entered into the control system 86 via a keypad coupled to the storage system 11. In some embodiments, the thresholds are equal to a minimum storage temperature and a maximum storage temperature for the medicine as recommended by the manufacturer of the medicine. Thus, the thermometer can measure a temperature of the first chamber and then can send an alert to the computer if the measured temperature is above or below predetermined thresholds. The alert can be a push notification. The alert can be displayed on the screen of the computer 76. The alert can be a sound emitted from a speaker of the computer or a speaker 24 of the storage system. The alert can show the current temperature inside the first chamber, the maximum temperature within the first chamber (e.g., within a certain time period), the minimum temperature within the first chamber (e.g., within a certain time period), the minimum and/or maximum storage temperature, and/or the predetermined thresholds set by a user of the computer 76 and/or a monitoring system 82. The monitoring system 82 can include the computer 76 and a storage system (e.g., 10, 11, 12, 200a, 200b, 200c, 200d, 200e, 200f, 200g, 200h, 200i, 300).

In several embodiments, the alert can be a sound emitted by the speaker 24 of the lid 18 (or of another part of a storage system). The speaker 24 can emit a sound (e.g., an alert) in response to an internal temperature of the storage system being above or below a predetermined range (e.g., a range defined by the user based on the minimum and maximum recommended storage temperatures), and/or in response to the internal temperature being within a predetermined number of degrees of the minimum and maximum recommended storage temperatures.

In some embodiments, the monitoring system 82 determines a temperature inside the first chamber, and then calculates, estimates, and/or displays a time until the temperature of the first chamber reaches the minimum and/or maximum storage temperature, and/or the predetermined thresholds. A display screen (e.g., a display of the computer 76, the temperature display 62b) can show an indication of the current temperature inside the first chamber and can show a time until the temperature inside the first chamber reaches the minimum and/or maximum storage temperature, and/or the predetermined thresholds. For example, the display screen should show "69 degrees Fahrenheit" as a recent measurement of the temperature inside the first chamber and could show "5 hours" as the estimate time until the temperature of the first chamber reaches the minimum and/or maximum storage temperature, and/or one of the predetermined thresholds. The time until the temperature reaches one of the limits can be updated periodically.

In several embodiments, the display 62b includes lights (e.g., a green light, an orange light, and a red light). A first light can indicate that the internal temperature is within a safe range. A second light can indicate the internal temperature is within a certain amount of the predetermined maximum or minimum storage temperatures (e.g., within at least one degree and/or within at least five degrees of the predetermined maximum or minimum storage temperatures without being above the maximum storage temperature or below the minimum storage temperature). A third light can indicate that the internal temperature is above the maximum storage temperature or below the minimum storage temperature.

In some embodiments, the monitoring system 82 detects a temperature of an external environment (e.g., via a thermometer 88 configured to measure an external temperature). Then, the monitoring system 82 displays a notification on the computer 76 or display 62a, 62b that instructs the user to open and/or close an opening to the first chamber in response to a comparison of an external temperature to the temperature of the first chamber.

If the temperature of the first chamber is warmer than a target temperature, but the external temperature is cooler than the first chamber, then the notification can instruct the user to open the opening to the first chamber. If the temperature of the first chamber is cooler than a target temperature, but the external temperature is warmer than the first chamber, then the notification can instruct the user to open the opening to the first chamber.

If an external temperature is warmer than a target temperature, but the first chamber is cooler than the external temperature, then the notification can instruct the user to close the opening to the first chamber. If an external temperature is cooler than a target temperature, but the first chamber is warmer than the external temperature, then the notification can instruct the user to close the opening to the first chamber.

In some embodiments, instead of or in addition to the notifications, the monitoring system 82 can automatically open and close an opening (e.g., a vent 84) to the first chamber. The vent 84 can be an automatic vent that can open and close in response to commands from an electronic control system 86 that is part of the storage system (e.g., 10, 11, 12, 200a, 200b, 200c, 200d, 200e, 200f, 200g, 200h, 200i, 300).

The vent 84 can be a closeable passageway that extends from an external opening to a portion of the first chamber. The vent 84 can include a motorized seal configured to open and close in response to commands from the electronic control system 86. The computer 76 can wirelessly set control parameters for the vent 84.

If the temperature of the first chamber is warmer than a target temperature, but the external temperature is cooler than the first chamber, then the electronic control system 86 can open the vent 84 to the first chamber. If the temperature of the first chamber is cooler than a target temperature, but the external temperature is warmer than the first chamber, then the electronic control system 86 can open the vent 84 to the first chamber.

If an external temperature is warmer than a target temperature, but the first chamber is cooler than the external temperature, then the electronic control system 86 can close the vent 84 to the first chamber. If an external temperature is cooler than a target temperature, but the first chamber is warmer than the external temperature, then the electronic control system 86 can close the vent 84 to the first chamber.

Figure 6:
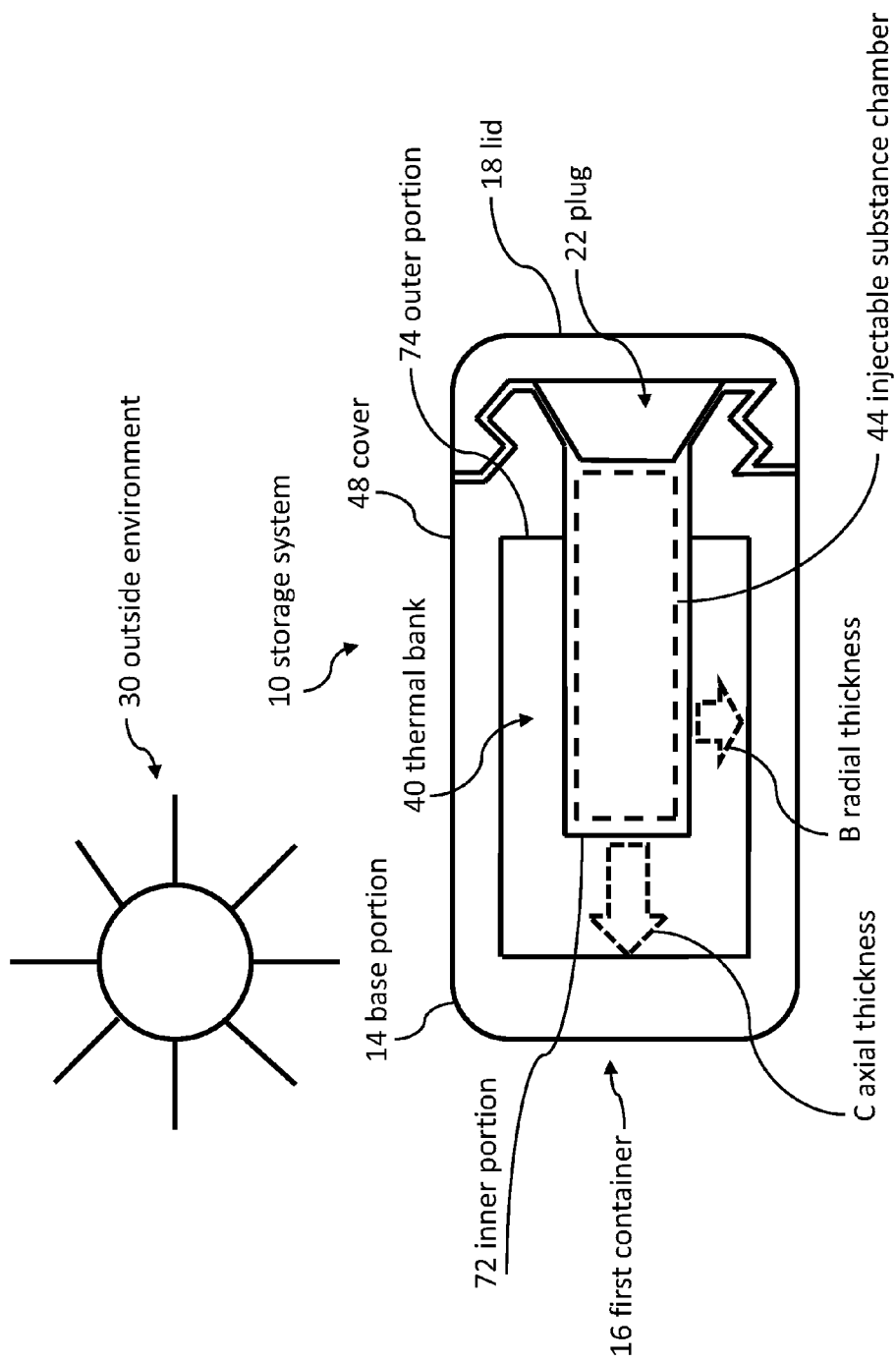
FIG. 6 illustrates a radial thickness of a thermal bank, according to some embodiments.

FIG. 6 illustrates thicknesses of the thermal bank 40, according to several embodiments. In some embodiments, the radial thickness (as illustrated by dashed arrow B) of the thermal bank 40 is at least 3 millimeters ("mm") and/or less than 100 mm; at least 7 mm and/or less than 200 mm; and/or at least 20 mm and/or less than 200 mm. In some embodiments, the axial thickness (as illustrated by dashed arrow B) of the thermal bank 40 is at least 10 mm and/or less than 100 mm; at least 20 mm and/or less than 200 mm; and/or at least 40 mm and/or less than 200 mm.

Some embodiments include an insulated container configured to maintain injectable substances at approximately room temperature. In several embodiments, the insulated container can include a chamber configured to hold an injectable substance. The chamber can be surrounded by a substance with high heat capacity. The substance with high heat capacity can be surrounded by an insulated cover.

Figure 7:
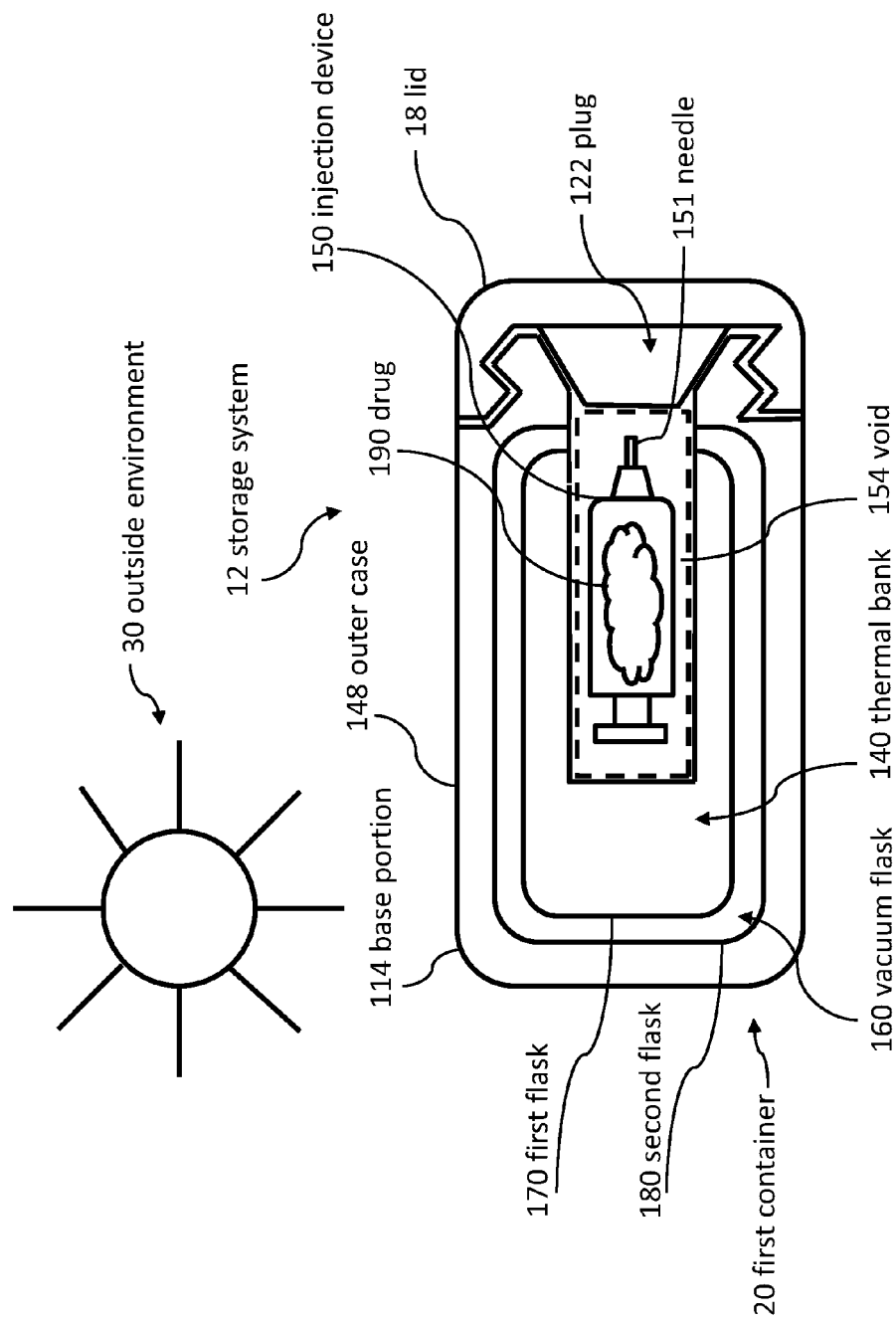
FIG. 7 illustrates a cross-sectional view of another embodiment of a storage system, according to some embodiments.

FIG. 7 illustrates another embodiment of a storage system 12. The storage system 12 can include an outer case 148, which can be made of plastic or metal. The storage system can include a vacuum chamber (e.g., in a vacuum flask 160). The vacuum flask 160 can be located inside the outer case 148 such that the outer case 148 can be configured to protect the vacuum flask 160 from damage such as denting or cracking. The vacuum flask 160 can comprise an inner wall and an outer wall with a gas pressure between the inner wall and the outer wall that is less than atmospheric pressure. In some embodiments, the pressure between the inner wall and the outer wall can be less than 60% of atmospheric pressure, less than 40% of atmospheric pressure, or less than 20% of atmospheric pressure. The atmospheric pressure can be measured at sea level. The vacuum flask 160 can include a first flask 170 placed inside a second flask 180. The first flask 170 and the second flask 180 can be joined at the neck such that the area between the first flask 170 and the second flask 180 is hermetically sealed from the air outside of the area between the first flask 170 and the second flask 180. The vacuum flask 160 can be made of metal, glass, foam, or plastic.

A thermal bank 140 can be located inside the vacuum flask 160. In some embodiments, the thermal bank 140 comprises a heat capacity of at least 4,800 J/K. The thermal bank 140 can comprise a void 154 that extends from an inner portion of the thermal bank to an outer portion of the thermal bank. In some embodiments, the void is at least 1 cm wide and/or less than 10 cm wide; or at least 2 cm wide and/or less than 20 cm wide. The void 154 can be an injectable substance chamber. In FIG. 7, a dashed rectangle is used to highlight the void 154.

In several embodiments, the void 154 is configured to store, hold, and/or contain an injectable substance 50, an injection device 150, a liquid manufactured to inject into a human body, and/or a syringe. In some embodiments, an injectable substance 50, an injection device 150, epinephrine, adrenaline, insulin, and/or a syringe is located inside the void. A removable lid 18 can be configured to allow a user to remove the injectable substance 50, the injection device 150, epinephrine, adrenaline, insulin, and/or a syringe from the storage system. The removable lid 18 can press a rubber plug 122 onto an end of the vacuum flask 160 and/or onto a base portion 114.

Various embodiments are similar to other embodiments described herein except the injectable substance 50 is replaced with an injection device 150 that is at least partially filled with a pharmaceutical agent, epinephrine, adrenaline, insulin, a liquid manufactured for injection into a human body, and/or a liquid. FIG. 7 illustrates an injection device 150. An injection device 150 can be a syringe. In some embodiments, the injection device 150 is an EpiPen, a syringe with epinephrine, a syringe with insulin, a syringe with adrenaline, an auto-injector configured to deliver a liquid under the skin of a human or animal, and/or a device configured to deliver a drug under the skin of a human or animal. In some embodiments, the injection device 150 comprises a reservoir at least partially filled with a liquid. The injection device 150 can also comprise an orifice that is configured to deliver the liquid under the skin. The injection device 150 can also comprise a needle, a nozzle, and/or a tube configured to deliver a liquid and/or pharmaceutical substance under the skin.

Various embodiments are similar to other embodiments described herein except the injectable substance is replaced with a pharmaceutical, a pharmaceutical agent, a pharmaceutical substance, an inhaler, and/or a medical device. In some embodiments, the pharmaceutical agent and/or pharmaceutical substance is a medicinal drug 190, which can be a gas, liquid, or solid. For example, the drug 190 can be a medication contained in an inhaler for the treatment of asthma. In some embodiments, the drug 190 is a steroid, such as Flovent or fluticasone propionate, that reduces the release of substances in the body that cause inflammation to prevent asthma attacks.

FIG. 7 illustrates an embodiment with an outer case 148 and a lid 18. A vacuum flask 160 was placed inside the outer case 148. A thermal bank 140 was placed inside the vacuum flask 160. An injectable substance was placed inside the vacuum flask 160. The lid 18 was closed such that the outer case 148 and the lid 18 completely surround the injectable substance. The outer case 148 can be an insulated cover and/or can include insulation.

Figure 8:
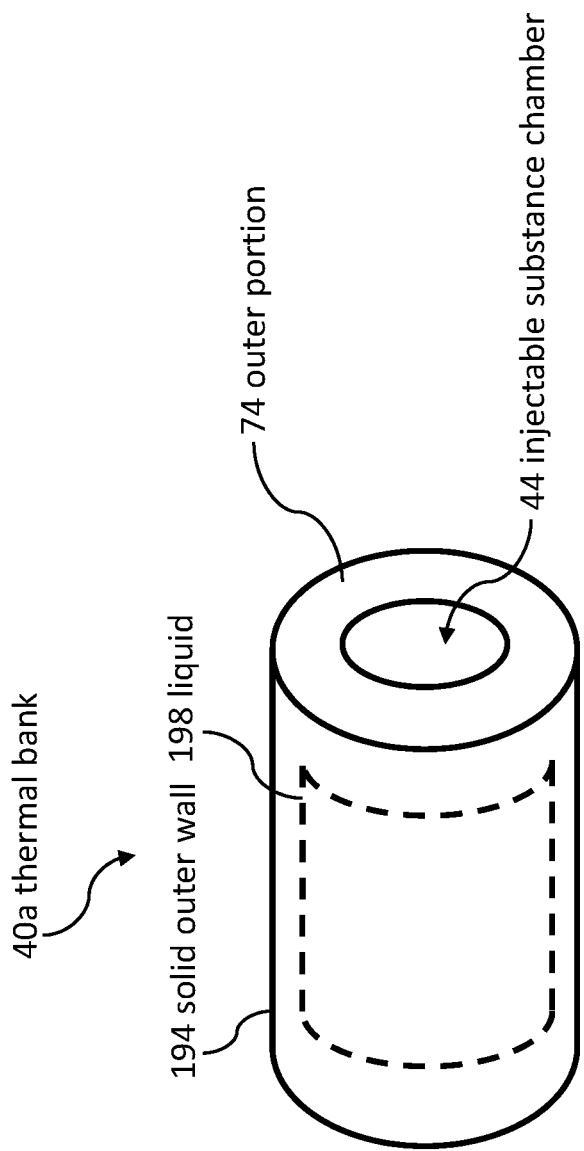
FIG. 8 illustrates a perspective view of a thermal bank, according to some embodiments.

FIG. 8 illustrates a perspective view of a thermal bank 40*a* with an injectable substance chamber 44 or void. The thermal bank 40*a* can be a container with solid outer walls 194 and can be at least partially filled with a liquid 198.

The thermal bank 40*a* can be located or placed inside a vacuum flask or vacuum chamber. The thermal bank 40*a* can comprise any of the heat capacities, specific heat capacities, volumetric heat capacities, and/or heat capacity characteristics described herein. The thermal bank 40*a* can comprise an injectable substance chamber 44 or void that extends from an inner portion 72 of the thermal bank 40*a* to an outer portion 74 of the thermal bank 40*a* (as illustrated in FIG. 6), wherein the injectable substance chamber 44 or void is at least 1 cm wide and 4 cm long. In some embodiments, an injectable substance, an injection device, a drug, a pharmaceutical agent, a pharmaceutical substance, and/or an inhaler is located inside the injectable substance chamber 44 or void. In FIG. 8, the injectable substance chamber 44 is a void. The thermal bank 40*a* can be substantially cylindrical. The injectable substance chamber 44 or void can be substantially cylindrical.

Figure 9:
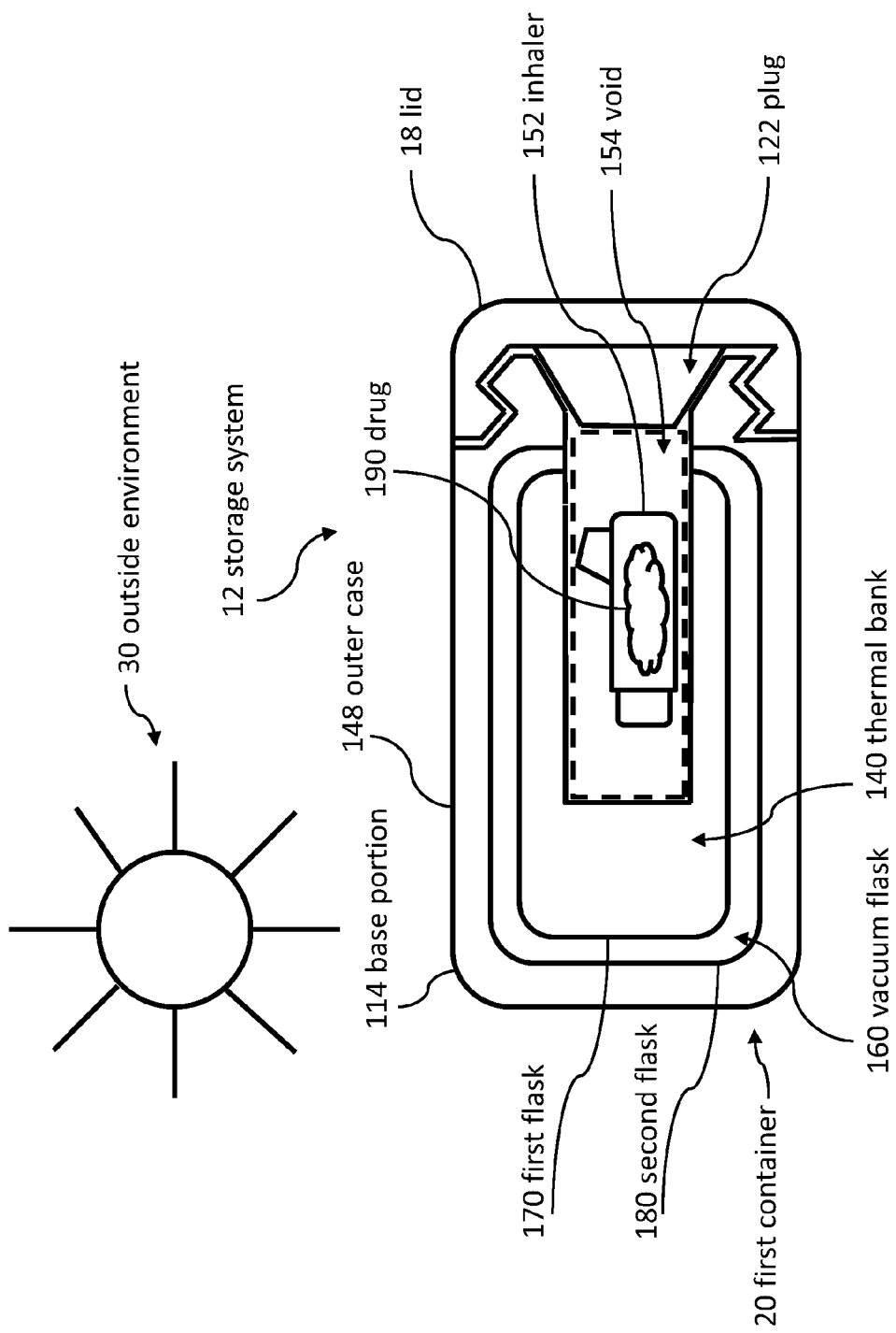
FIG. 9 illustrates a cross-sectional view of an embodiment with an inhaler located inside a storage system, according to some embodiments.

FIG. 9 illustrates an embodiment with an inhaler 152 located, placed, and positioned inside the void 154. An inhaler or puffer is a medical device typically used for delivering medicine into the body via the lungs. Inhalers are commonly used to treat asthma and chronic obstructive pulmonary disease.

In some embodiments, storage systems do not use battery power and/or electricity. While some embodiments use electrical power, several embodiments do not use electrical power and/or do not use electrical power to control or alter the temperature inside the storage system 12.

In some embodiments, storage systems are substantially cylindrical. For example, the storage system 12 in FIG. 9 is substantially cylindrical.

Some methods of storing an injectable substance include obtaining a storage system configured to store an injectable substance, wherein the storage system comprises a thermal bank located inside an insulated cover. Several methods include maintaining the thermal bank in a first environment with a temperature of at least 60 degrees Fahrenheit and placing an injectable substance inside the storage system while the thermal bank has a temperature of at least 60 degrees Fahrenheit. Some methods include moving the storage system with the injectable substance located inside to a second environment with a temperature of less than 60 degrees Fahrenheit and moving the storage system to a third environment with a temperature of more than 60 degrees before the temperature of the thermal bank is less than 60 degrees Fahrenheit. Some embodiments are similar to the above embodiment except 60 degrees Fahrenheit is replaced with 65 degrees Fahrenheit, 55 degrees Fahrenheit, or 50 degrees Fahrenheit.

Several methods include maintaining the thermal bank in a first environment with a temperature of at least 60 degrees Fahrenheit and less than 85 degrees Fahrenheit and placing an injectable substance inside the storage system while the thermal bank has a temperature of at least 60 degrees Fahrenheit and less than 85 degrees Fahrenheit. Some methods include maintaining the thermal bank in a first environment with a temperature of at least 65 degrees Fahrenheit and less than 80 degrees Fahrenheit and placing an injectable substance inside the storage system while the thermal bank has a temperature of at least 65 degrees Fahrenheit and less than 80 degrees Fahrenheit.

Several method embodiments include obtaining a storage system with an internal chamber such as an injectable substance chamber wherein the internal chamber has a temperature and the storage system is configured not to use electricity, electrical power, or batteries to alter the temperature of the internal chamber. In some embodiments, the storage system is configured not to use electricity, electrical power, electrical power cords, or batteries.

Some method embodiments include placing or maintaining the storage system in a first environment, which has a temperature within a first temperature range, for a first period of time. In some embodiments, the first environment can be indoors, approximately 77 degrees Fahrenheit, approximately 74 degrees Fahrenheit, approximately room temperature, and/or another temperature or temperature range listed herein. In some embodiments, he first temperature range can be approximately room temperature; at least 70 degrees Fahrenheit and/or less than 80 degrees Fahrenheit; at least 65 degrees Fahrenheit and/or less than 85 degrees Fahrenheit; equal to or greater than about 59 degrees Fahrenheit and/or less than or equal to 86 degrees Fahrenheit; or at least 55 degrees Fahrenheit and/or less than or equal to 90 degrees Fahrenheit. The first period of time can be the time necessary for the temperature of the storage system, thermal bank, and/or internal chamber to reach a temperature that is within any one of the ranges listed above and/or within the first temperature range. Some method embodiments include placing or maintaining the storage system in the first environment until heat transfer between the first environment and the storage system causes the temperature of the storage system to be within any one of the ranges listed above and/or within the first temperature range.

Some method embodiments include placing a medicinal drug, an injectable substance, an injection device, an inhaler, and/or a pharmaceutical substance inside the storage system while the storage system has a temperature within any one of the ranges listed above and/or within the first temperature range. The temperature of the storage system can be defined by the temperature of the thermal bank, the weighted average temperature of the storage system (where the temperature of each material is weighted by the heat capacity of the material), or any other suitable method.

Several method embodiments include closing a lid of the storage system while the storage system is located in the first environment with the first temperature such that the storage system surrounds the medicinal drug, injectable substance, injection device, inhaler, and/or pharmaceutical substance located inside the storage system.

Some method embodiments include removing the storage system from the first environment and transporting the storage system towards a second environment while the storage system has a temperature within the first temperature range. In other words, in some embodiments, the storage system does not have cold packs (such as ice) or heat packs (such as chemical hand warmers) located inside the storage system. For example, in some embodiments, the storage system can have a weighted average temperature of approximately room temperature when the storage system is removed from the first environment and transported towards the second environment.

Several method embodiments include moving the storage system to a second environment with a second temperature range for a second period of time. In some embodiments, the second temperature range comprises all temperatures except for the temperatures within the first temperature range. In some embodiments, the second temperature range is less than the first temperature range and/or greater than the first temperature range. In some embodiments, the second temperature range is less than room temperature and/or greater than room temperature; less than 70 degrees Fahrenheit and/or greater than 80 degrees Fahrenheit; less than 65 degrees Fahrenheit and/or greater than 85 degrees Fahrenheit; less than 59 degrees Fahrenheit and/or greater than 86 degrees Fahrenheit; less than 55 degrees Fahrenheit and/or greater than 90 degrees Fahrenheit; or less than 32 degrees Fahrenheit and/or greater than 100 degrees Fahrenheit.

The second period of time can be a time during which the temperature of the internal chamber stays within the first temperature range. Some method embodiments include maintaining the storage system in the second environment while the temperature of the internal chamber stays within the first temperature range. Some method embodiments include moving the storage system from the second environment to a third environment before the temperature of the internal chamber deviates outside of the first temperature range. Some method embodiments include moving the storage system from the second environment to the third environment before the temperature of the internal chamber changes to a temperature outside of the first temperature range. Is some embodiments, the temperature of the third environment is equal to any of the temperatures and/or temperature ranges described above for the first environment. The temperature of the third environment can be different than the temperature of the first environment. In some embodiments, the third environment is the first environment such that the storage system is moved from the first environment to the second environment and then back to the first environment. Some embodiments include removing and/or at least partially opening the lid after the storage system is returned to the first environment and/or moved to the third environment.

Some embodiments include maintaining the storage system at approximately room temperature; placing a substance inside the storage system; moving the storage system to an environment that is hotter or colder than room temperature while the storage system has an internal temperature of approximately room temperature and/or a temperature within a suitable range; and then returning the storage system to approximately room temperature before the internal temperature deviates outside of a suitable range. The suitable range can be the storage temperature range recommended by the manufacturer of the substance and/or a temperature range recommended and/or approved by the manufacturer of the substance for temporary temperature excursions. Some embodiments include returning the storage system to approximately room temperature before the recommended and/or approved time of the temporary temperature excursion expires.

Several embodiments of a method of storing a medicinal injectable substance include obtaining an outer case and a lid. Some embodiments include placing a vacuum flask inside at least a portion of the outer case. Placing a vacuum flask inside at least a portion of the outer case can include placing an outer case around at least a portion of a vacuum flask. Some embodiments include placing a thermal bank with a heat capacity of at least 400 J/K inside the vacuum flask. Several embodiments include placing an injection device inside the vacuum flask, wherein the injection device is at least partially filled with the medicinal injectable substance. Some embodiments include coupling the lid to the outer case such that the outer case and the lid surround the injection device.

Referring now to FIG. 9, the thermal bank 140 can be a phase change system having multiple phase change materials. The multiple phase change materials can provide protection from temperatures above and below room temperatures. Thus, one system can shield medicine from temperature variations in both directions without requiring previous knowledge of whether a person will bring the storage system into hot or cold weather.

One way to build a thermal bank 140 that resists temperature decreases and increases is to include two phase change materials inside the thermal bank. The first phase change material can resist temperature decreases due to cold outside environments. The second phase change material can resist temperature increases due to hot outside environments.

The first phase change material can have a high heat of fusion to enable a relatively lightweight system that can still provide sufficient resistance to temperature changes. The first phase change material can release large amounts of heat before allowing the temperature inside the first chamber to decrease. For example, the first phase change material can release large amounts of heat (per gram of the material) as the material changes from a liquid to a solid. The melting temperature of the first phase change material can be less than 70 Fahrenheit (e.g., just below room temperature) and greater than the minimum recommended medicine storage temperature.

For example, if a manufacturer of a medicine recommends a minimum storage temperature of 45 degrees Fahrenheit, then the first phase change material can be selected with a melting temperature between 45 degrees Fahrenheit and around 70 degrees Fahrenheit (e.g., below a room temperature). Thus, when a temperature inside the insulated container goes below the melting point, the first phase change material releases large amounts of heat before allowing the temperature inside the first chamber to significantly decrease. As a result, the first phase change material dramatically prolongs the time required to decrease the temperature inside the first chamber below the minimum storage temperature.

This additional time can enable the medicine to remain outside much longer without reducing the efficacy of the medicine than would be the case without the storage system. Moreover, the phase change enables the storage system to much more compact than would be the case with a thermal bank 140 that only uses water to resist temperature changes (at temperatures above 32 degrees Fahrenheit).

The second phase change material of the thermal bank 140 can resist temperature increases due to hot outside environments. The second phase change material can have a high heat of fusion and a melting temperature that is greater than room temperature and less than the maximum recommended medicine storage temperature. For example, if the maximum recommended storage temperature is 85 degrees Fahrenheit, then in some embodiments, the second phase change material can have a melting temperature between 80 degrees Fahrenheit and 85 degrees Fahrenheit. Thus, the second phase change material can absorb a large amount of heat (to melt) before the second phase change material would allow the temperature inside the storage system 12 to increase significantly above the melting temperature of the second phase change material.

The rate of heat transfer between the outside environment 30 and the first chamber (e.g., the void 154) is reduced by reducing the temperature difference between the outside environment and the thermal bank 140 (during melting or solidifying). Thus, phase change materials can be selected that have a melting point near the minimum storage temperature (e.g., without being less than the minimum storage temperature) or near the maximum storage temperature (e.g., without being greater than the maximum storage temperature). (The minimum and maximum storage temperatures can be recommended by the manufacturer of the medicine and are often included with literature provided with the medicine.) "Near the minimum" or "near the maximum" can be within 10 degrees Fahrenheit.

Many different materials can be suitable phase change materials as long as the materials have a melting temperature within the target range (as explained above). Entropy Solutions, Inc. has an office in Plymouth, Minn. and provides a wide range of suitable phase change materials under the brand name PureTemp. Climator Sweden AB sells a wide range of phase change materials under the brand name ClimSel. Examples of phase change materials include sodium sulfate, trimethylolethane combined with water, $Mn(NO_3)_2*6H_2O+MnCl_2*4H_2O$, $NaCl*Na_2SO_4*10H_2O$, paraffin 16-carbons, and paraffin 18-carbons.

In several embodiments, phase change materials spontaneously melt and/or solidify in response to temperature (without requiring an additional activation step). For example, just a drop in temperature below a melting temperature can cause a spontaneous phase change material to freeze. Just a rise in temperature above a melting temperature can cause a spontaneous phase change material to solidify.

The phase change materials are not the only part of the system that reduces the rate of temperature change inside the first chamber (e.g., the void 154). An insulated container can reduce the rate of heat transfer. Some embodiments include a vacuum flask. Thermos L.L.C. manufactures a wide range of vacuum flasks.

In several embodiments, the interior of the vacuum flask is cylindrical. The chambers that hold the phase change system plus the first chamber can form a cylindrical shape that is tailored to the interior of the vacuum flask. The phase change system can have a compliant external housing with an outer diameter that is larger than the diameter of an opening to the vacuum flask. The compliant external housing (e.g., a compliant perimeter) can enable pressing the phase change system into the vacuum flask in spite of the outer diameter of the external housing being larger than the diameter of the opening to the vacuum flask.

In several embodiments, storage systems include an insulated container comprising a base and an opening configurable to enable removing a medicine from inside the insulated container; a first chamber located inside the insulated container, wherein the first chamber is configured to hold the medicine; a first phase change material located inside the insulated container; and/or a second phase change material located inside the insulated container.

In some embodiments, the first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. The first melting temperature can be at least four degrees Fahrenheit less than the second melting temperature. For example, 74 degrees Fahrenheit can be approximately equal to a typical room temperature (although room temperatures commonly vary in rooms having temperature controlled environments enabled by heating and/or air conditioning).

Using a "temperature dividing line" of 74 degrees Fahrenheit helps enable some embodiments to avoid inappropriately triggering melting and/or freezing while the storage system is located in a temperature controlled room. Imagine if the second phase change material had a melting temperature of less than 74 degrees. As a result, the second phase change material could completely melt before a person even moved the storage system from a room temperature into a hot environment that is warmer than a maximum recommended storage temperature of the medicine. In this case the phase change of the second phase change material would not help reduce the rate of temperature rise inside the first chamber in response to heat transfer caused by the hot environment. Similarly, this "temperature dividing line" helps ensure that the first phase change material will have a sufficiently low melting temperature such that the first phase change material should not solidify before the storage system is moved from a room temperature to an environment that is colder than a minimum recommended storage temperature.

The "temperature dividing line" can vary based on what medicine the storage system will hold. For example, some medicine manufacturers recommend refrigerating certain medicines. In several embodiments, the temperature dividing line is 36 degrees Fahrenheit. Thus, the first phase change material can have a melting temperature above 0 degrees Fahrenheit and/or below 36 degrees Fahrenheit. The second phase change material can have a melting temperature above 36 degrees Fahrenheit and/or below 50 degrees Fahrenheit.

In some embodiments, the storage system is configured to cause the first phase change material to solidify when a first temperature of the first chamber falls below the first melting temperature, and/or the storage system is configured to cause the second phase change material to melt when the first temperature of the first chamber rises above the second melting temperature. As a result, the storage system can be configured to temporarily protect the medicine from a first environment that is colder than a safe minimum storage temperature and/or from a second environment that is hotter than a safe maximum storage temperature. Manufacturers of medicines can recommend minimum storage temperatures and/or maximum storage temperatures for medicines.

In several embodiments, the first phase change material has a first latent heat of at least 40 kJ/kg, and/or the second phase change material has a second latent heat of at least 40 kJ/kg. In some embodiments, the first phase change material has a first latent heat of at least 110 kJ/kg, and/or the second phase change material has a second latent heat of at least 110 kJ/kg. In several embodiments, the first phase change material has a first latent heat of at least 180 kJ/kg, and/or the second phase change material has a second latent heat of at least 180 kJ/kg. These latent heat properties can dramatically reduce the necessary size of the phase change materials, which enables dramatically reducing the overall volume of the storage system.

Figure 10:
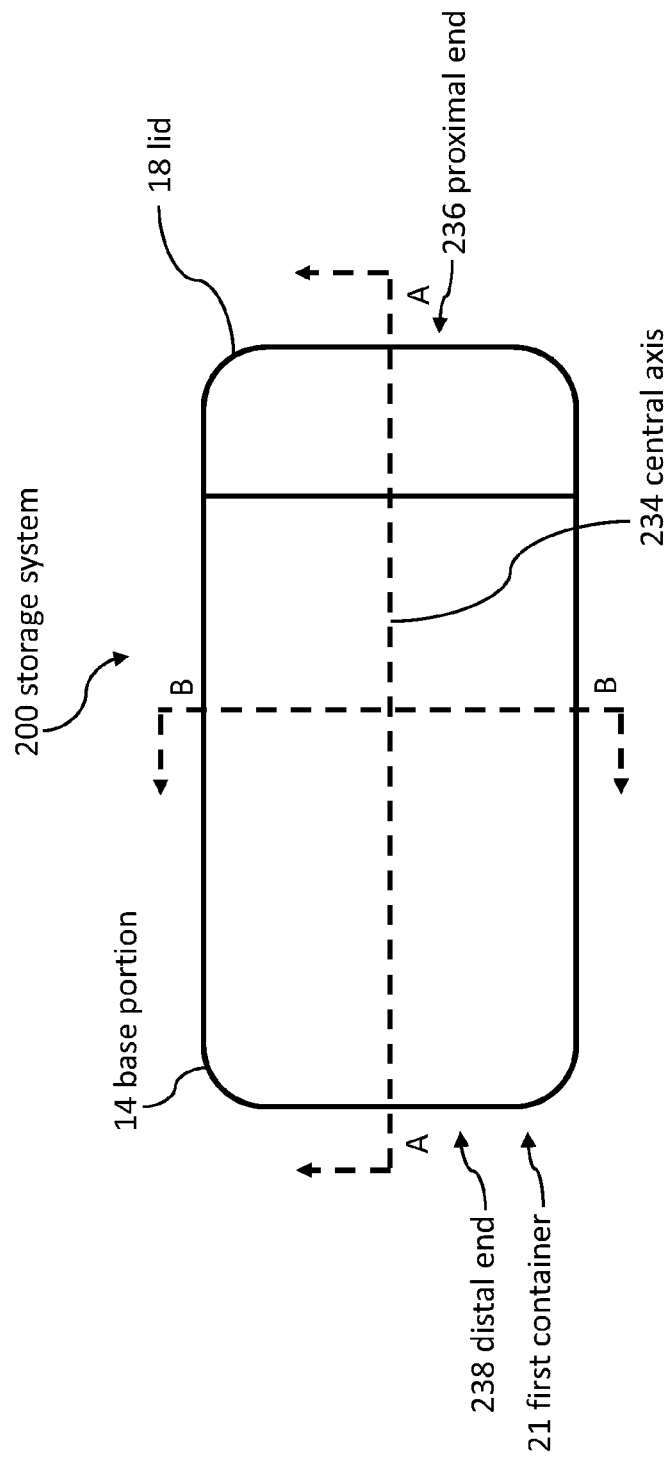
FIG. 10 illustrates a side view of a storage system, according to some embodiments.
Figure 11:
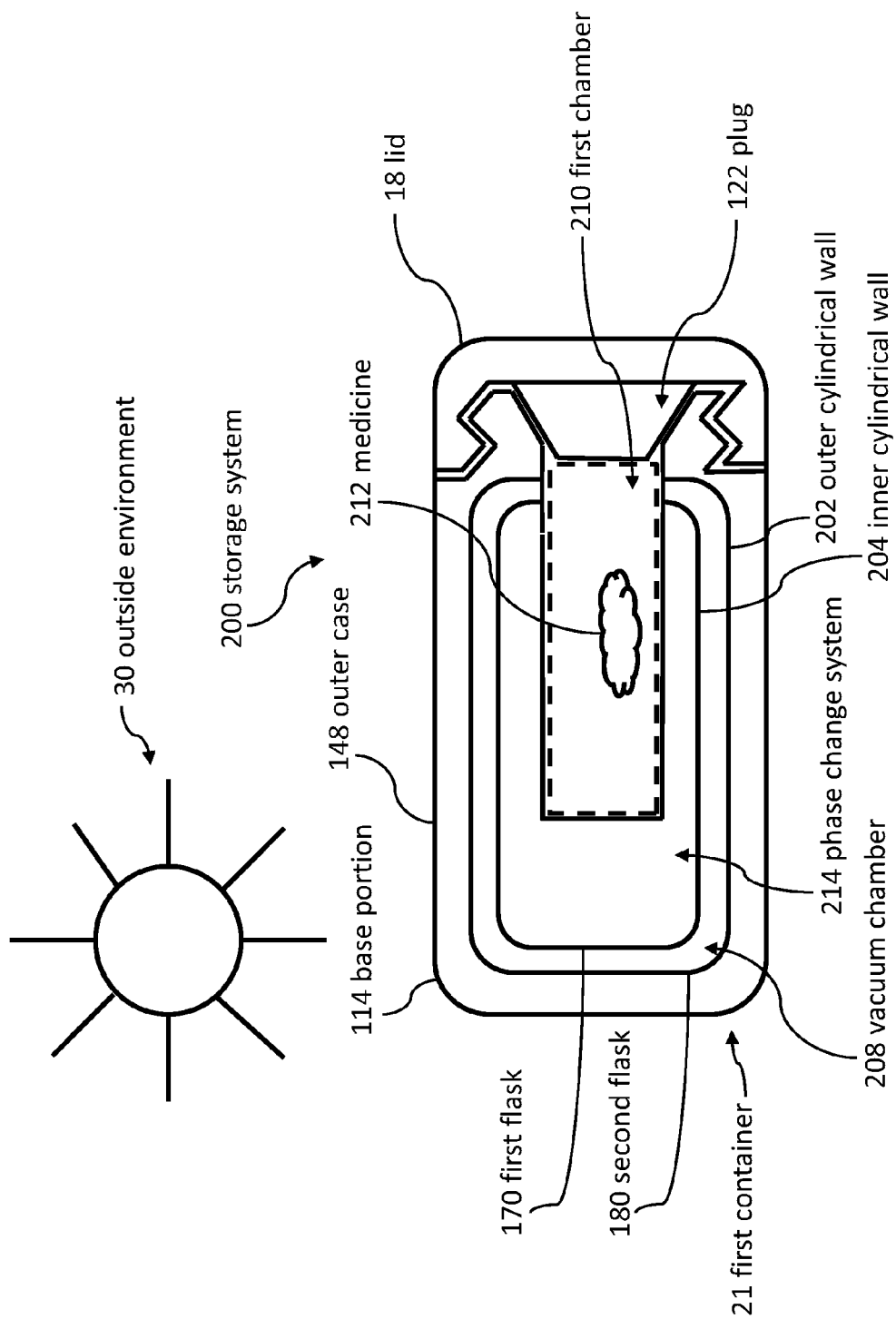
FIG. 11 illustrates a cross-sectional view of a storage system along plane A-A, which extends into the page in FIG. 10, according to some embodiments.

FIG. 10 illustrates a side view of a storage system, according to some embodiments. FIG. 11 illustrates a cross-sectional view of a storage system along plane A-A, which extends into the page in FIG. 10, according to some embodiments. Referring now to FIG. 11, the storage system 200 can include an outer cylindrical wall 202 and an inner cylindrical wall 204 coupled to the outer cylindrical wall 202. Cylindrical walls can be made of thin, rigid metal and can be joined at the proximal end of the base portion 114. A vacuum chamber 208 can be located between the inner cylindrical wall 204 and the outer cylindrical wall 202 to form a vacuum flask 160 (labeled in FIG. 9).

A first chamber 210 is at least partially surrounded by the inner cylindrical wall 204. As used herein, "surrounded" means that an object wraps 360 degrees around another object. "Surrounded" does not necessarily mean an object completely encloses another object in all directions. For example, as illustrated in FIG. 11, the inner cylindrical wall 204 surrounds the first chamber even though the first chamber 210 has an opening that is covered by the lid 18. The first chamber 210 can hold a medicine 212 such as an inhaler or an injection device such as an EpiPen.

Figure 12:
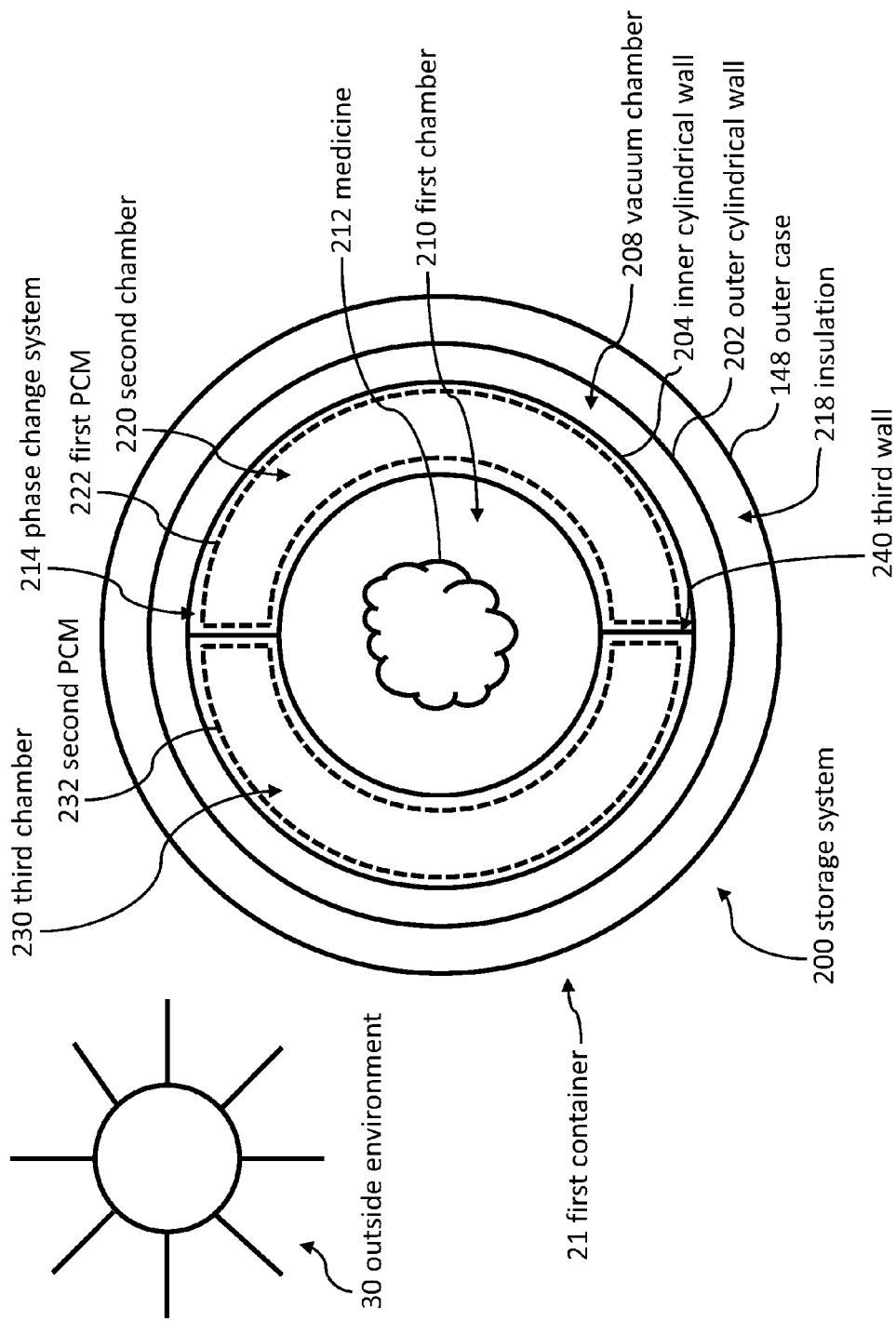
FIG. 12 illustrates a cross-sectional view along line B-B from FIG. 10, according to some embodiments.

In FIG. 11, the thermal bank is a phase change system 214. In the interest of clarity, FIG. 11 does not illustrate various details regarding the phase change system 214. Additional details regarding the phase change system 214 are shown in FIG. 12, which illustrates a cross-sectional view along line B-B from FIG. 10.

Several embodiments do not include an outer case 148, which can include insulation 218. The outer case 148 can be cylindrical.

The phase change system 214 can include a second chamber 220 having a first phase change material 222 and can include a third chamber 230 having a second phase change material 232. The phase change system 214 is at least partially surrounded by the inner cylindrical wall 204. The storage system 200 has a central axis 234 that runs from a proximal end 236 of the storage system 200 to a distal end 238 of the storage system 200 (shown in FIG. 10). A third wall 240 passes through the central axis 234 to separate the second chamber 220 from the third chamber 230. The third wall 240 separates a left half of the phase change system 214 (e.g., the third chamber 230) from a right half of the phase change system 214 (e.g., the second chamber 220). The central axis 234 is located in a plane, and the third wall 240 is located in the same plane.

The first phase change material 222 can have a first melting temperature greater than 40 degrees Fahrenheit and less than 74 degrees Fahrenheit. The second phase change material 232 can have a second melting temperature greater than 74 degrees Fahrenheit and less than 100 degrees Fahrenheit. Several embodiments include different melting temperatures.

Figure 13:
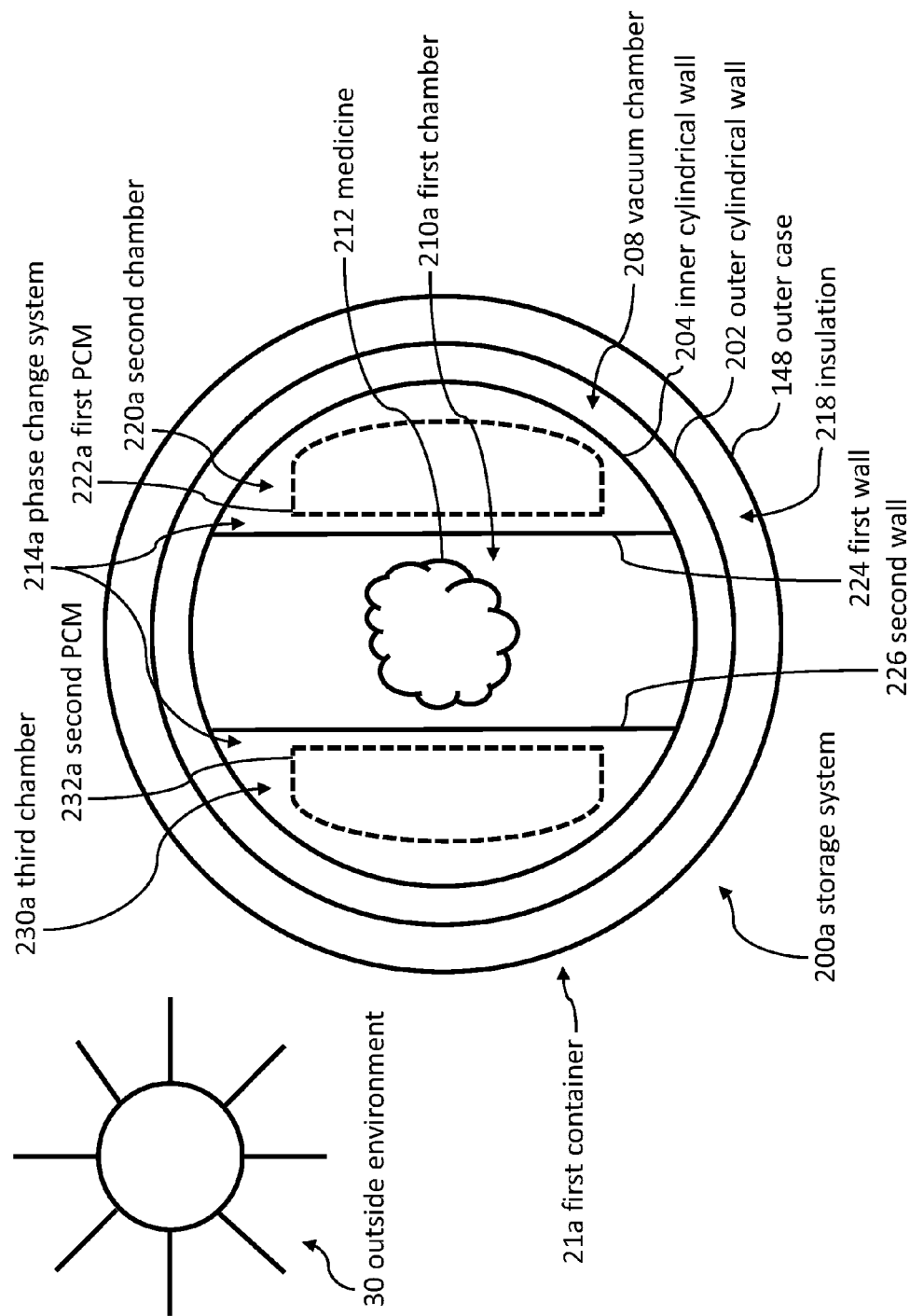
FIG. 13 illustrates a cross-sectional view of a storage system shown from the same perspective as FIG. 12, according to some embodiments.

FIG. 13 illustrates a cross-sectional view of a storage system 200a shown from the same perspective as FIG. 12. The storage system 200a includes a side view and cross-sectional view that look like the side view and cross-sectional view shown in FIGS. 10 and 11.

Referring now to FIG. 13, at least a majority of the first chamber 210a is located between a first wall 224 and a second wall 226 that are located within the inner cylindrical wall 204. The first wall 224 extends across an interior portion from one side of the inner cylindrical wall 204 to another side of the inner cylindrical wall 204. (The first wall 224 is not embedded in the inner cylindrical wall 204.) The first wall 224 separates the first chamber 210a from a first side of the phase change system 214a. The second wall 226 separates the first chamber 210a from a second side of the phase change system 214a.

The first wall 224 separates the first chamber 210a from the second chamber 220a that has the first phase change material 222a. The second wall 226 separates the first chamber 210a from the third chamber 230a that has the second phase change material 232a. The first chamber 210a, the second chamber 220a, and the third chamber 230a extend distally parallel relative to each other (e.g., into the page in FIG. 13). The first chamber 210a and the phase change system 214a form a cylindrical shape.

The first wall 224 and second wall 226 can be rigid or compliant. Rigid walls can be rigid plastic or metal. Compliant walls can be made from plastic or rubber configured to bend without breaking to conform to many different shapes. In some embodiments, the first wall 224 and second wall 226 are compliant so they can move radially outward such that a width between the first wall 224 and second wall 226 expands to enlarge the first chamber 210a.

Figure 14:
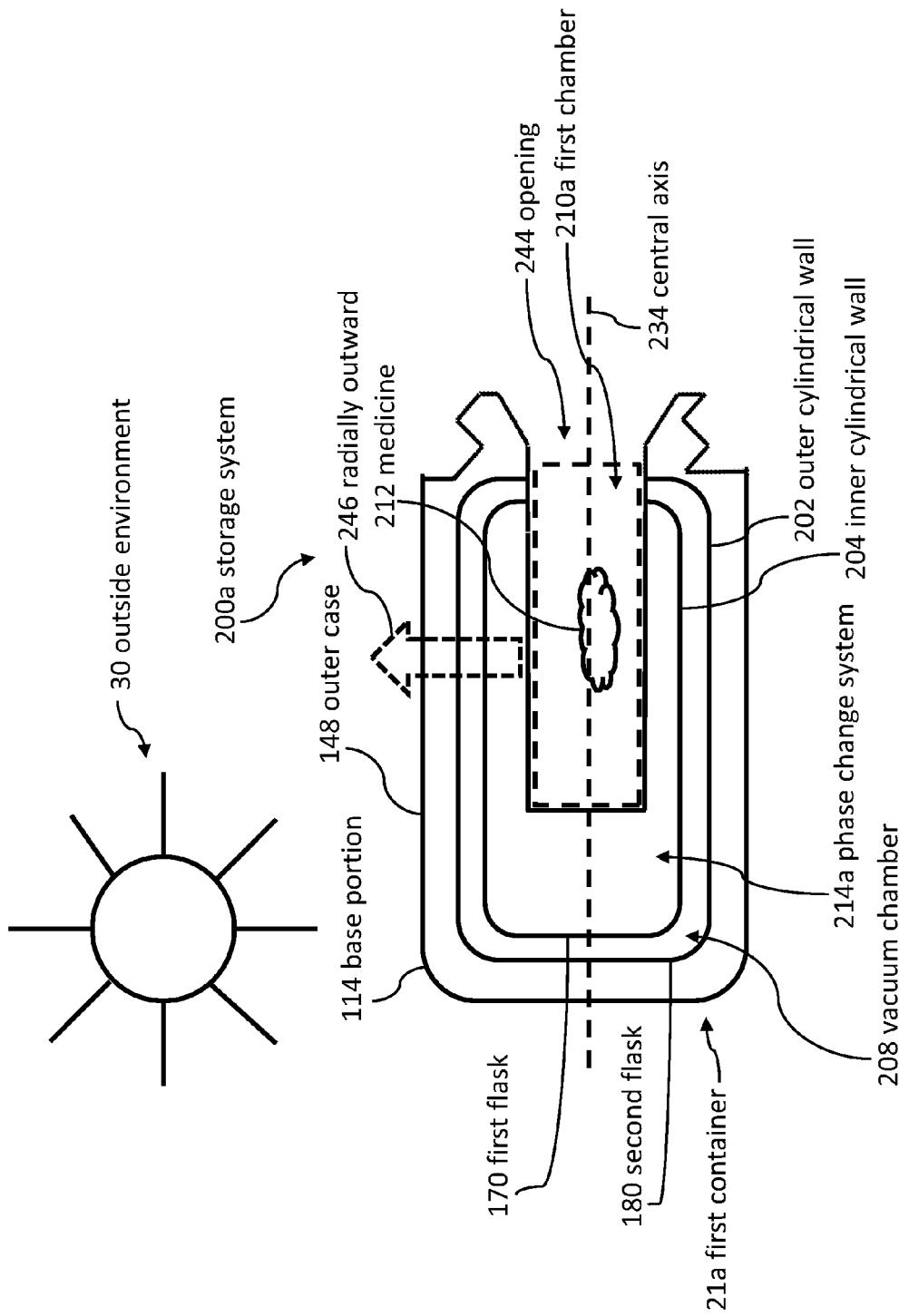
FIG. 14 illustrates the storage system from FIG. 13 along a cross section that is perpendicular to the cross section shown in FIG. 13, according to some embodiments.

FIG. 14 illustrates the storage system 200a from FIG. 13 along a cross section that is perpendicular to the cross section shown in FIG. 13. The lid 18 (shown in FIG. 11) was removed. The opening 244 is coupled to the first chamber 210a such that the opening 244 provides access to the first chamber 210a to enable removing the medicine 212 from the insulated container (e.g., the storage system 200a). When the opening 244 is unsealed, a person can reach into the opening 244 to grab the medicine 212 in the first chamber 210a.

Referring now to FIG. 13, the first chamber 210a has a longest dimension (into the page). The second chamber 220a has a longest dimension (also into the page). The first chamber 210a and the second chamber 220a are oriented such that the longest dimension of the first chamber 210a and the longest dimension of the second chamber 220a both point towards the same exterior side of the storage system, which in the illustrated embodiment is the distal end (e.g., 238 in FIG. 10). When the longest dimension of the first chamber 210a and the longest dimension of the second chamber 220a both point towards the same exterior side of the storage system 200a, a portion of the first chamber 210a and at least a portion of the second chamber 220a run approximately alongside each other (e.g., even though a wall 224 separates the first chamber 210a from the second chamber 220a). The first chamber 210a, the second chamber 220a, and the third chamber 230a are oriented such that they extend distally in a first direction away from the opening 244 (shown in FIG. 14).

Referring now to FIGS. 13 and 14, the insulated container comprises a central axis 234. The first chamber 210a extends distally away from the opening 244 such that at least a majority of the central axis 234 is located inside the first chamber 210a.

The second chamber 220a and the third chamber 230a are located outside of the first chamber 210a and are located radially outward 246 from the central axis 234. (The arrow illustrated in FIG. 14 is just one example of a direction that is radially outward relative to the central axis 234.)

Figure 15:
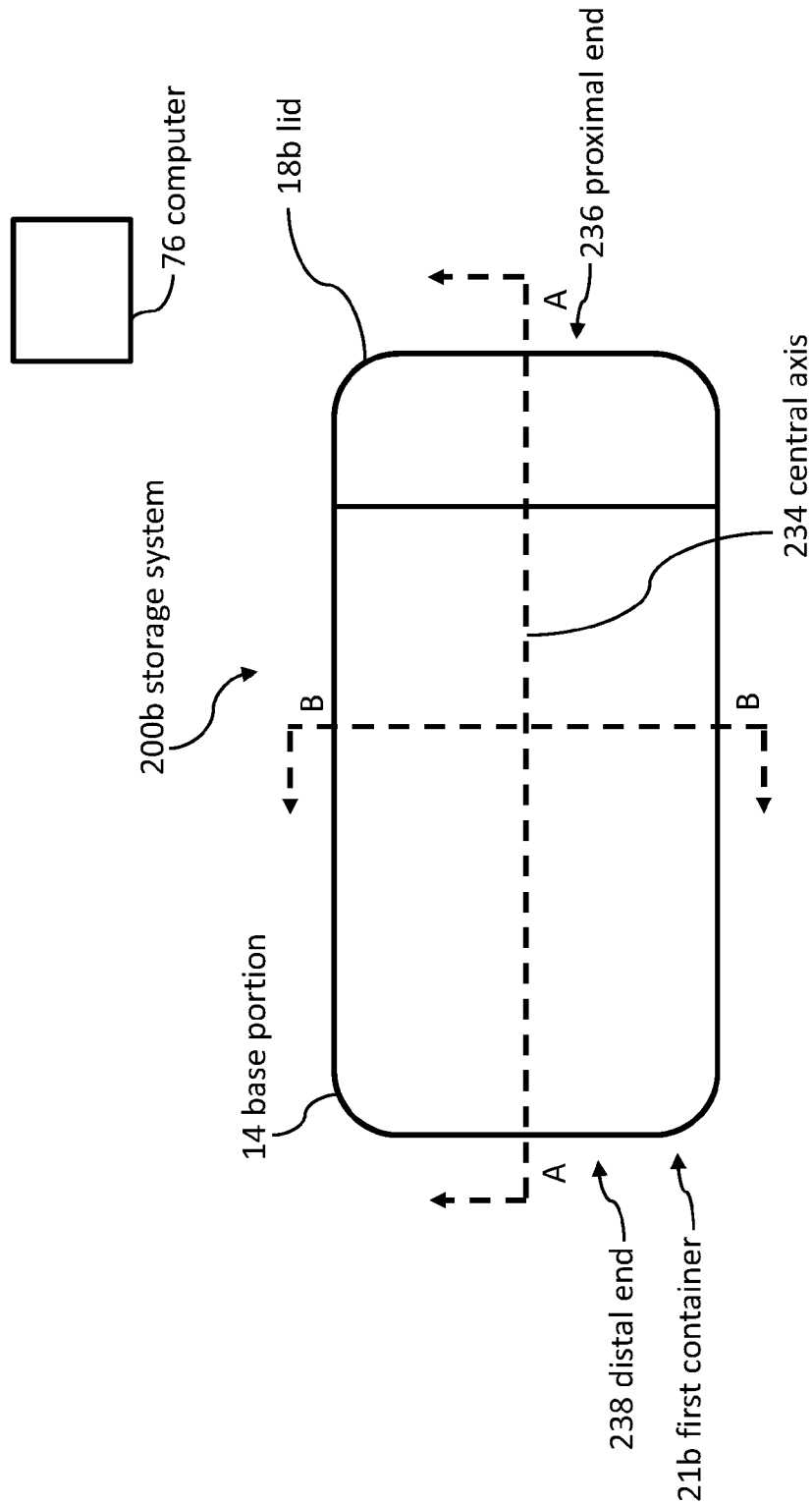
FIG. 15 illustrates a side view of a storage system, according to some embodiments.

FIG. 15 illustrates a side view of a storage system 200b. The lid 18b can include thermometers 68, 88, a temperature display 62b, a communication system 70, a vent 84, a temperature probe 64b, a speaker 24, seals 66, and a control system 86 (as shown in FIG. 5). Thus, the lid 18b can enable a storage system to communicate with the computer 76.

Figure 16:
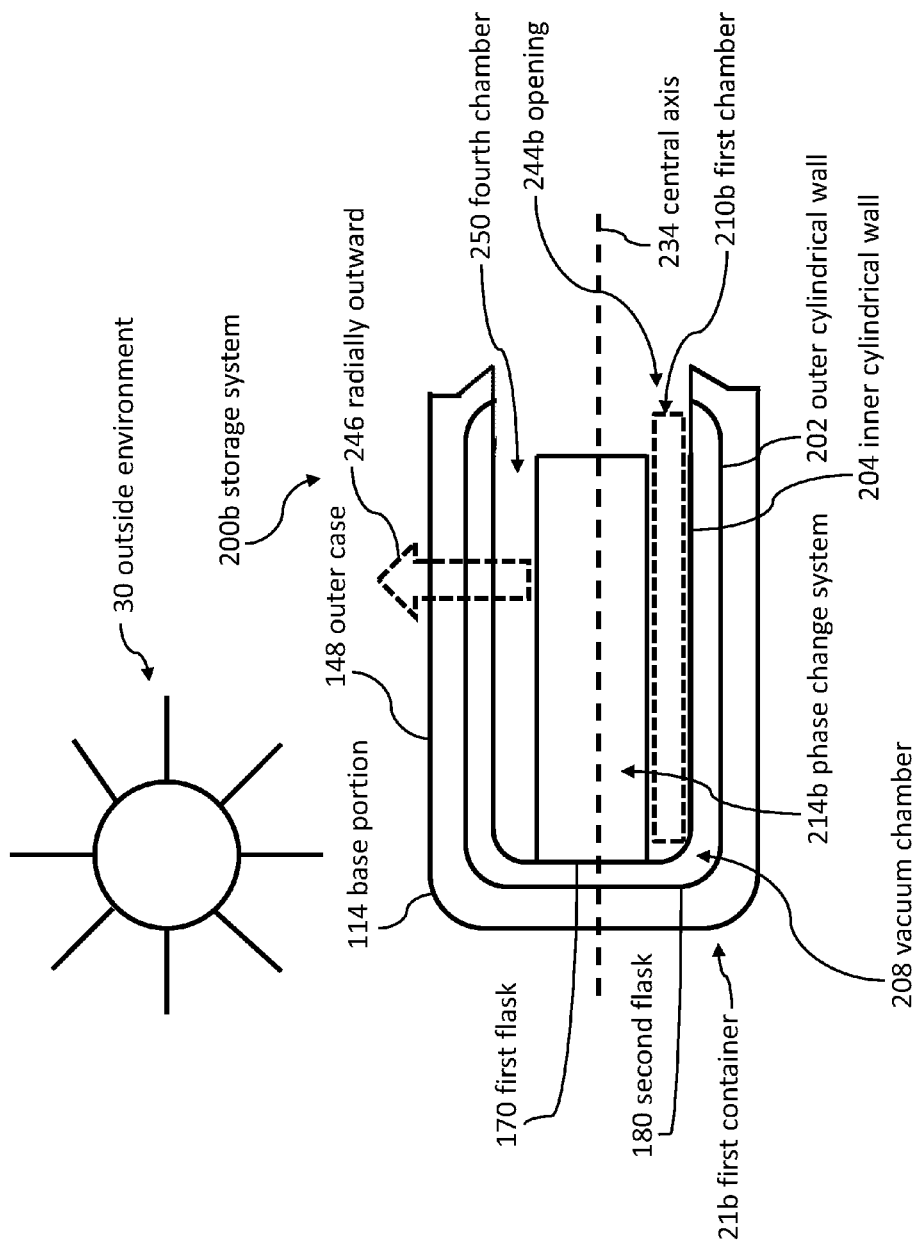
FIG. 16 illustrates a cross-sectional view of the storage system along line A-A from FIG. 15, according to some embodiments.
Figure 17:
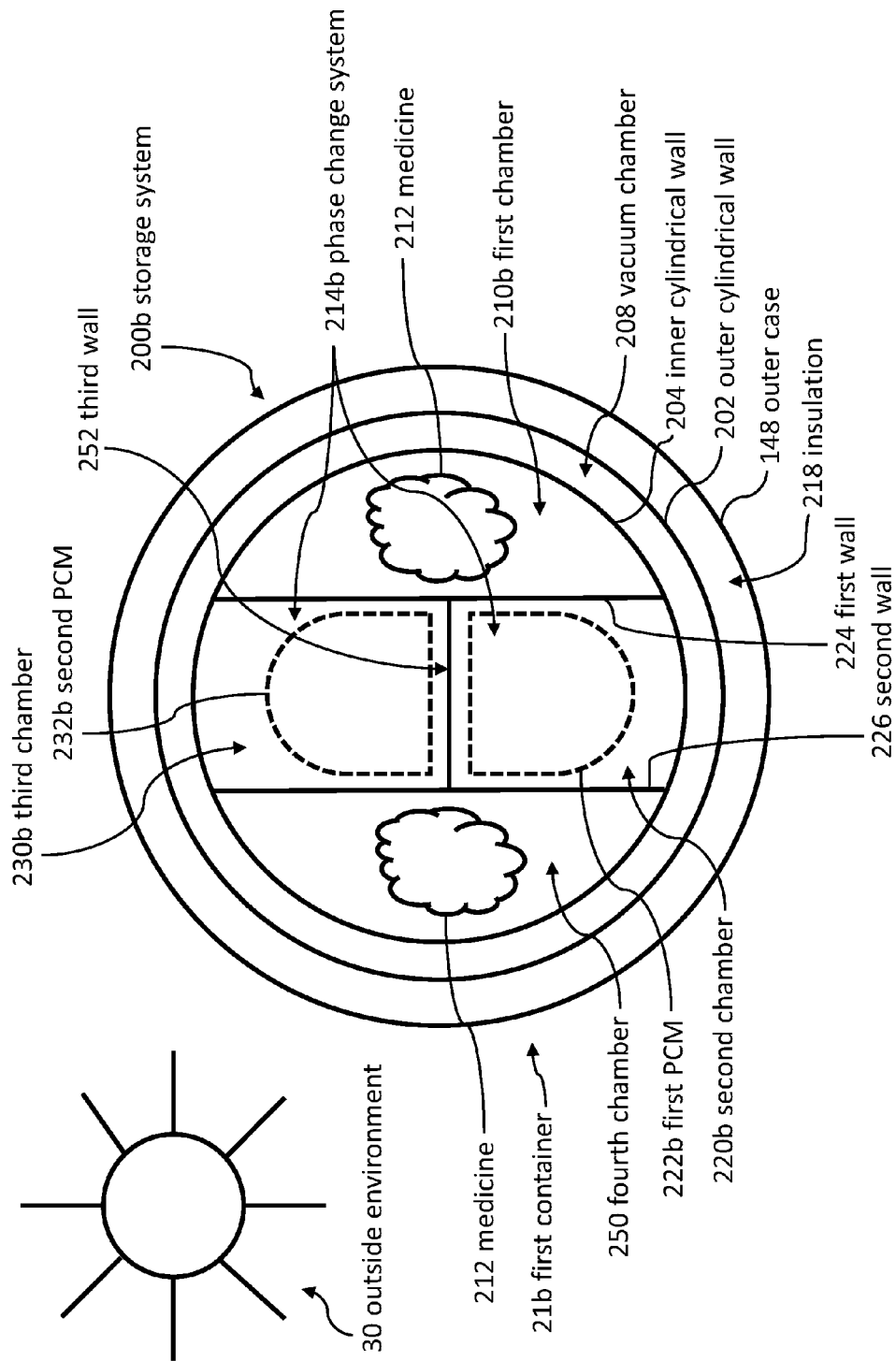
FIG. 17 illustrates a cross-sectional view of the storage system along line B-B from FIG. 15, according to some embodiments.

FIG. 16 illustrates a cross-sectional view of the storage system 200b along line A-A from FIG. 15. The lid 18b is hidden in FIG. 16, but is shown in FIG. 15. FIG. 17 illustrates a cross-sectional view of the storage system 200b along line B-B from FIG. 15.

Referring now to FIGS. 16 and 17, the phase change system 214b is located in center portion of the area located within the inner cylindrical wall 204. A first chamber 210b and a fourth chamber 250 are configured to hold medicine 212. The first chamber 210b and the fourth chamber 250 are located radially outward from the phase change system 214b. A first wall 224 and a second wall 226 separate the phase change system 214b from the first chamber 210b and the fourth chamber 250. The first chamber 210b is located radially outward from the central axis 234 (shown in FIG. 15) on a first side of the phase change system 214b. The fourth chamber 250 is located radially outward from the central axis 234 on a second side of the phase change system 214b.

Various chambers hold phase change materials. Several embodiments include 2, 4, 10, or more chambers to hold various phase change materials, which can have many different melting temperatures. As illustrated in FIG. 17, a second chamber 220b holds a first phase change material 220b. A third chamber 230b holds a second phase change material 232b.

The phase change system 214b is located in a central portion of the storage system such that at least a majority of the central axis 234 (shown in FIG. 15) is located inside the phase change system 214b. A first wall 224 separates the first chamber 214b from the phase change system 214b. A second wall 226 separates the phase change system 214b from the fourth chamber 250, which can be configured to hold an injection device. A third wall 252 passes through the central axis 234 to separate the second chamber 220b from the third chamber 230b.

Referring now to FIGS. 15 and 16, the storage system 200b has a removable lid 18b coupled to an opening 244b of the first chamber 210b such that removing the lid 18b facilitates accessing both the first chamber 210b and the fourth chamber 250 to remove an injection device from the fourth chamber 250.

Figure 18:
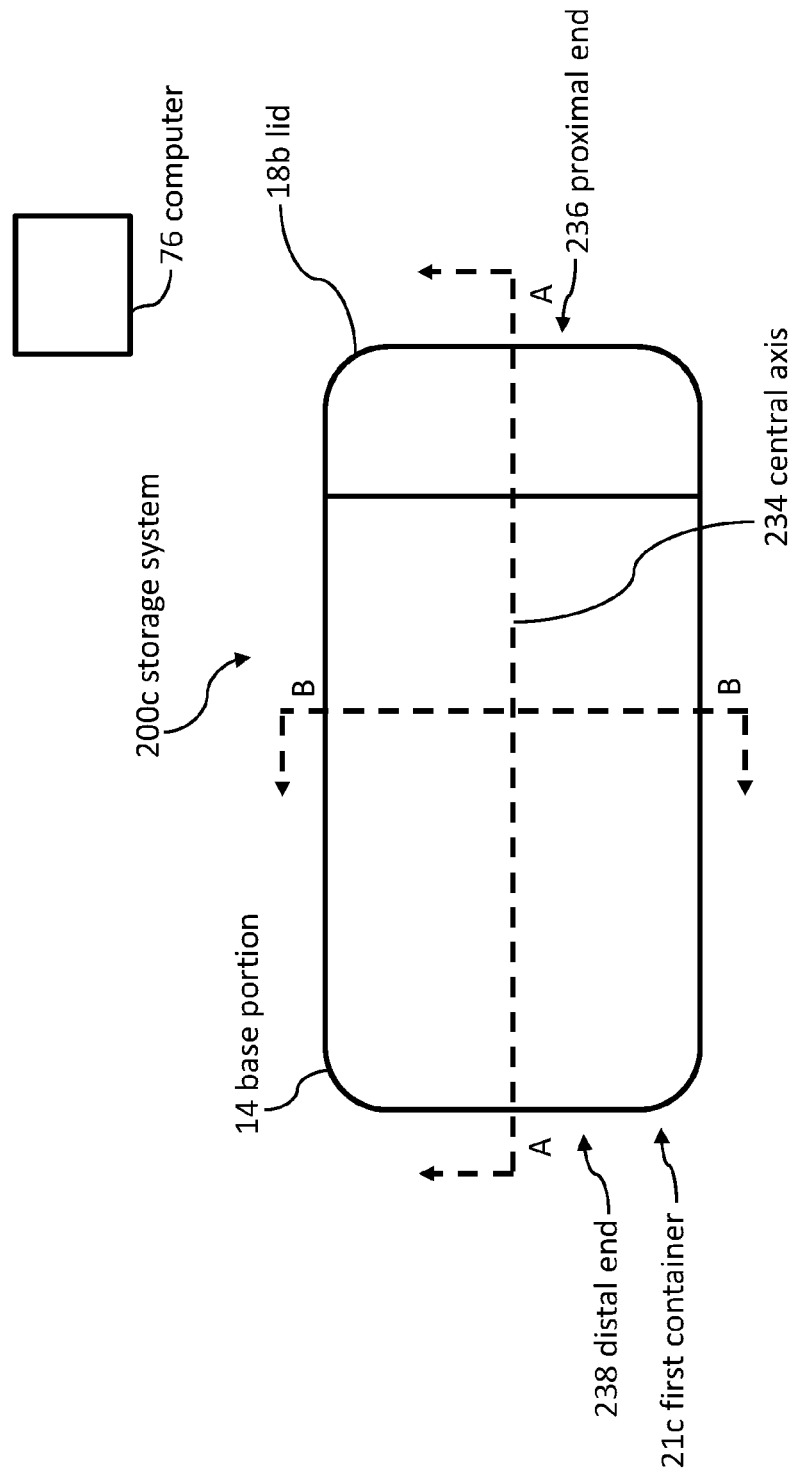
FIG. 18 illustrates a side view of a storage system, according to some embodiments.
Figure 19:
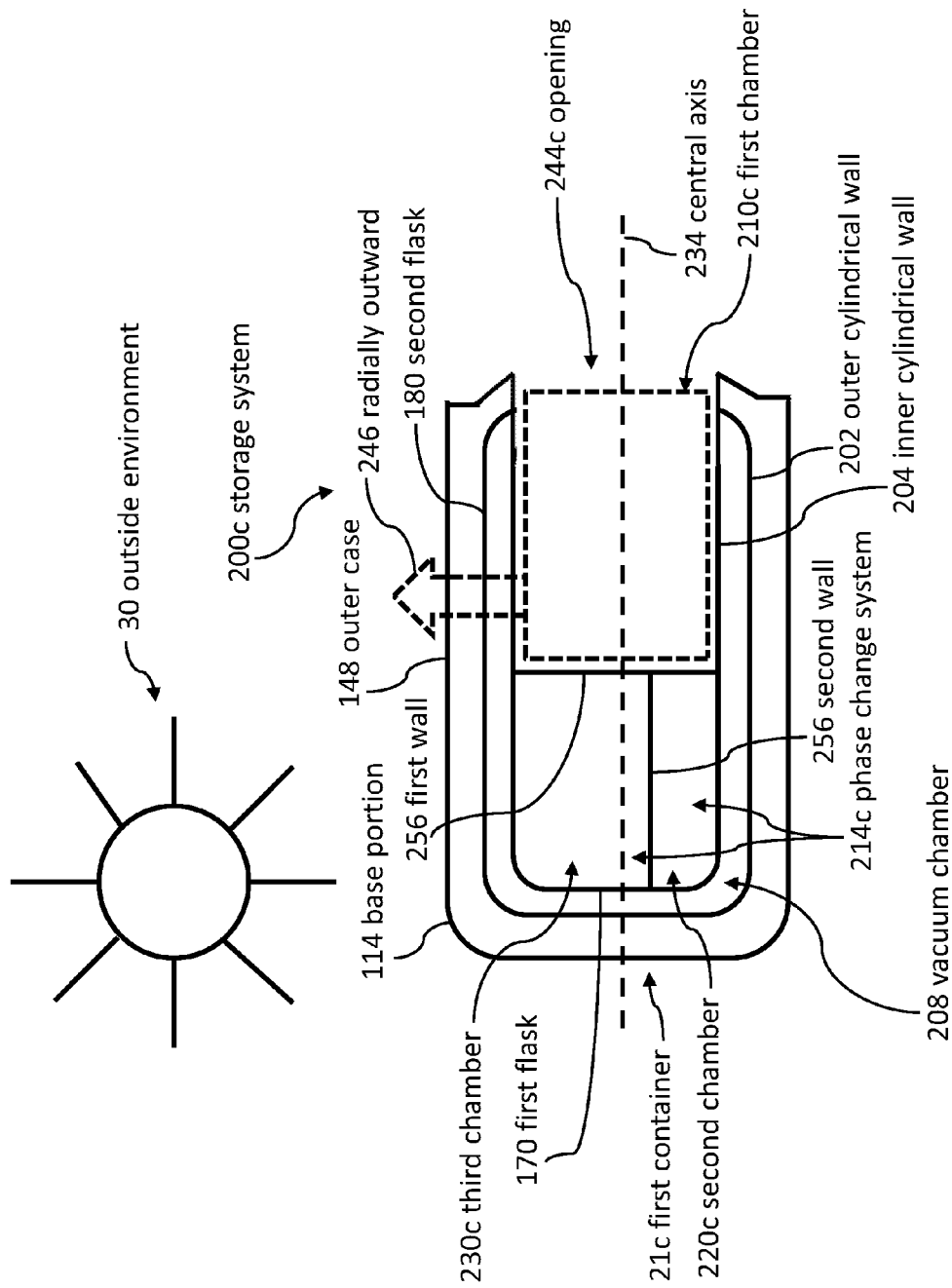
FIG. 19 illustrates a cross-sectional view of the storage system along line A-A from FIG. 18, according to some embodiments.

FIG. 18 illustrates a side view of a storage system 200c. FIG. 19 illustrates a cross-sectional view of the storage system 200c along line A-A from FIG. 18. The lid 18b is hidden in FIG. 19, but is shown in FIG. 18. The storage system 200c comprises a central axis 234. The first chamber 210c extends distally away from an opening 244c of the first chamber 210c such that at least a portion of the central axis 234 is located inside the first chamber 210c. The phase change system 214c is located distally relative to the first chamber 210c.

The storage system 200c has a first wall 256 that is located distally relative to the first chamber 210c. The first wall 256 is located between the first chamber 210c and the phase change system 214c. The phase change system 214c comprises a second wall 258 located between the second chamber 220c and the third chamber 230c of the phase change system 214c. The second wall 258 can be perpendicular to the first wall 256.

Figure 20:
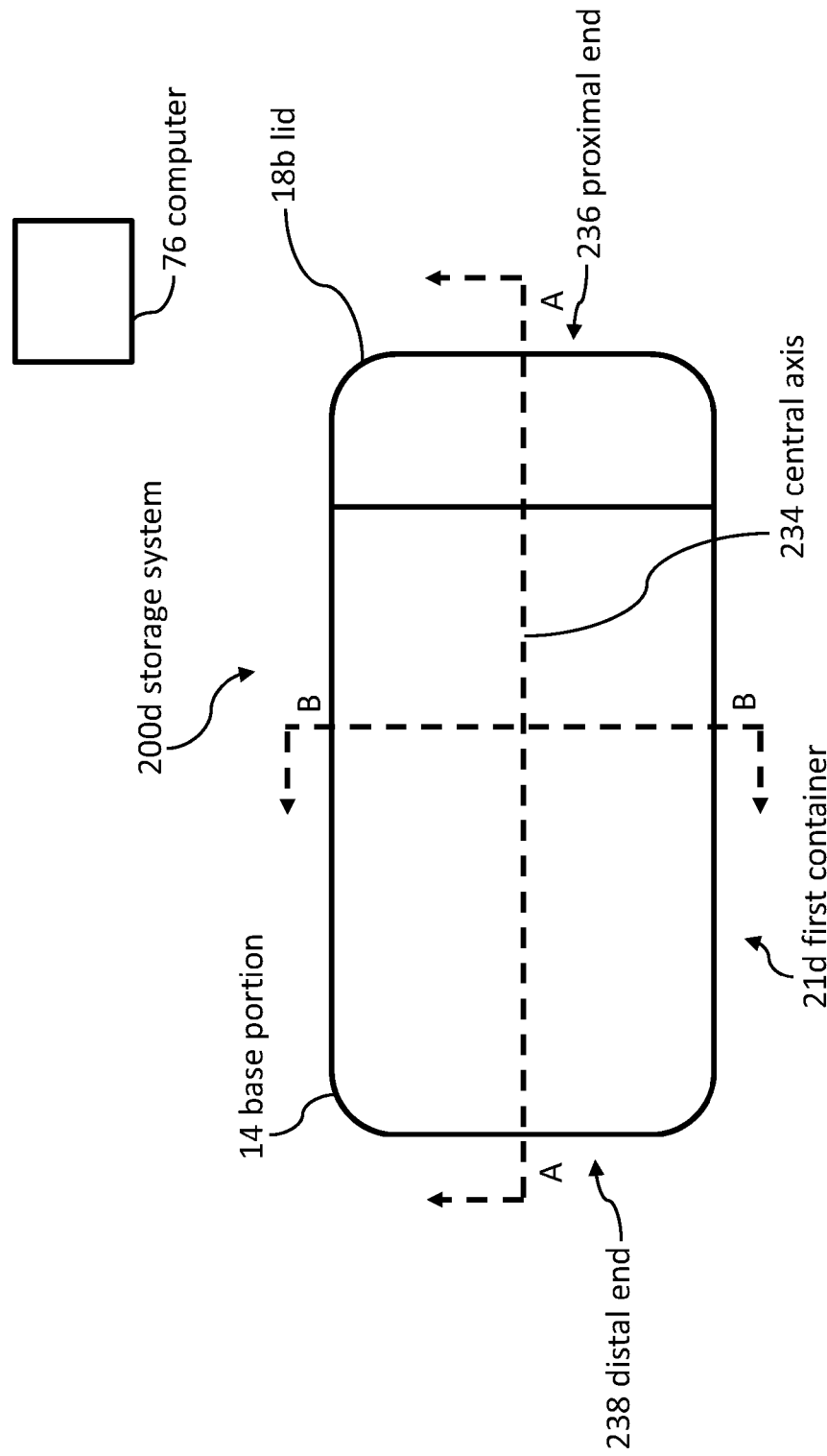
FIG. 20 illustrates a side view of a storage system, according to some embodiments.
Figure 21:
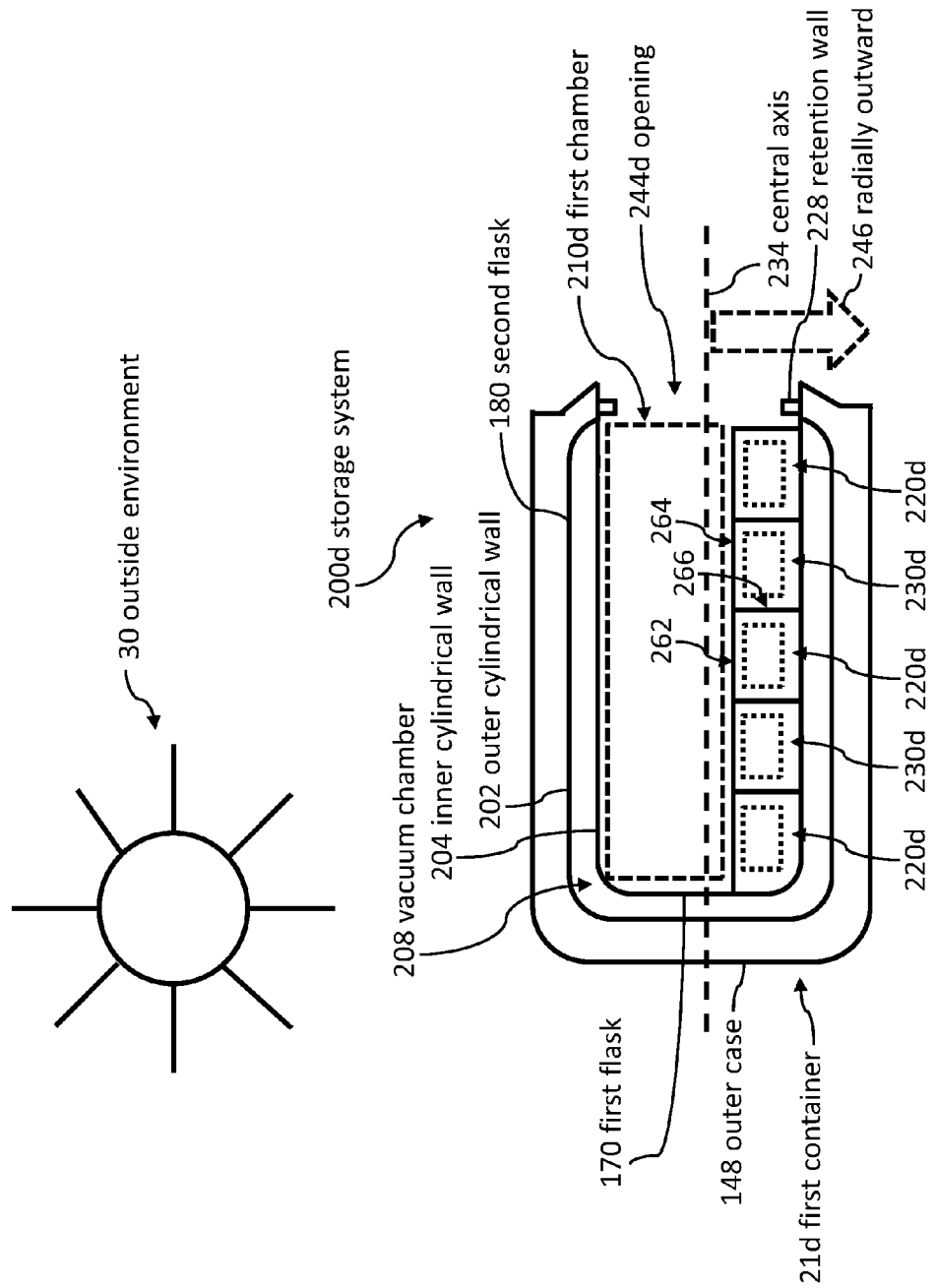
FIG. 21 illustrates a cross-sectional view of the storage system along line A-A from FIG. 20, according to some embodiments.

FIG. 20 illustrates a side view of a storage system 200d. FIG. 21 illustrates a cross-sectional view of the storage system 200d along line A-A from FIG. 20. The lid 18b is hidden in FIG. 21, but is shown in FIG. 20. The first chamber 210d extends from the opening 244d to a distal half of the outer cylindrical wall and/or storage system 200d. The storage system 200d includes several chambers 220d, 230d that hold phase change materials. The chambers 220d, 230d are located radially outward 246 from the first chamber 210d. Walls separate the first chamber 210d from the chambers 220d, 230d that hold phase change materials. Additional walls separate the various phase change materials from each other.

A retention wall 228 can protrude radially inward from an interior of the vacuum flask. The retention wall 228 can be located proximally relative to the chambers 220d, 230d that hold phase change materials having two or more melting temperatures. The retention wall 228 can be configured to prevent chambers 220d, 230d from sliding in a proximal direction and then sliding out of the opening 244d. The retention wall 228 can be a metal wall that is welded inside the vacuum flask. In some embodiments, the retention wall 228 is a plastic or rubber ring that can be deformed to push the ring into the opening 244d and then expands once it is located distally relative to the opening 244d. Once expanded, the ring can prevent the chambers 220d, 230d from sliding in a proximal direction and then sliding out of the opening 244d. Some embodiments include welded metal walls between multiple chambers 220d, 230d.

A first wall 262 separates the first chamber 210d from a second chamber 220d. A second wall 264 separates the first chamber 210d from a third chamber 230d. A third wall 266 separates a second chamber 220d from a third chamber 230d. The first wall 262 is oriented perpendicularly relative to the third wall 266. The third wall 266 separates a distal portion of the phase change system from a proximal portion of the phase change system.

The storage system 200d includes a proximal portion having an opening 244d to the first chamber 210d. The opening 244d is configured to be covered by a removable lid 18b (shown in FIG. 20). The first chamber 210d extends from the proximal portion towards a distal portion of the storage system 200d such that the first chamber 210d is at least as long as a majority of a length between a proximal end 236 of the storage system 200d and a distal end 238 of the storage system 200d (shown in FIG. 20).

A second chamber 220d can be located distally or proximally relative to a third chamber 230d while the second chamber 220d is located outside of the first chamber 210d and is located radially outward relative to the central axis 234. A third chamber 230 can also be located outside of the first chamber 210d and located radially outward relative to the central axis 234.

A "target temperature" can be a "temperature dividing line." In several embodiments, the target temperature can be 74 degrees Fahrenheit (e.g., when the manufacturer recommends storing a medicine at room temperature). In several embodiments, the target temperature can be 36 degrees Fahrenheit (e.g., when the manufacturer recommends refrigerating a medicine).

The chambers 220d, 230d can include different phase chamber materials. The phase change system can have more than two melting temperatures. In some embodiments, a second chamber contains a first phase change material having a first melting temperature; a third chamber contains a second phase change material having a second melting temperature; a fourth chamber contains a third phase change material having a third melting temperature; and a fifth chamber contains a fourth phase change material having a fourth melting temperature. The first and second melting temperatures can be less than a target temperature (e.g., 74 degrees Fahrenheit), and the first melting temperature can be less than (e.g., at least 3 degrees Fahrenheit less than) the second melting temperature. The third and fourth melting temperatures can be greater than the target temperature, and the third melting temperature can be less than (e.g., at least 3 degrees Fahrenheit less than) the fourth melting temperature.

A phase change system with more than two melting temperatures can provide additional temperature protection reliability. For example, a third phase change material can protect against temperatures that are just slightly above a target temperature (e.g., 74 degrees Fahrenheit, 36 degrees Fahrenheit). Thus, the system can protect against even minor temperature variations above the target temperature. However, phase change materials that protect against temperatures that are just slightly above a target temperature are susceptible to changing phase while the storage system is located indoors.

For example, a manufacturer can recommend a maximum EpiPen storage temperature of 77 degrees Fahrenheit, which is very close to typical room temperatures. The phase change system can include a third phase change material with a melting temperature of 76 degrees Fahrenheit. If the storage system is kept in a room that is below 76 degrees Fahrenheit for at least enough time for the third phase change material to solidify, then once the storage system is moved into an outdoor environment that is 79 degrees Fahrenheit, the third phase change material will begin protecting the EpiPen from the outdoor environment that is 79 degrees Fahrenheit.

However, if the storage system is kept in a room that is 78 degrees Fahrenheit for at least enough time for the third phase change material to melt, then once the storage system is moved into an outdoor environment that is 80 degrees Fahrenheit, the third phase change material will fail to protect the EpiPen from the outdoor environment that is 80 degrees Fahrenheit (because the phase change will have occurred before the storage system reaches the outdoor environment). In this case, having a fourth phase change material can be helpful. The fourth phase change material can have a fourth melting temperature that is not as close to typical room temperatures. For example, the fourth melting temperature can be 82 degrees Fahrenheit, which is typically higher than room temperatures. Thus, the fourth phase change material would not be melting while kept in a room that is 78 degrees Fahrenheit for at least enough time for the third phase change material to melt. Then, once the storage system is moved into an outdoor environment that is 80 degrees Fahrenheit, the fourth phase change material will protect the EpiPen from the outdoor environment that is 80 degrees Fahrenheit (by melting).

A manufacturer of a medicine can recommend a minimum storage temperature and a maximum storage temperature for the medicine. In some embodiments, the storage system includes a first phase change material with a first melting temperature that is lower than the target temperature and lower than the minimum storage temperature; the storage system includes a second phase change material with a second melting temperature that is lower than the target temperature, higher than the minimum storage temperature, and higher than the first melting temperature; the storage system includes a fourth phase change material with a fourth melting temperature that is higher than the target temperature and higher than the maximum storage temperature; and/or the storage system includes a third phase change material with a third melting temperature that is higher than the target temperature, lower than the maximum storage temperature, and lower than the fourth melting temperature.

Several phase change system embodiments include two different melting temperatures below a target temperature (e.g., 74 degrees Fahrenheit) and one melting temperature above the target temperature. Some phase change system embodiments include two different melting temperatures above a target temperature (e.g., 74 degrees Fahrenheit) and one melting temperature below the target temperature.

If a difference between a target temperature and an expected cold outdoor temperature is greater than a difference between the target temperature and an expected hot outdoor temperature, then the phase change system can include two different melting temperatures below the target temperature and one melting temperature above the target temperature.

If a difference between a target temperature and an expected hot outdoor temperature is greater than a difference between the target temperature and an expected cold outdoor temperature, then the phase change system can include two different melting temperatures above the target temperature and one melting temperature below the target temperature.

The expected cold outdoor temperature is less than the target temperature. The expected hot outdoor temperature is greater than the target temperature. The expected cold outdoor temperature can be the maximum expected cold outdoor temperature. The expected hot outdoor temperature can be the maximum expected hot outdoor temperature.

A manufacturer of a medicine can recommend a minimum storage temperature and a maximum storage temperature for the medicine. If a difference between a target temperature and the minimum storage temperature is greater than a difference between the target temperature and the maximum storage temperature, then the phase change system can include two different melting temperatures below the target temperature and one melting temperature above the target temperature.

If a difference between a target temperature and the maximum storage temperature is greater than a difference between the target temperature and the minimum storage temperature, then the phase change system can include two different melting temperatures above the target temperature and one melting temperature below the target temperature.

If a difference between the minimum storage temperature and the expected cold outdoor temperature is greater than a difference between the maximum storage temperature and the expected hot outdoor temperature, then the phase change system can include two different melting temperatures below the target temperature and one melting temperature above the target temperature.

If a difference between the maximum storage temperature and the expected hot outdoor temperature is greater than a difference between the minimum storage temperature and the expected cold outdoor temperature, then the phase change system can include two different melting temperatures above the target temperature and one melting temperature below the target temperature.

Any of the storage systems shown in the figures or described herein (e.g., storage systems 10, 11, 12, 200*a*, 200*b*, 200*c*, 200*d*, 200*e*, 200*f*, 200*g*, 200*h*, 200*i*, 300) can be configured according to the temperature information above.

Any of the storage systems shown in the figures or described herein (e.g., storage systems 10, 11, 12, 200*a*, 200*b*, 200*c*, 200*d*, 200*e*, 200*f*, 200*g*, 200*h*, 200*i*, 300) can include three, four, or more phase change materials. The chambers described herein can be subdivided into additional chambers by walls to hold phase change materials with different melting temperatures.

Figure 22:
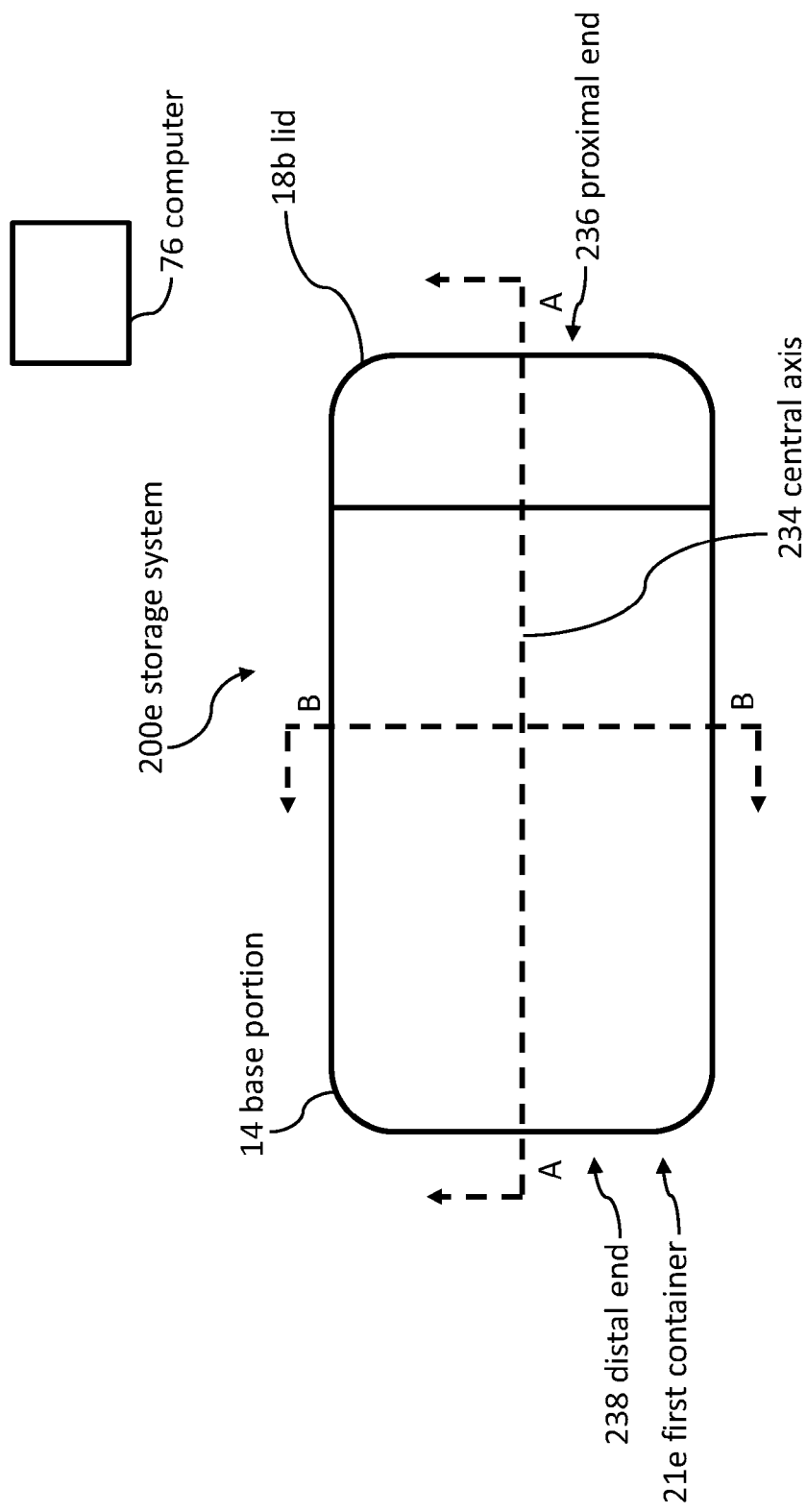
FIG. 22 illustrates a side view of a storage system, according to some embodiments.
Figure 23:
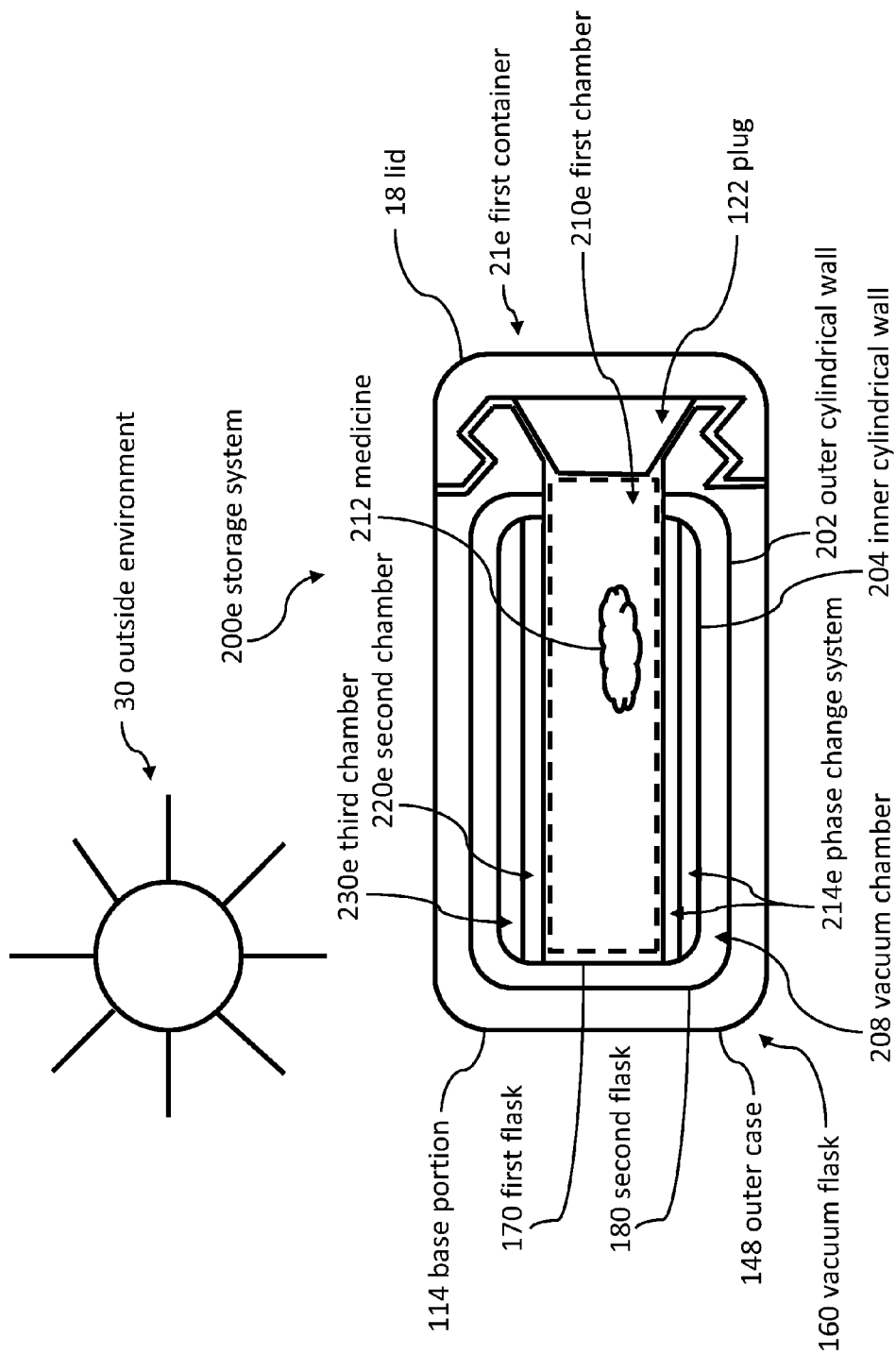
FIG. 23 illustrates a cross-sectional view of the storage system along line A-A from FIG. 22, according to some embodiments.
Figure 24:
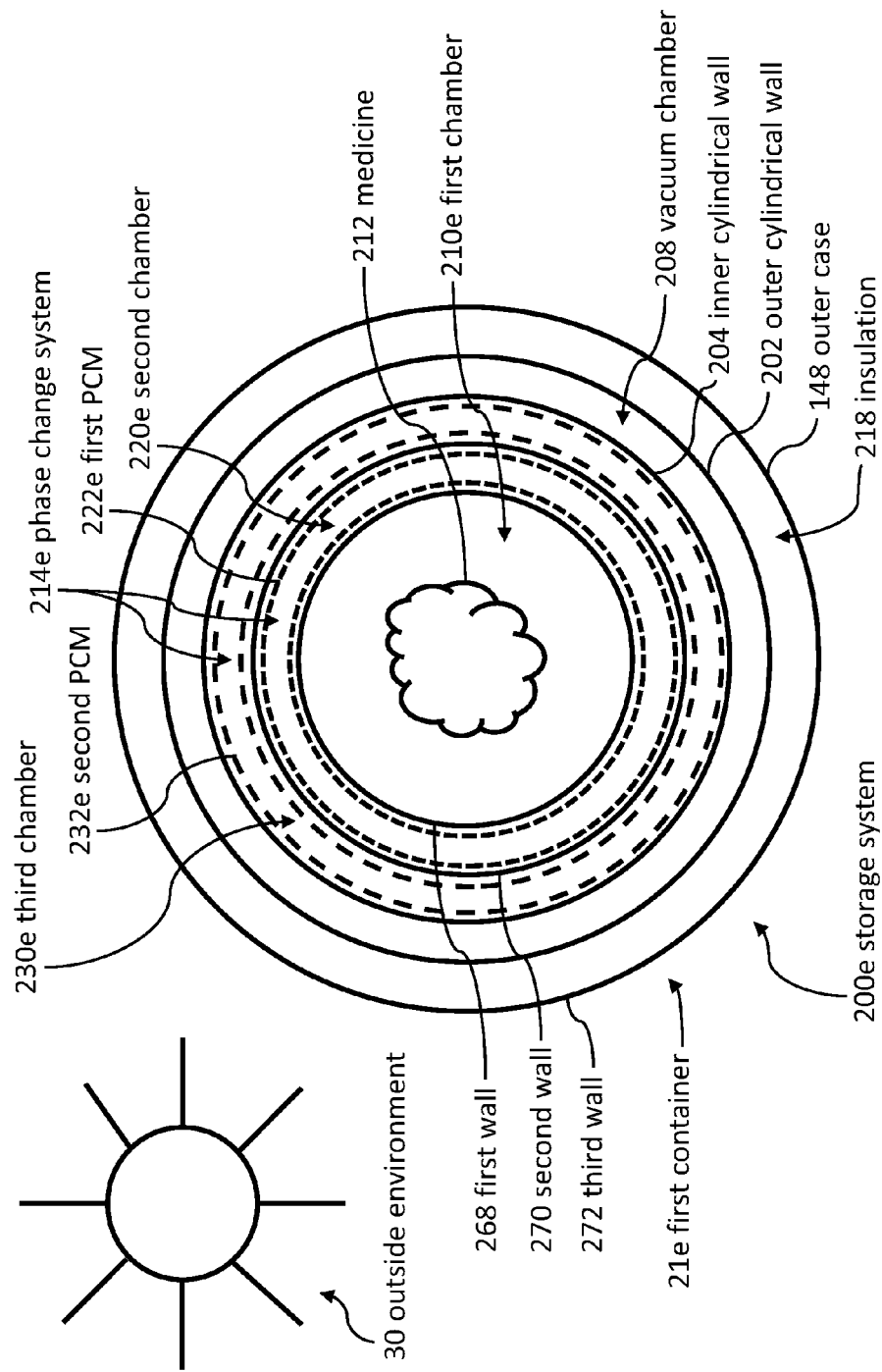
FIG. 24 illustrates a cross-sectional view of the storage system along line B-B from FIG. 22, according to some embodiments.

FIG. 22 illustrates a side view of a storage system 200*e*. FIG. 23 illustrates a cross-sectional view of the storage system 200*e* along line A-A from FIG. 22. FIG. 24 illustrates a cross-sectional view of the storage system 200*e* along line B-B from FIG. 22.

Referring now to FIGS. 23 and 24, the vacuum flask 160 has an interior portion defined by the inner wall 204. The first chamber 210*e* extends from a proximal portion of the interior portion to a distal portion of the interior portion. The first chamber 210*e* is located in a center portion of the interior portion such that the central axis 234 (shown in FIG. 22) runs through the first chamber 210*e*.

Chambers 220*e*, 230*e* include phase change materials that wrap around the first chamber 210*e*. The second chamber 220*e* is located radially outward from the first chamber 210*e*. A third chamber 230*e* is located radially outward from the first chamber 210*e* and radially outward from the second chamber 220*e*. The first chamber 210*e*, the second chamber 220*e*, and the third chamber 230*e* are located radially inward from the vacuum flask (e.g., the inner cylindrical wall 204, vacuum chamber 208, and the outer cylindrical wall 202). The chambers 210*e*, 220*e*, 230*e*, 208 can be surrounded by an insulation (e.g., as shown in FIG. 24).

In some embodiments, a phase change material with a lower melting point is located radially outward from a phase change material with a higher melting point. In several embodiments, a phase change material with a higher melting point is located radially outward from a phase change material with a lower melting point.

The chambers 220*e*, 230*e* can surround the first chamber 210*e* (e.g., the chambers 220*e*, 230*e* can wrap 360 degrees around the first chamber 210*e* and the first chamber 210*e* can include an opening that is not covered by a phase change material).

In several embodiments, the plug 122 holds one or more phase change materials. The plug 122 can be coupled to the lid 188 and can be configured to enter into a portion of the inner cylindrical wall 204 such that a portion of the plug 122 can be located radially inward relative to a portion of the inner cylindrical wall 204.

At least a majority of the first chamber 210*e* is located within the first wall 268 and the second wall 270, which are located within the inner cylindrical wall 204. The inner cylindrical wall 204 is located within the outer cylindrical wall 202. The outer cylindrical wall 202 is located within the third wall 272, which is a portion of the outer case 148. The first wall 268, the second wall 270, the inner wall 204, the outer wall 202, and/or the third wall 272 can be concentric. The first wall 268 is located radially outward from the first chamber 210*e*. The second wall 270 is located radially outward from the first wall 268. The inner wall 204 is located radially outward from the second wall 270. The outer wall 202 is located radially outward from the inner wall 204. The third wall 272 is located radially outward from the outer wall 202.

The insulation 218, the vacuum chamber 208, the first chamber 210e, the second chamber 220e, and the third chamber 230e are concentric. In some embodiments, only a subset of these items are concentric. The walls can also be concentric.

The first wall 268 separates the first chamber 210e from a first portion (e.g., the second chamber 220e) of the phase change system 214e. The second wall 270 separates the first chamber 210e from a second portion (e.g., the third chamber 230e) of the phase change system 214e. The first phase change material 222e surrounds the majority of the first chamber 210e. The second phase change material 232e surrounds the majority of the first chamber 210e.

The second chamber 220e surrounds the majority of the first chamber 210e such that the first phase change material 222e can move 360 degrees around a first perimeter (e.g., as shown in FIG. 24) of the first chamber 210e when the first phase change material 222e is above the first melting temperature. The third chamber 230e surrounds the majority of the first chamber 210e such that the second phase change material 232e can move 360 degrees around a second perimeter (e.g., as shown in FIG. 24) of the first chamber 210e when the second phase change material 232e is above the second melting temperature.

Figure 25:
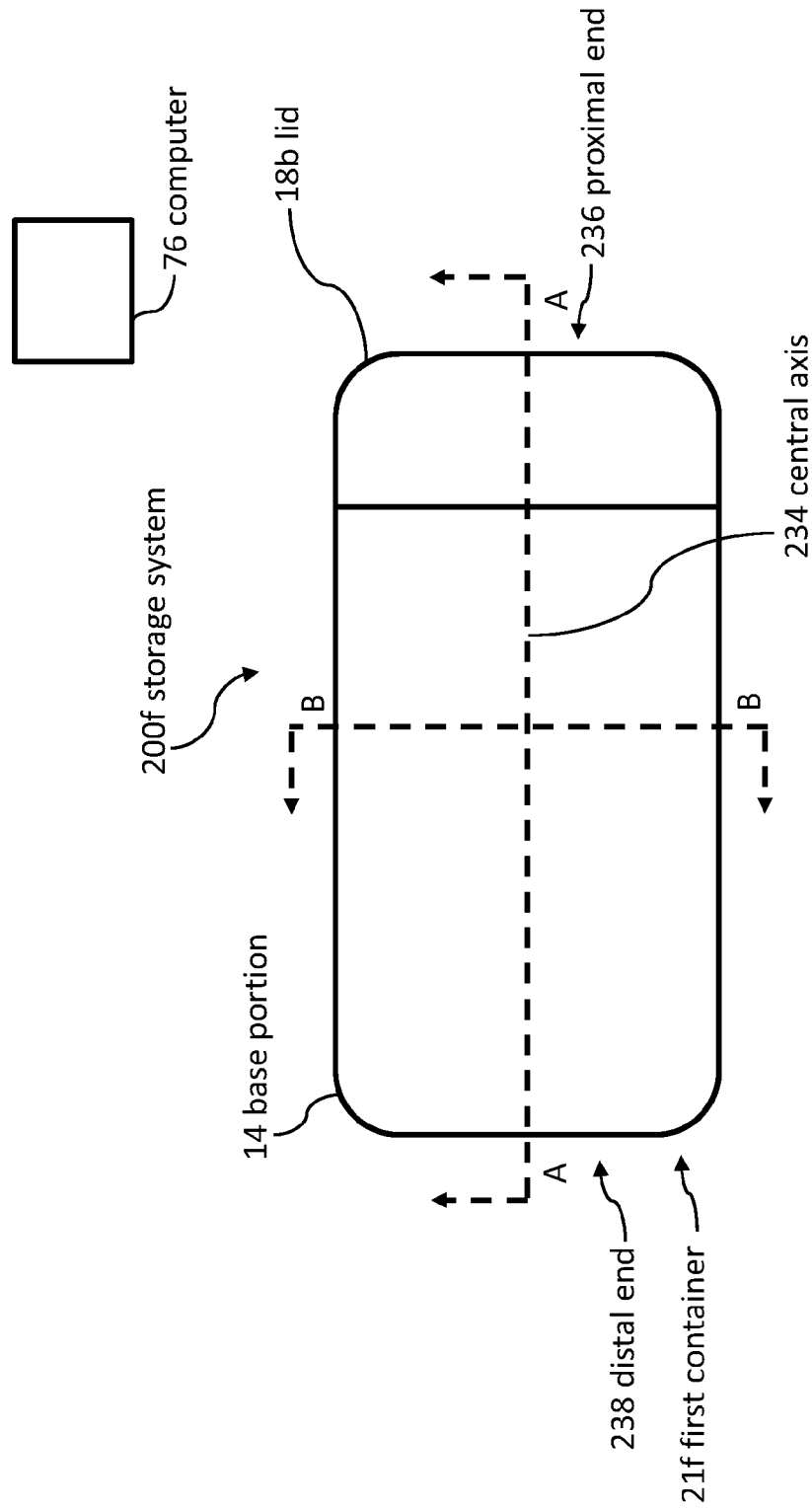
FIG. 25 illustrates a side view of a storage system, according to some embodiments.

FIG. 25 illustrates a side view of a storage system 200f. FIG. 26 illustrates a perspective view showing the side and proximal end of a third chamber 230f, which holds the second phase change material 232f. FIG. 27 illustrates a perspective view showing the side and proximal end of a second chamber 230f, which holds the first phase change material 222f. FIG. 28 illustrates a cross-sectional view of the storage system 200f along line A-A from FIG. 25.

Referring now to FIG. 28, a first wall 278 and a second wall 280 are located within the inner cylindrical wall 204. The first wall 278 is located between the first chamber 210e and a first portion (e.g., the second chamber 220f) of the phase change system 214f. The first wall 278 surrounds at least a first portion (e.g., a proximal portion) of the first chamber 210e. The second wall 280 is located between the first chamber 210e and a second portion (e.g., the third chamber 230f) of the phase change system 214f. The second wall 280 surrounds at least a second portion (e.g., a distal portion) of the first chamber 210e.

The second chamber 220f surrounds the first portion of the first chamber 210e such that the first phase change material 222f (shown in FIG. 27) can move 360 degrees around a first perimeter of the first chamber 210e when the first phase change material 222f is above (i.e., hotter than) the first melting temperature. The third chamber 230f surrounds the second portion of the first chamber 210e such that the second phase change material 232f can move 360 degrees around a second perimeter of the first chamber 210e when the second phase change material 232f is above the second melting temperature.

The first chamber 210e, the second chamber 220f, the third chamber 230f, the vacuum chamber 208, the outer case 148, the inner wall 204, the outer wall 202 are concentric. The first chamber 210e can touch the first flask 170.

The second chamber 220f is located proximally relative to the third chamber 230f. In some embodiments, the positions of the second chamber 220f and the third chamber 230f are switched such that the second chamber 220f is located distally relative to the third chamber 230f. In several embodiments, the second chamber 220f is located radially outward relative to the first chamber 210e.

A third wall 282 can separate the phase change system 214f into a proximal portion (e.g., the second chamber 220f) and a distal portion (e.g., the third chamber 230f). The third wall 282 can be located between the second chamber 220f and the third chamber 230f. The third wall 282 can be oriented perpendicularly relative to the first wall 278 and/or second wall 280. The third wall 282 can protrude radially outward (e.g., directly radially outward or radially outward at an angle).

Figure 29:
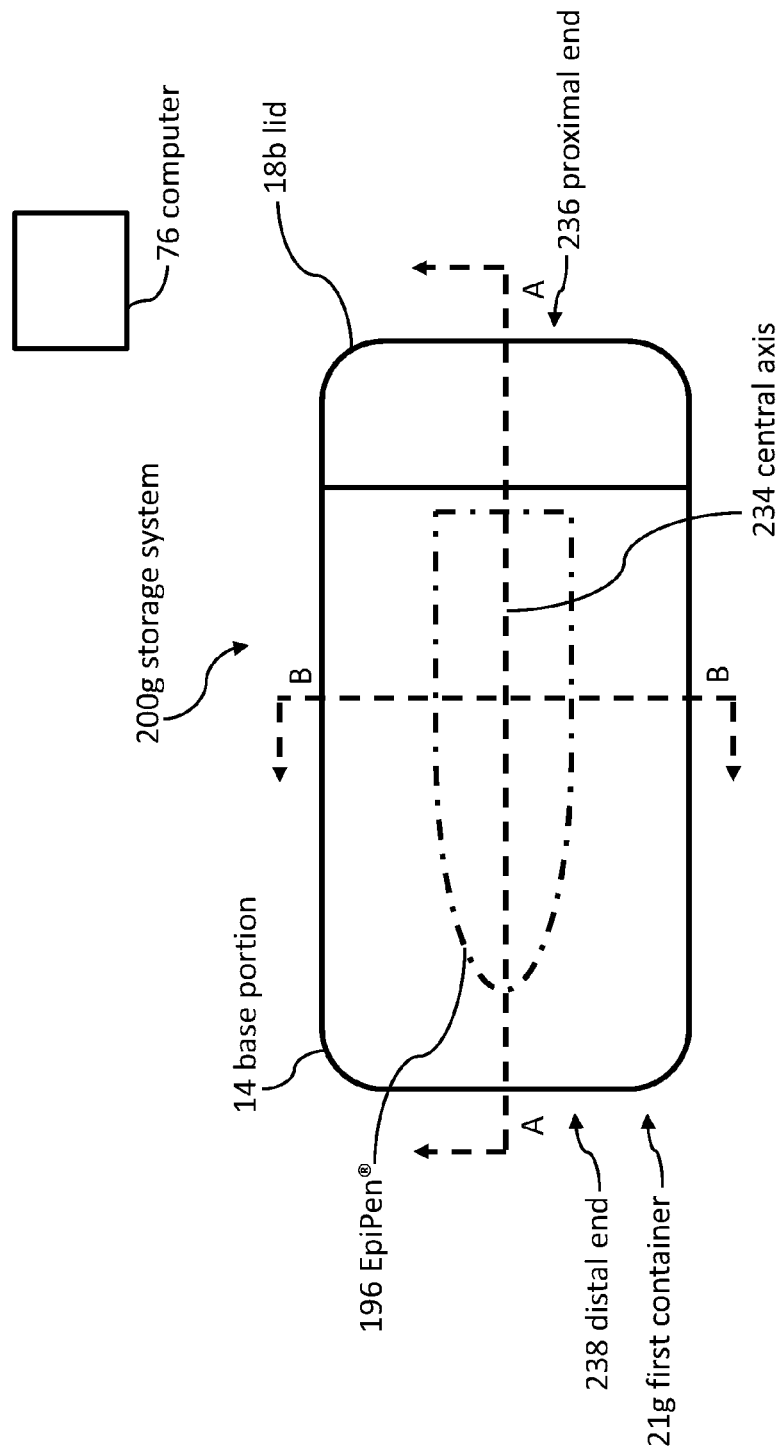
FIG. 29 illustrates a side view of a storage system, according to some embodiments.
Figure 30:
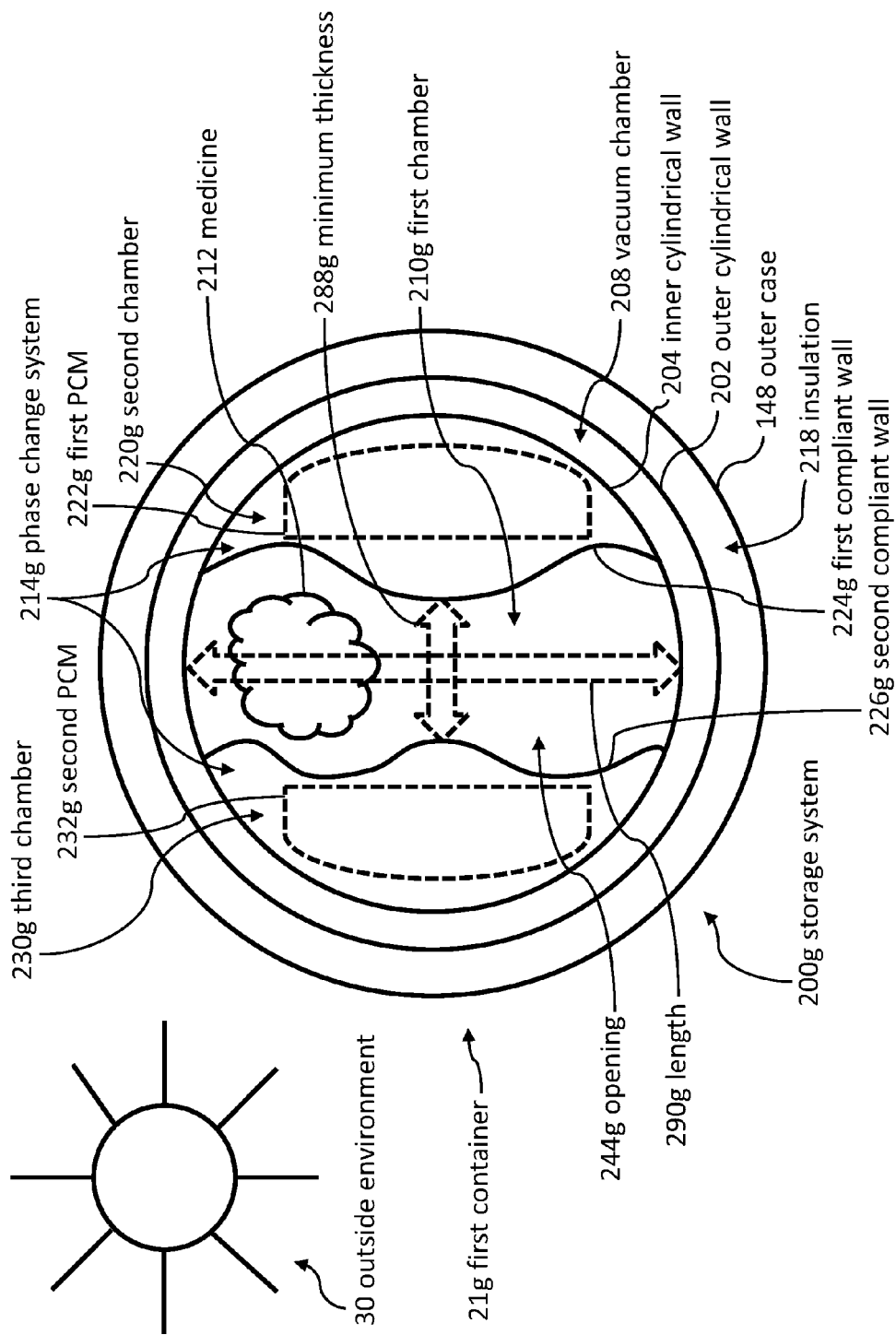
FIG. 30 illustrates the proximal end of the storage system shown in FIG. 29 after a lid is removed, according to some embodiments.

FIG. 29 illustrates a side view of a storage system 200g. The location of an EpiPen 196, which is located inside the storage system 200g, is shown by a dashed line. FIG. 30 illustrates the proximal end of the storage system 200g after the lid 18b (shown in FIG. 29) is removed.

A first compliant wall 224g and a second compliant wall 226g separate the first chamber 210g from the second chamber 220g and third chamber 230g. The compliant walls 224g, 226g enable the opening 244g of the first chamber 210g to expand. For example, pushing a container with medicine 212 into the opening 244g of the first chamber 210g can press the first compliant wall 224g and the second compliant wall 226g radially outward to expand a minimum thickness 288g between the first compliant wall 224g and the second compliant wall 226b in a location configured to hold the medicine 212 (e.g., a portion of the first chamber 210g that can hold the medicine 212). The thickness can start at the minimum thickness 288g and then can expand such that the first chamber 210g comprises an expandable thickness (e.g., to make the expanded thickness at least 50 percent larger than the minimum thickness 288g or at least 100 percent larger than the minimum thickness 288g).

The first compliant wall 224g and the second compliant wall 226b can be made from a plastic or rubber material to enable the walls 224g, 226g to flex and bend. The first compliant wall 224g and the second compliant wall 226b can at least partially conform to the shape of a container that holds the medicine 212.

At least a majority of the first chamber 210g is located between the first compliant wall 224g and the second compliant wall 226g. The first compliant wall 224g separates at least the majority of the first chamber 210g from a first side of the phase change system (e.g., the second chamber 220g). The second compliant wall 226g separates at least the majority of the first chamber 210g from a second side of the phase change system (e.g., the third chamber 230g).

The opening 244g comprises a length 290g from a first end of the opening 244g to a second end of the opening 244g. Prior to inserting the medicine 212 into the first chamber 210g, the length 290g is at least five times larger than the minimum thickness 288g. The first chamber 210g is configured to expand in response to inserting the medicine 212 into the first chamber 210g such that the first chamber 210g can hold containers of medicine having thicknesses that are larger than the minimum thickness 288g of the first chamber 210g.

Many of the embodiments described herein are generally cylindrical, but several embodiments are not cylindrical. Thus, non-cylindrical embodiments can be constructed based on the various features and methods described herein.

Figure 31:
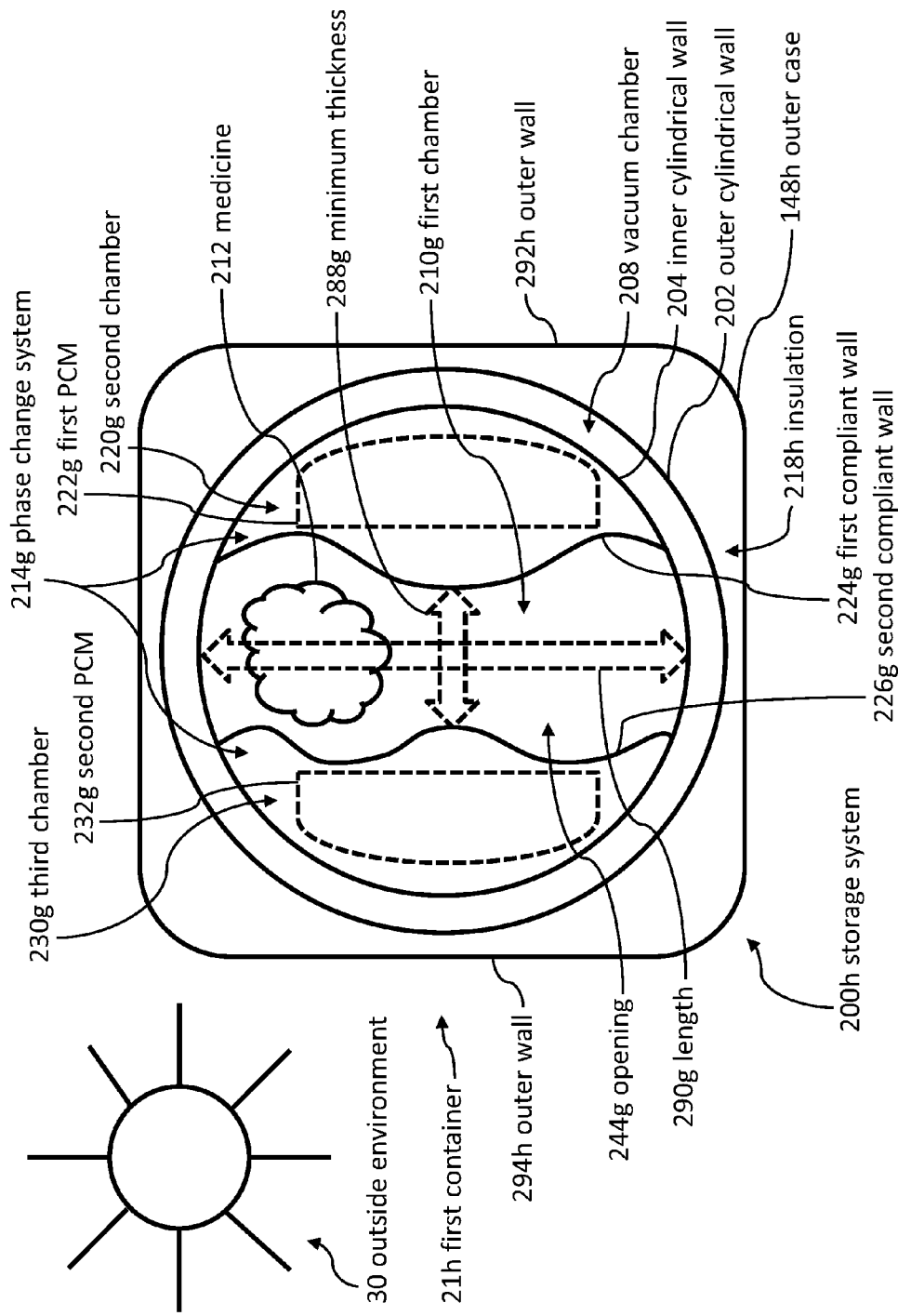
FIG. 31 illustrates the proximal end of a storage system with a non-cylindrical outer case, according to some embodiments.

FIG. 31 illustrates the proximal end of a storage system 200h that is essentially identical to the storage system illustrated in FIG. 30 except the cylindrical outer case 148 has been replaced by a non-cylindrical outer case 148h. Some embodiments do not include a vacuum chamber 208.

The exterior of the outer case 148*h* can be rigid (e.g., metal, stiff plastic) or can be easily compliant (e.g., like a soft pouch or bag).

The storage system 200*h* includes a first outer wall 292*h* and a second outer wall 294*h* that is coupled to the first outer wall 292*h* (e.g., by seams, joints, or other walls). An insulation 218*h* is located between the first outer wall 292*h* and the second outer wall 294*h*. The first chamber 210*g* is surrounded by the first outer wall 292*h* and second outer wall 294*h*. The first chamber 210*g* includes a closeable opening 244*g* that is configured to provide access to the first chamber 210*g* to enable removing the medicine 212 from the storage system 200*h*. Examples of closeable openings include screw-on lids, press-on lids, zippers, and Ziplocks (e.g., an interlocking groove and ridge that can form a seal when pressed together) made by S. C. Johnson & Son, Inc.

The medicine 212 (which can be located in an injection device) is located in the first chamber 210*g*. The storage system 200*h* can include a phase change system 214*g* comprising a second chamber 220*g* having a first phase change material 222*g* and comprising a third chamber 230*g* having a second phase change material 232*g*. The phase change system 214*g* is located between and surrounded by the first outer wall 292*h* and the second outer wall 294*h*. The insulation 218*h* surrounds the phase change system 214*g*.

The embodiment illustrated in FIG. 31 includes a vacuum chamber 208, but several embodiments do not include a vacuum chamber 208 (e.g., to make the storage system compliant like a bag). The insulation 218*h* can be used to slow the rate of heat transfer rather than using a vacuum chamber 208.

A majority of the first chamber 210*g* is located between the first compliant wall 224*g* and the second compliant wall 226*g*. The first compliant wall 224*g* separates at least the majority of the first chamber 210*g* from a first side of the phase change system 214*g*. The second compliant wall 226*g* separates at least the majority of the first chamber 210*g* from a second side of the phase change system 214*g*.

As described above in the context of FIG. 30, the opening 244*g* comprises a length 290*g* from a first end of the opening 244*g* to a second end of the opening 244*g*. Prior to inserting the medicine 212 into the first chamber 210*g*, the length 290*g* is at least five times larger than the minimum thickness 288*g*. The first chamber 210*g* is configured to expand in response to inserting the medicine 212 into the first chamber 210*g* such that the first chamber 210*g* can hold containers of medicine having thicknesses that are larger than the minimum thickness 288*g* of the first chamber 210*g*.

As shown in FIG. 31, the length 290*g* is measured in a direction that is perpendicular to the minimum thickness 288*g*. The minimum thickness 288*g* is measured prior to inserting the medicine 212 into the first chamber 210*g*. The depth of the first chamber 210*g* is measured into the page in FIG. 31. The depth is perpendicular to both the minimum thickness 288*g* and the length 290*g*. For embodiments configured to be used with an EpiPen, the EpiPen is inserted into the first chamber 210*g* such that the longest dimension of the EpiPen is generally aligned with the depth of the first chamber 210*g* (i.e., into the page in FIG. 31).

Figure 32:
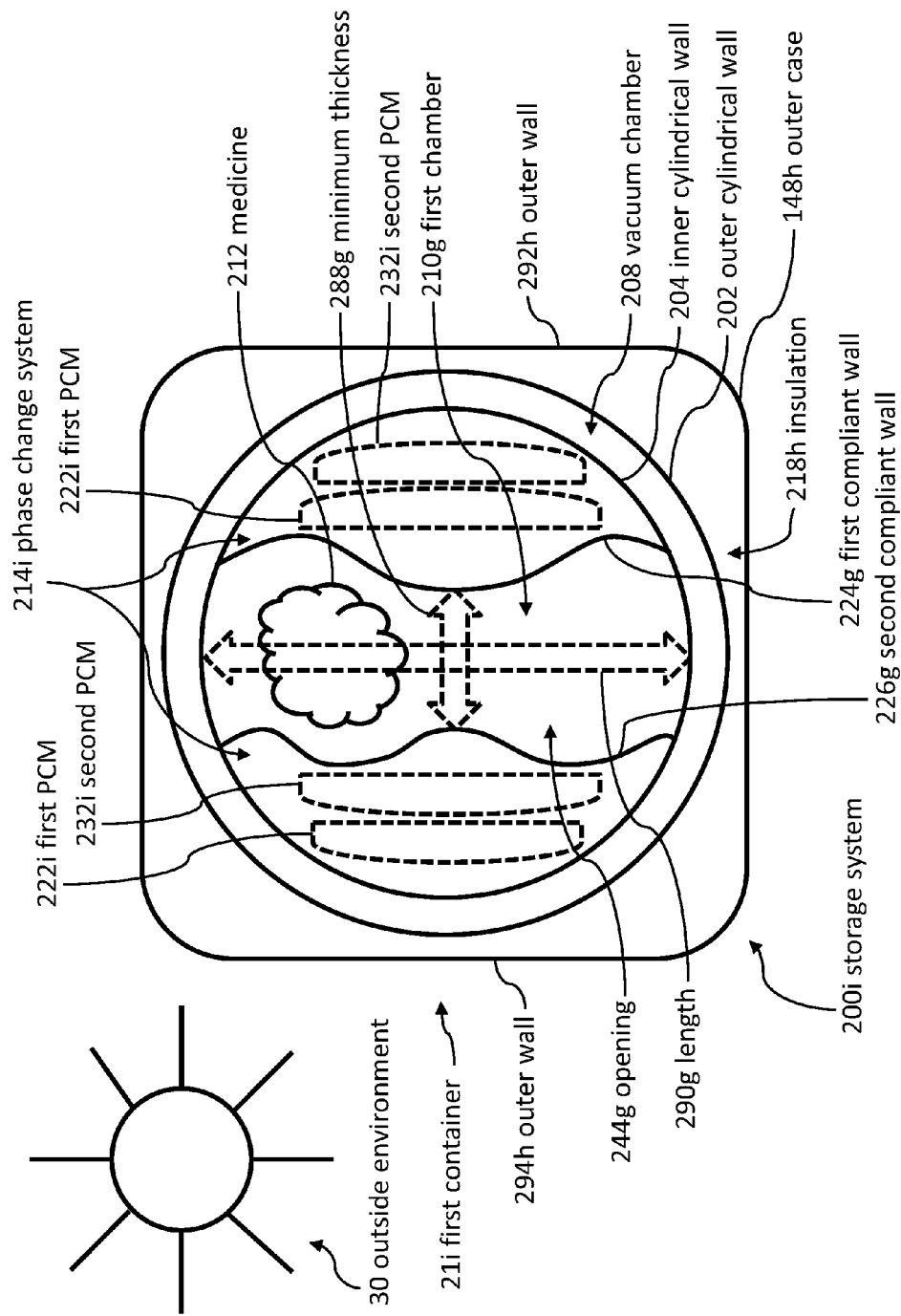
FIG. 32 illustrates the proximal end of a storage system with two phase change materials on the left side, according to some embodiments.

FIG. 32 illustrates the proximal end of a storage system 200*i* that is essentially identical to the storage system 200*h* illustrated in FIG. 31 except the phase change system 214*g* has been modified to include two phase change materials on the left side of FIG. 32 and two phase change materials on the right side of FIG. 32. The first phase change material 222*i* surrounds at least the majority of the first chamber 210*g*. The second phase change material 232*i* surrounds at least the majority of the first chamber 210*g*.

Figure 33:
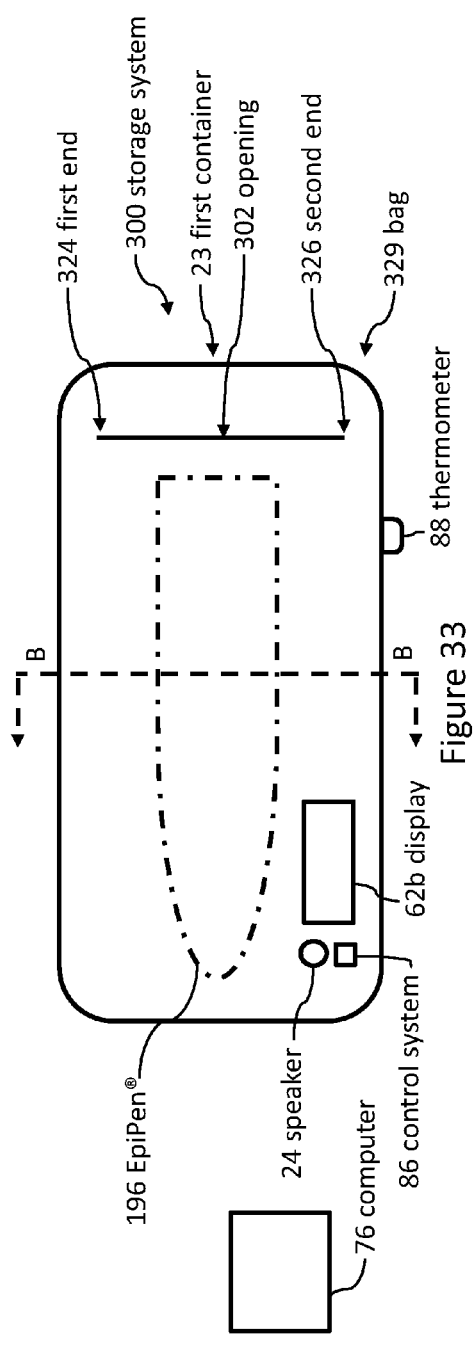
FIG. 33 illustrates a side view of a storage system, according to some embodiments.

FIG. 33 illustrates a side view of a storage system 300. The location of an EpiPen 196, which is located inside the storage system 300, is shown by a dashed line. The storage system 300 can include soft, compliant outer walls. In some embodiments, the storage system 300 is an insulated bag (e.g., a pouch). The bag can be flexible. The opening 302 can include a Ziplock or zipper to enable removing an EpiPen from the first chamber 304 (shown in FIG. 34).

In some embodiments, the compliant bag is made from fabric or molded silicone rubber. In some embodiments, electronic components (e.g., a speaker 24, a control system 86 having a printed circuit board, an electronic display 86) are coupled to a rigid molded plastic housing that is coupled to the compliant bag.

The storage system 300 can include thermometers 68, 88, a temperature display 62*b*, a communication system 70, a vent 84, a temperature probe 64*b*, a speaker 24, seals 66, and a control system 86 (as shown in FIG. 5). Thus, the storage system 300 can wirelessly communicate with the computer 76.

In some embodiments, a cable couples the control system 86 (shown in FIG. 5) to the computer 76 to enable using the computer 76 to configure the various settings described in the context of FIG. 5, to download temperature data from the storage system 300, and/or to download temperature settings and other settings from the computer 76. In several embodiments, wireless communication is used instead of the cable.

Figure 34:
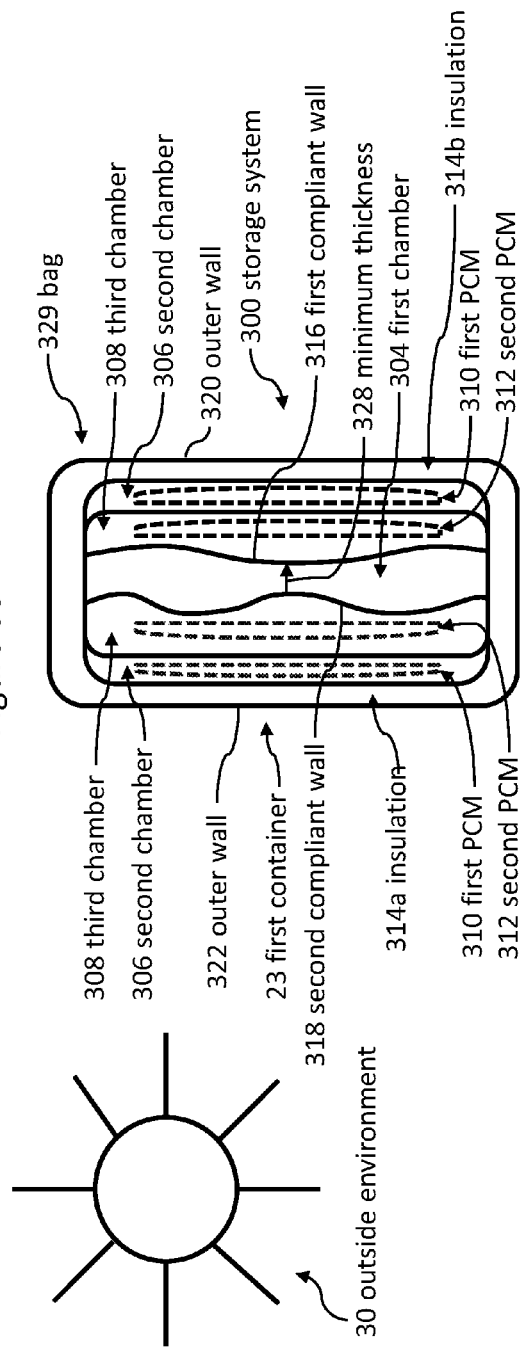
FIG. 34 illustrates a cross-sectional view of the storage system along line B-B from FIG. 33, according to some embodiments.

FIG. 34 illustrates a cross-sectional view of the storage system 300 along line B-B from FIG. 33. The storage system 300 includes a first outer wall 320 and a second outer wall 322 that is coupled to the first outer wall 320 (e.g., by seams, joints, or other walls). An insulation 314*a*, 314*b* is located between the first outer wall 320 and the second outer wall 322. The first chamber 304 is surrounded by the first outer wall 320 and second outer wall 322. The first chamber 304 includes a closeable opening 302 (shown in FIG. 33).

The EpiPen 196 (shown in FIG. 33) can be located in the first chamber 304. The EpiPen 196 can enter the first chamber 304 in a direction into the page in FIG. 34. The storage system 300 can include a phase change system comprising a second chamber 306 that has a first phase change material 310 and comprising a third chamber 308 that has a second phase change material 312. The phase change system is surrounded by the first outer wall 320 and the second outer wall 322. The insulation 314*a*, 314*b* surrounds the phase change system.

A majority of the first chamber 304 is located between the first compliant wall 316 and the second compliant wall 318. The first compliant wall 316 separates at least the majority of the first chamber 304 from a first side of the phase change system. The second compliant wall 318 separates at least the majority of the first chamber 304 from a second side of the phase change system.

Referring now to FIGS. 33 and 34, the opening 302 comprises a length from a first end 324 of the opening 302 to a second end 326 of the opening 302 (as described above in the context of FIG. 30). Prior to inserting the medicine (e.g., the EpiPen 196) into the first chamber 304, the length is at least five times larger than the minimum thickness 328. The first chamber 304 is configured to expand in response to inserting the medicine into the first chamber 304 such that the first chamber 304 can hold containers of medicine having thicknesses that are larger than the minimum thickness 328 of the first chamber 304. The thickness can start at the minimum thickness 328 and then can expand such that the first chamber 304 comprises an expandable thickness (e.g., to make the thickness at least 50 percent larger, at least 100 percent larger, or at least 200 percent larger than the minimum thickness 328).

The thickness of a container of medicine can be found by finding the longest dimension of the container, and then measuring in all directions perpendicular to the longest dimension of the container of medicine. The thickness is the smallest of these dimensions that are perpendicular to the longest dimension.

The storage system 300 can be a flexible bag to enable a collapsible storage system that can more easily fit in a pocket, purse, or other bag when not in use. The outer walls 320, 322 can include a foil coating to reduce the rate of heat transfer in and out of the bag. The chambers can be pliable bags.

At least a majority of the first chamber can be located between portions of the phase change system. For example, a first phase change material can be located on one side of the first chamber and a second phase change material can be located on an opposite side of the first chamber such that the phase change system "sandwiches" the first chamber.

In some embodiments, at least the majority of the first chamber is located between a first compliant wall and a second compliant wall. The first compliant wall can separate at least the majority of the first chamber from a first side of the phase change system. The second compliant wall can separate at least the majority of the first chamber from a second side of the phase change system.

All of the apparatus and system embodiments described herein can be used with any of the methods described herein. Elements from one embodiment can be combined with elements of other embodiments.

A manufacturer of the medicine can recommend a minimum storage temperature and a maximum storage temperature for the medicine. For example, the medicine can include instructions for use that state to store the medicine at 68 degrees Fahrenheit to 77 degrees Fahrenheit (as can be the case with EpiPens made by Meridian Medical Technologies, Inc., a Pfizer Company).

Some embodiments include obtaining the storage system. The storage system can have a first temperature. Embodiments can include placing the storage system inside a building having a first room temperature; leaving the storage system inside the building until the first phase change material is melted and the second phase change material is solidified; placing the medicine inside the first chamber and then closing (e.g., covering an opening) the first chamber from an external environment located outside of the storage system; moving the storage system to a cold environment that is colder than the first room temperature, colder than the first melting temperature, and/or colder than the minimum storage temperature of the medicine, then returning the storage system to a second room temperature before the first phase change material is completely solidified; and/or moving the storage system to a hot environment that is warmer than the first room temperature, warmer than the second melting temperature, and/or warmer than the maximum storage temperature of the medicine. Then, embodiments can include returning the storage system to a third room temperature before the second phase change material is completely melted.

As used herein, "room temperature" is used in a very broad sense, and can include a temperature inside a building and/or a temperature in a temperature-controlled building. The first, second, and third room temperatures can be equal to each other or different from each other. The first, second, and third room temperatures can be in the same building and/or room. The first, second, and third room temperatures can be in different buildings and/or rooms.

After returning the storage system to the second room temperature, some methods include exposing the storage system to the second room temperature until the first phase change material is melted before moving the storage system to a first extreme environment that is colder than the minimum recommended storage temperature. After returning the storage system to the third room temperature, some methods include exposing the storage system to the third room temperature until the second phase change material is solidified before moving the storage system to a second extreme environment that is hotter than the minimum recommended storage temperature.

Several embodiments include continuing to cover (e.g., covering an opening) the first chamber from the external environment from a first time the storage system leaves a fourth room temperature to move to the cold environment; while the storage system is located in the cold environment; and/or until returning the storage system to an environment having a fifth room temperature. Embodiments can also include opening the first chamber to the fifth room temperature in response to returning to the fifth room temperature. Several embodiments include continuing to open the first chamber to the fifth room temperature until the first phase change material is melted and the second phase change material is solidified.

As used herein, "cover" and "covering" are used in a very broad sense to mean covering an opening (e.g., by closing the opening or placing a lid in the opening). "Cover" and "covering" can include "seal" and "sealing," but in some embodiments, "cover" and "covering" might not form an air-tight seal. For example, a lid of a cooler can cover the opening to the cooler, but the lid does not necessarily form an airtight seal.

Several embodiments include obtaining the storage system; placing the storage system in a first inside environment; leaving the storage system in the first inside environment until the first phase change material is melted and the second phase change material is solidified; placing the medicine inside the first chamber and then closing the first chamber from an external environment (e.g., covering an opening leading to the first chamber), wherein the external environment is external relative to the storage system; moving the storage system to a cold outdoor environment that is colder than the first inside environment, colder than the first melting temperature, and/or colder than the minimum storage temperature of the medicine; and then returning the storage system to a second inside environment before the first phase change material is completely solidified. Some embodiments include moving the storage system to a hot outdoor environment that is warmer than the second inside environment, warmer than the second melting temperature, and/or warmer than the maximum storage temperature of the medicine, and then returning the storage system to a third inside environment before the second phase change material is completely melted.

As used herein, an environment is a cold outdoor environment if it is colder than the first inside environment. As used herein, an environment is a hot outdoor environment if it is hotter than the second inside environment. For example, a cold outdoor environment can be colder than a room temperature and a hot outdoor environment can be hotter than the room temperature.

In some embodiments where a first phase change material has a melting temperature greater than 40 degrees Fahrenheit and less than 74 degrees Fahrenheit, the phase change material comprises at least one of PureTemp 6, PureTemp 15, PureTemp 18, and PureTemp 20 made by Entropy Solutions, Inc., which has an office in Plymouth, Minn. In some embodiments where a first phase change material has a melting temperature greater than 40 degrees Fahrenheit and less than 74 degrees Fahrenheit, the phase change material comprises at least one of Paraffin 14-Carbons, Paraffin 15-Carbons, and Paraffin 16-Carbons.

In some embodiments where a second phase change material has a melting temperature greater than 74 degrees Fahrenheit and less than 100 degrees Fahrenheit, the phase change material comprises at least one of PureTemp 25, PureTemp 27, PureTemp 28, and PureTemp 35 made by Entropy Solutions, Inc., which has an office in Plymouth, Minn. In some embodiments where a second phase change material has a melting temperature greater than 74 degrees Fahrenheit and less than 100 degrees Fahrenheit, the phase change material comprises at least one of Paraffin 18-Carbons, Paraffin 19-Carbons, and Paraffin 20-Carbons.

Any of the embodiments illustrated in FIGS. 1-36 can include a storage system (e.g., 10, 11, 12, 200, 200a, 200b, 200c, 200d, 200e, 200f, 200g, 200h, 200i, 300, 400, 500) comprising a phase change system; a first container configured to hold at least a portion of the phase change system; and a first chamber located within the first container and configured to hold a medicine. As explained above, phase change systems can comprises a first phase change material and/or a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. Thus, the phase change system can protect the medicine from temperatures above and below room temperature.

Refrigeration systems typically are large, expensive, fragile, and use electricity to regulate temperature. In contrast, phase change systems can be configured to protect medicine from a first external temperature less than a minimum recommended storage temperature and from a second external temperature greater than a maximum recommended storage temperature by utilizing phase changes to regulate a temperature of the medicine. Because phase change systems do not require electronics and pumps, they are very robust and can be built for a small fraction of the cost of refrigeration systems. Imagine a child who needs an epinephrine injector having to carry even a small refrigerator wherever she goes to prevent hot temperatures from ruining her potentially life-saving epinephrine.

In stark contrast, the child could easily carry a medicine storage system that relies on the phase change systems described herein, which can even be designed to protect against both hot and cold temperatures to eliminate the need for the child to have to guess which temperature protection components she will need for a trip. For example, if the child goes camping, she may need to protect her medicine against both hot afternoon temperatures and cold nighttime temperatures.

Containers can come in many different shapes and sizes. Some containers are vacuum flasks. Vacuum flasks can prevent high heat transfer rates to enable minimizing the amount of phase change material necessary to adequately protect a medicine. Thus, the system can be smaller than would be the case without a vacuum flask.

On the other hand, vacuum flasks often have rigid outer walls, which can make carrying them uncomfortable. Some containers are compliant bags with flexible walls. Compliant bags can be very comfortable to carry. Their flexible outer walls can facilitate fitting them into backpacks and purses (by enabling them to conform to various shapes). The outer wall 322 can be compliant such that the storage system 300 shown in FIG. 34 can be a compliant bag.

Each of the storage systems (e.g., 10, 11, 12, 200, 200a, 200b, 200c, 200d, 200e, 200f, 200g, 200h, 200i, 300) shown in FIGS. 1-34 include a first container. For example, The base portion 14 and the lid 18 shown in FIG. 1 can be a first container. The base portion 14 in FIG. 5 can be a first container. FIG. 1-34 illustrate many first containers 16, 17, 20, 21, 21a-21i, 23. Containers may be manufactured from many materials including metal, plastic, and cardboard.

FIG. 7 illustrates a storage system 12 with an injection device 150 configured to inject a drug 190 (e.g., epinephrine). The injection device 150 is located in the first chamber (e.g., a void 154). The injection device can comprise a needle 151 configurable to inject the epinephrine into a person. The injection device 150 having a needle 151 is located in the first chamber such that the storage system 12 shields the injection device 150 from an external environment (e.g., an outside environment 30). Any of the storage systems (e.g., 10, 11, 12, 200, 200a, 200b, 200c, 200d, 200e, 200f, 200g, 200h, 200i, 300) shown in FIGS. 1-36 can include an injection device 150 in the first chamber.

As shown in FIG. 7, the first container 20 can comprise a vacuum chamber (e.g., the area located between the first flask 170 and the second flask 180) such that the vacuum chamber is configured to thermally insulate the medicine from an external environment (e.g., an outside environment 30). The majority of the first chamber 154 is located radially inward from the vacuum chamber.

FIG. 33 illustrates a side view of a storage system 300. The location of an EpiPen 196 (or other medicine), which is located inside the storage system 300, is shown by a dashed line. The storage system 300 can include soft, compliant outer walls. In some embodiments, the storage system 300 is an insulated bag (e.g., a pouch). The bag can be flexible. The opening 302 can include a Ziploc (made by S.C. Johnson & Son, Inc.) or zipper to enable removing an EpiPen from the first chamber 304 (shown in FIG. 34).

As shown in FIGS. 33 and 34, the first container 23 can comprise a compliant bag 329. FIG. 33 illustrates the compliant bag 329 with a closeable opening 302, which is coupled to the first chamber 304 (shown in FIG. 34) that holds the EpiPen 196. The closeable opening 302 is configurable to provide access to the medicine (e.g., 196).

As shown in FIG. 34, the phase change system (e.g., 310 and 312) is located inside of the compliant bag 329 such that insulation 314a, 314b of the compliant bag 329 thermally insulates the phase change system from an external environment (e.g., the outside environment 30). In some embodiments, a majority of the phase change system (e.g., 310, 312) is located between a first portion 314a of the insulation and a second portion 314b of the insulation. In several embodiments, a majority of the first chamber 304 is located between a first portion 314a of the insulation and a second portion 314b of the insulation.

Figure 35:
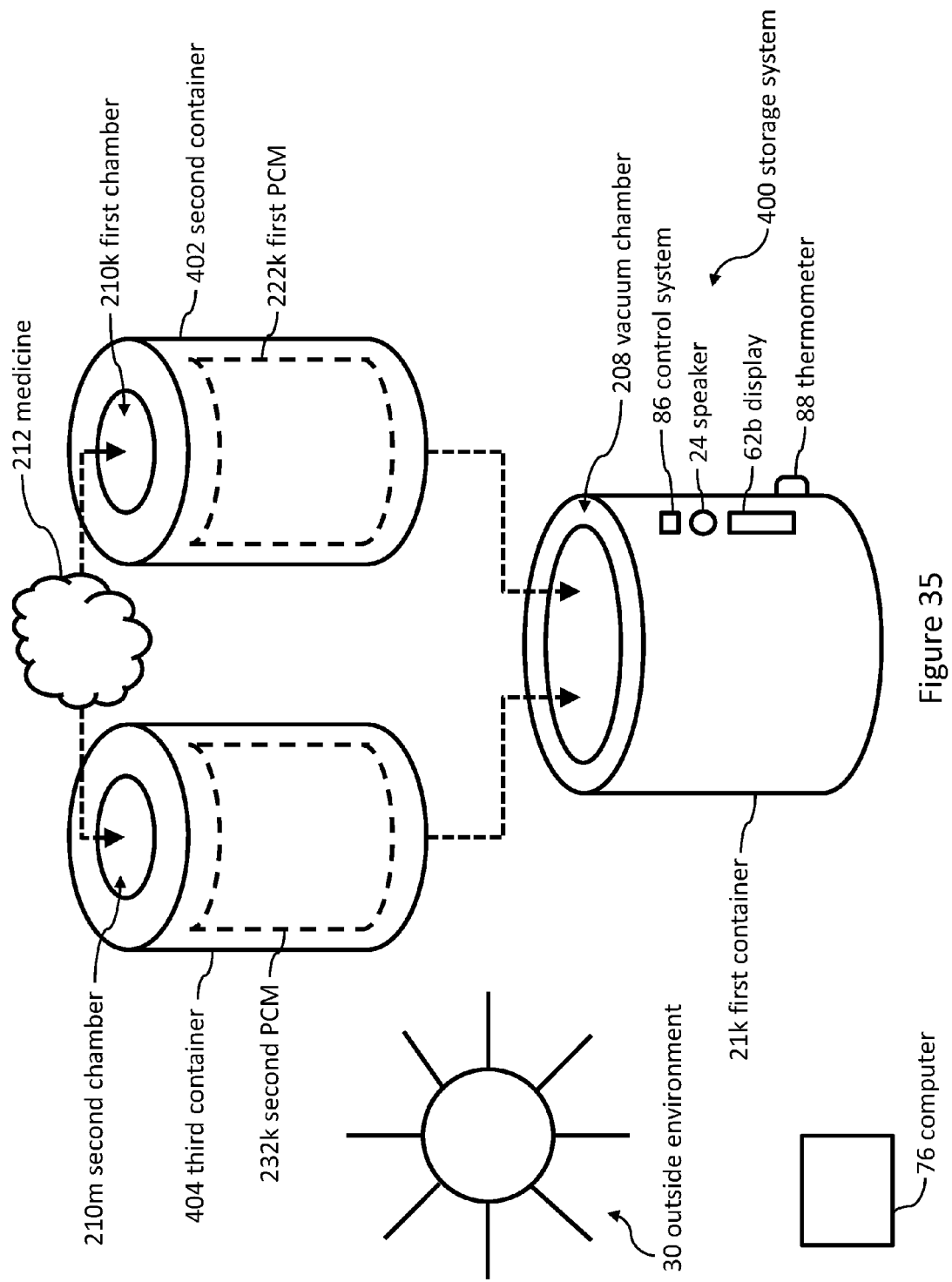
FIG. 35 illustrates a perspective view of a storage system with two inserts, according to some embodiments.

Referring now to FIG. 35, minimizing the size of the first container 21k that a person has to carry to protect her medicine can be important. Generally, a smaller container is more convenient and easier to carry. Rather than require a person to carry two phase change materials at all times, the storage system 400 embodiment illustrated in FIG. 35 enables a person to remove a first phase change material 222k from a first container 21k and then replace the first phase change material 222k with a second phase change material 232k (and vice versa). Thus, a second container 402 that holds the first phase change material 222k is interchangeable with a third container 404 that holds the second phase change material 232k. A person can replace the second container 402 with the third container 404 (and vice versa) by removing the second container 402 from the first container 21k, and then inserting the third container 404 into the first container 21k (which can include a lid as shown in other embodiments).

The first container 21k, the second container 402, and the third container 404 are parts of a storage system 400 that enables a user to optimize the first container 21k for either protection against warm environments or protection against cold environments. The second container 402 can have a first chamber 210k configured to hold a medicine. The third container 404 can also have a chamber 210m configured to hold a medicine. In other embodiments, the first container 21k has a chamber configured to hold a medicine, but the second container 402 and the third container 404 do not have chambers to hold medicine.

FIG. 35 illustrates an embodiment of a storage system 400 having a phase change system (e.g., 232k, 222k). The phase change system can include a first phase change material 222k and a second phase change material 232k. The first phase change material 222k can have a first melting temperature greater than 40 degrees Fahrenheit and less than 74 degrees Fahrenheit. The second phase change material 232k can have a second melting temperature greater than 74 degrees Fahrenheit and less than 100 degrees Fahrenheit.

The second container 402 can hold the first phase change material 222k. The third container 404 can hold the second phase change material 232k. In the embodiment illustrated in FIG. 35, the second container 402 and the third container 404 are interchangeable within the first container 21k such that the storage system 400 is alternatively configurable to protect the medicine 212 from a first environment below 74 degrees Fahrenheit using the first phase change material and from a second environment above 74 degrees Fahrenheit using the second phase change material. Medicine 212 can be inserted into the first chamber 210k, the second chamber 210m, and/or the first container 21k.

The embodiment shown in FIG. 35 can be used with any of the features, elements, parts, and systems shown in FIGS. 1-34. For example, the first container 21k, the second container 402, and/or the third container 404 can include a vacuum chamber 208 (e.g., from a vacuum flask). The vacuum chamber 208 can be configured to thermally insulate the medicine 212 from an external environment (e.g., an outside environment 30).

In some embodiments, the first container 21k, the second container 402, and/or the third container 404 is a compliant bag with insulation. Many different types of insulation can be used. Some embodiments use Thinsulate made by the 3M Corporation. The first container 402 can comprise a compliant bag (as described in other embodiments) having insulation configured to thermally insulate the medicine from an external environment (e.g., an outside environment 30).

The storage system 400 can use a lid 18 (shown in FIG. 5) that is coupled to the first container 21k. At least one of the first chamber 210k and the second chamber 210m can be oriented such that the lid (coupled to the first container 21k) is removable to provide access to the medicine 212.

Figure 36:
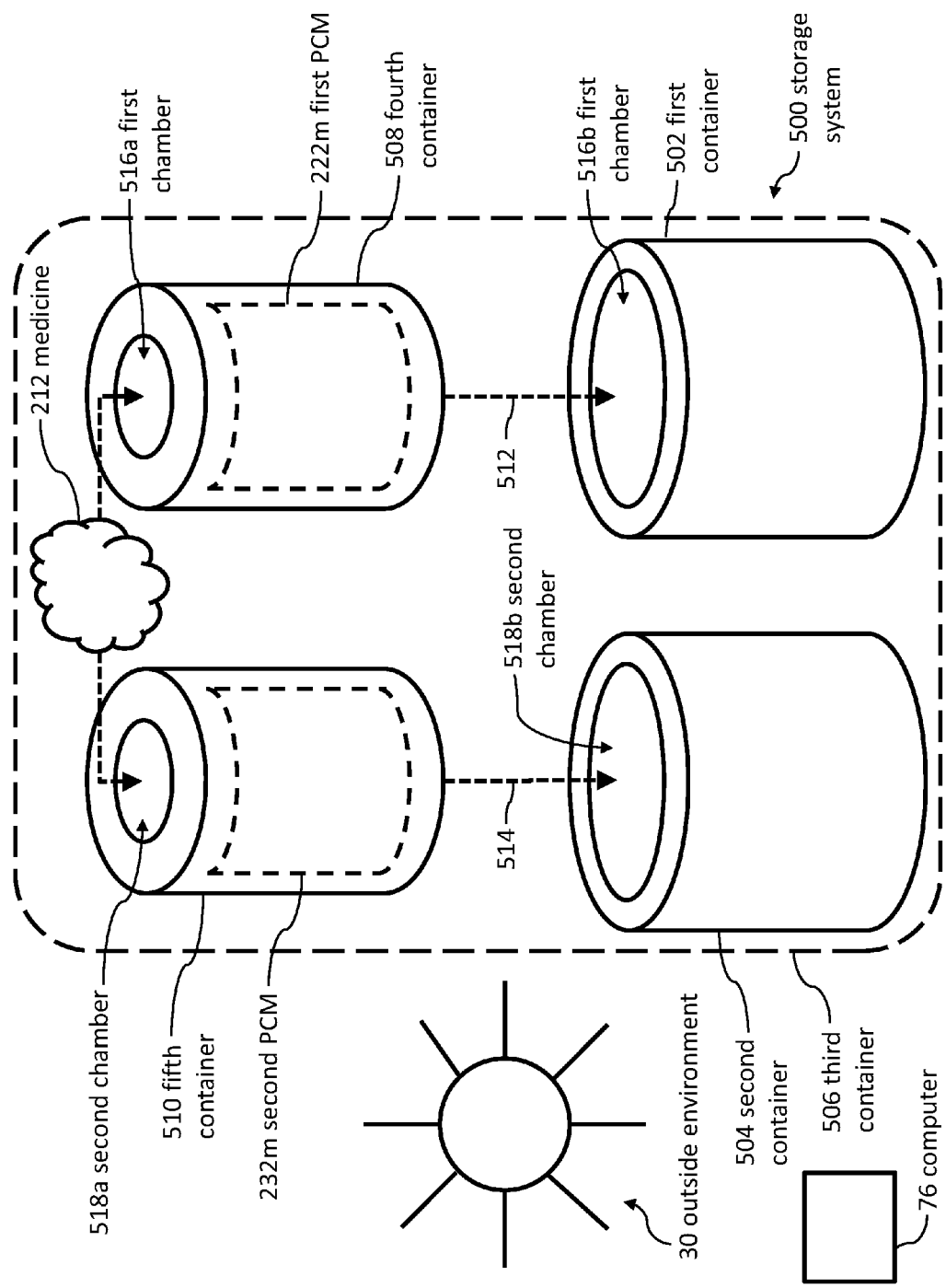
FIG. 36 illustrates a perspective view of a storage system with two temperature-protection subsystems, one of which can be optimized for cold protection and one of which can be optimized for hot protection, according to some embodiments.

FIG. 36 illustrates a storage system 500 comprising a first container 502, a second container 504, and a third container 506. The first container 502 and the second container 504 are located inside the third container 506. A first phase change material 222m can be located in a fourth container 508, which can be inserted into the first container 502 (as shown by Arrow 512). A second phase change material 232m can be located in a fifth container 510, which can be inserted into the second container 504 (as shown by Arrow 514). The first container 502 and/or the fourth container 508 can have a first chamber 516a, 516b configured to hold a first medicine 212. Once the fourth container 508 is inserted into the first container 502, the first container 502 can comprise a first phase change material 222m having a first melting temperature greater than 40 degrees Fahrenheit and less than 74 degrees Fahrenheit.

The second container 504 and/or the fifth container 510 can have a second chamber 518a, 518b configured to hold a second medicine 212. Once the fifth container 510 is inserted into the second container 504, the second container 504 can comprises a second phase change material 232m having a second melting temperature greater than 74 degrees Fahrenheit and less than 100 degrees Fahrenheit.

The first container 502 and the second container 504 can be any of the containers described herein (e.g., containers 16, 17, 20, 21, 21a-21i, 21k, 23 shown in FIGS. 1-35). For example, the first container 502 shown in FIG. 36 can be the embodiment shown in FIG. 5. The first container 502 shown in FIG. 36 can be the embodiment shown in FIG. 12 (and thus can include a vacuum chamber 208 to thermally insulate the first medicine from an external environment). The second container 504 be the storage system 300 shown in FIGS. 33 and 34, and thus can include a compliant bag 329 having insulation 314a, 314b configured to thermally insulate medicine from an external environment (e.g., an outside environment 30).

In other words, the third container 506 illustrated in FIG. 36 can hold any two (or more) of the other embodiments described in the context of FIGS. 1-35. The embodiment represented in FIG. 36 is important because it enables a system 500 that can be optimized for many different circumstances. For example, room temperature (e.g., a first environment) might be 74 degrees Fahrenheit. The user might need to take her medicine into a second environment that is only zero degrees Fahrenheit (e.g., Minnesota in the winter). The user might also need to take her medicine into a third environment that is 90 degrees Fahrenheit (e.g., Minnesota in the summer). As a result, the medicine needs to be protected from a 74 degree drop and from a 16 degree rise. A 74 degree drop is much more extreme than a 16 degree rise. As a result, the cold-weather protection system must provide much better thermal protection than the warm-weather protection system. (The opposite can be true in other climates.)

This Minnesotan likely wants to have a system 500 that is optimized for her climate. For example, the first container 502 may have a vacuum chamber and rigid outer walls made of metal (to withstand the vacuum). Thus, the vacuum chamber may drastically reduce the rate of heat loss, and thus protect her medicine. This design, however, is bulky and unnecessary for the relatively small temperature difference of summer. Thus, for summer use, the system 500 can include a second container 504 that is an insulated, compliant bag with relatively little phase change material. This second container 504 can be much smaller and more convenient to carry than the first container 502 in this example. Providing both the first container 502 and the second container 504 to the user in one container 506 can greatly simplify the user's experience receiving a thermal protection system 500.

Some embodiments include a website that enables a customer to enter climate information. The website can then recommend a thermal protection system 500 at least partially in response to the climate information. For example, a customer in Florida would be recommended a different combination of embodiments from FIGS. 1-35 than a customer in Minnesota would be recommended.

In some cases, a medicine has a recommended minimum or maximum storage temperature that is close to a room temperature or 74 degrees Fahrenheit. This situation can be problematic because selecting a melting temperature (of a phase change material) that is close to room temperature or 74 degrees Fahrenheit can result in the phase change material changing phases before the phase change material leaves an indoor environment in which the storage system is stored.

For example, a house's internal temperature may be between 67 degrees Fahrenheit and 80 degrees Fahrenheit. If the minimum recommended storage temperature of a medicine is 69 degrees Fahrenheit, then the first phase change material may have a melting temperature of 69 degrees Fahrenheit. As a result, the first phase change material could freeze before the storage system ever leaves the house.

A solution to this problem is to have more than two melting temperatures of phase change materials in the storage system. For example, a first phase change material could have a melting temperature of 69 degrees Fahrenheit, a second phase change material could have a melting temperature of 81 degrees Fahrenheit, and a third phase change material could have a melting temperature of 65 degrees Fahrenheit. Thus, if the first phase change material freezes before the storage system leaves the house, then the third phase change material could provide backup protection against cold environments (even if this backup protection is slightly lower than the minimum recommended storage temperature).

Any of the embodiments described in any of the figures can include one, two, three, four, or more phase change materials with unique melting temperatures. Any of the embodiments can include a first phase change material having a first melting temperature greater than 40 degrees Fahrenheit and less than 74 degrees Fahrenheit, a second phase change material having a second melting temperature greater than 74 degrees Fahrenheit and less than 100 degrees Fahrenheit, a third phase change material having third melting temperature less than the first melting temperature, and/or a fourth phase change material having a fourth melting temperature greater than the second melting temperature. In several embodiments, the third melting temperature is greater than 40 degrees Fahrenheit and less than 74 degrees Fahrenheit. In some embodiments, the fourth melting temperature is greater than 74 degrees Fahrenheit and less than 100 degrees Fahrenheit. These various phase change materials can be located in any of the chambers and containers described herein. In some embodiments, more than one phase change material is located in a single chamber. In several embodiments, different phase change materials are located in different chambers.

Any of the embodiments can include a first phase change material having a first melting temperature greater than 40 degrees Fahrenheit and less than 74 degrees Fahrenheit, a second phase change material having a second melting temperature greater than 74 degrees Fahrenheit and less than 100 degrees Fahrenheit, a third phase change material having third melting temperature less than the first melting temperature, and/or a fourth phase change material having a fourth melting temperature greater than the second melting temperature. In several embodiments, the third melting temperature is greater than 40 degrees Fahrenheit and less than 74 degrees Fahrenheit. In some embodiments, the fourth melting temperature is greater than 74 degrees Fahrenheit and less than 100 degrees Fahrenheit.

In several embodiments, storage systems include "chambers" (e.g., to hold phase change material or other items). These chambers can be formed by containers having chambers. In some embodiments, a container has a single chamber to hold a phase change material. In several embodiments, a container has many chambers. In some embodiments, a first container has many containers (e.g., formed by walls inside the first container).

Figure 37:
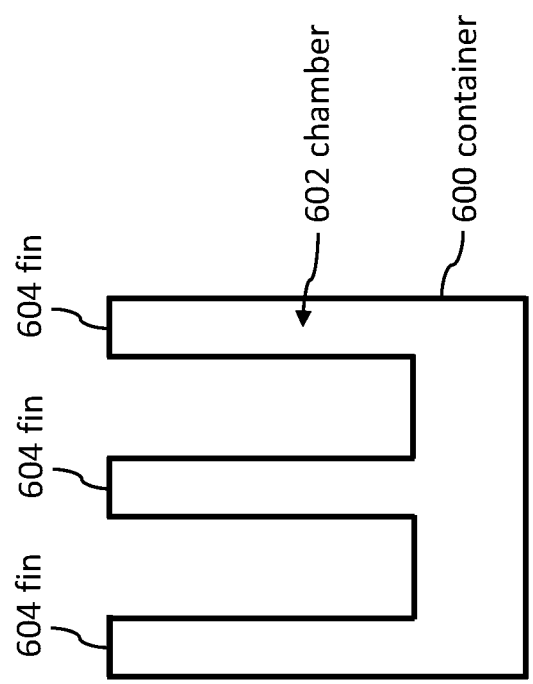
FIG. 37 illustrates a front view of a container having a chamber configured to hold at least one phase change material, according to some embodiments.

FIG. 37 shows a front view of a container 600 having a chamber 602 configured to hold at least one phase change material. The container 600 has narrower sections, which are fins 604, to increase the rate of heat transfer between the phase change material and the area external to the container 600 (e.g., a chamber having a medicine). The chamber 602 can be used in any of the embodiments described herein. The fins 604 causes the container 600 to have a larger surfaces area (to increase the rate of heat transfer) than would be the case with a container of the same volume having a cubic shape.

Any of the embodiments described in the context of FIGS. 1-37 can be used with any of the methods described herein.

Some embodiments include obtaining a storage system comprising a phase change system, a first container configured to hold at least a portion of the phase change system, and a first chamber located within the first container, wherein the first chamber is configured to hold a medicine, and wherein the phase change system comprises a first phase change material and a second phase change material, the first phase change material having a first melting temperature greater than 40 degrees Fahrenheit and less than 74 degrees Fahrenheit, and the second phase change material having a second melting temperature greater than 74 degrees Fahrenheit and less than 100 degrees Fahrenheit; placing the medicine in the first chamber; and storing the storage system in a first environment such that the first phase change material is liquid and the second phase change material is solid.

Several embodiments include moving the storage system to a second environment that is cooler than the first environment, and then moving the storage system to a warmer environment, relative to the second environment, before all of the first phase change material freezes; and moving the storage system to a third environment that is warmer than the first environment, and then moving the storage system to a cooler environment, relative to the third environment, before all of the second phase change material melts.

Several embodiments include moving the storage system to a second environment that is cooler than the first environment, and then moving the storage system to a warmer environment, relative to the second environment, in response to receiving a first temperature alert; and moving the storage system to a third environment that is warmer than the first environment, and then moving the storage system to a cooler environment, relative to the third environment, in response to a second temperature alert.

Some embodiments include moving the storage system to a second environment that is cooler than the first environment, and then moving the storage system to a warmer environment, relative to the second environment, before the medicine reaches a first medicine temperature that is cool enough to harm the medicine and/or before an internal portion of the storage system reaches a minimum temperature threshold; and moving the storage system to a third environment that is warmer than the first environment, and then moving the storage system to a cooler environment, relative to the third environment, before the medicine reaches a second medicine temperature that is warm enough to harm the medicine and/or before the internal portion of the storage system reaches a maximum temperature threshold.

Some embodiments include moving the storage system to a second environment that is cooler than the first environment, and then moving the storage system to a warmer environment, relative to the second environment, in response to the medicine reaching a first medicine temperature that is cool enough to harm the medicine, in response to the medicine reaching a minimum temperature threshold, and/or in response to an internal portion of the storage system reaches the minimum temperature threshold; and moving the storage system to a third environment that is warmer than the first environment, and then moving the storage system to a cooler environment, relative to the third environment, in response to the medicine reaching a second medicine temperature that is warm enough to harm the medicine, in response to the medicine reaching a maximum temperature threshold, and/or in response to the internal portion of the storage system reaching the maximum temperature threshold.

The circumstances surrounding an emergency in which a person needs medicine storage in a storage system can be traumatic. For example, during anaphylactic shock, a person may struggle to breathe. This situation can cause people, including family members and caregivers, to panic. In such high-intensity emergencies, some people might not be able to think clearly enough or act quickly enough to find the storage system.

One solution to this problem is to communicatively couple the storage system to a remote computing device 76 such as a smartphone. Referring now to FIG. 5, a person can use application software (e.g., an "app") on her remote computing device 76 to send a wireless communication to the communication system 70 of the storage system 11. Then, in response to receiving the wireless communication, the storage system 11 can emit a sound from the speaker 24 and/or can emit a light (e.g., a flashing light) from the light 85, which can comprise a light emitting diode. The remote computing device 76 can communicate with the storage system 11 via WiFi, cellular networks, Bluetooth, radio waves, or via any other suitable means of wireless communication.

The sound and light emitted by the storage system 11 can enable people to locate storage systems 11 hidden in crowded kitchen cabinets, hidden under clothing in bedroom dressers, or buried under gear in a car during a camping or skiing trip. Any of the storage systems described herein can be communicatively coupled with a remote computing device 76.

In some embodiments, the application software on the remote computing device 76 points a user to the location of the storage system 11. Thus, the user can following the directions on the application software to find the storage system 11. This pointing can be an arrow or indicators of whether the user is getting closer to or farther from the storage system 11.

Some medicine users forget to take their medicine with them. For example, they may forget their medicine at home, at a park, or at an office. Forgetting their medicine can place their life in danger. A solution to this problem is to provide an alert via the remote computing device 76 when an alert system (which can include the storage system 11, the remote computing device 76, servers, and other items) detects that the remote computing device 76 is located more than a predetermined threshold away from the storage system 11. For example, if the user is at least 30 feet or at least 100 feet away from her storage system (containing medicine), then the user's remote computing device 76 (e.g., a smartphone) can provide an alert (e.g., a push notification, a text message, a sound, a warning message, a warning icon, a flashing light).

The system can determine the location of the remote computing device 76 (e.g., via GPS). The remote computing device 76 can attempt to communicate with the storage system 11 via close-range communication technologies such as Bluetooth. If the remote computing device 76 cannot communicate with the storage system 11 via close-range communication technologies, then the alert system can assume the storage system 11 is not sufficiently close to the remote computing device 76, and thus the remote computing device 76 can emit an alert.

In several embodiments, the alert system actually measures an approximate distance between the storage system 11 and the remote computing device 76 based on a strength of a wireless signal emitted by the storage system 11 as measured by the remote computing device 76. If this signal strength is less than a predetermined threshold or is otherwise indicative of the storage system being too far away, then the remote computing device 76 can emit an alert.

In some embodiments, the remote computing device 76 determines if the remote computing device 76 is located in a vehicle (e.g., based on detecting vehicle sounds with a microphone, detecting vehicle vibrations with an accelerometer, detecting accelerations or velocities indicative of a vehicle with an accelerometer). Then, in response to determining that the remote computing device 76 is located in a vehicle, the alert system determines if the storage system 11 is within a predetermined distance (e.g., within 20 feet) of the remote computing device 76. If the storage system is not also within the predetermined distance, the remote computing device 76 can emit an alert.

In some embodiments, in response to determining that the remote computing device 76 is located in a vehicle, the alert system determines if the storage system 11 is also located within a vehicle (e.g., based on detecting vehicle sounds with a microphone, detecting vehicle vibrations with an accelerometer, detecting accelerations or velocities indicative of a vehicle with an accelerometer). If the storage system is not also within a vehicle, the remote computing device 76 can emit an alert.

As mentioned above, the remote computing device 76 can be communicatively coupled with the storage system 11. In several embodiments, the remote computing device 76 includes application software that enables a user to select to option (e.g., touching a button on a touch screen). In response to selecting the option, the storage system 11 can emit a sound from the speaker 24 and/or emit a light to help the user find the storage system 11.

Some embodiments use iBeacon, which is a protocol standardized by Apple Inc. iBeacon can enable finding the location of a storage system and/or remote computing device indoors. Bluetooth low energy (LE) tracking devices can be attached to storage systems to enable the storage systems to broadcast their information to nearby remote computing devices.

Several embodiments use Radio-frequency identification (RFID), which is the wireless use of electromagnetic fields to transfer data. RFID can be used to identify and track tags attached to storage systems.

Some embodiments use Global Positioning Systems (GPS) to track storage systems. GPS is typically well-suited for outdoor tracking.

Manufacturers, physicians, and other entities often provide "instructions for use" with products. For example, a user might buy a storage system that has a first instruction to return the storage system to a room temperature or an indoor environment within 24 hours of entering a warmer or colder environment. This is a simplified way for a manufacturer to communicate thermal performance data to a user. In some cases, the instructions can be based on the temperature of the second, third, or outdoor environment. For example, a zero degree Fahrenheit environment might require returning the storage system to a room temperature or to an indoor environment within 12 hours while a 50 degree Fahrenheit environment might only require returning the storage system to a room temperature or to an indoor environment within 48 hours. These return instructions can be at least 4 hours and/or less than 48 hours; at least 6 hours and/or less than 24 hours; and/or at least 2 hours and/or less than 12 hours. Failing to comply with the return instructions could damage the medicine that is stored in the storage system.

Several embodiments include moving the storage system to a second environment that is cooler than the first environment, and then moving the storage system to a warmer environment, relative to the second environment, in response to a first instruction, wherein the first instruction is a first recommended maximum time that the storage system can be in the second environment that is cooler before being moved to the warmer environment.

Some embodiments include moving the storage system to a third environment that is warmer than the first environment, and then moving the storage system to a cooler environment, relative to the third environment, in response to a second instruction, wherein the second instruction is a second recommended maximum time that the storage system can be in the third environment that is warmer before being moved to the cooler environment.

Relying on time is not the only way for users to know when they need to move their storage device out of a hot or cold environment (e.g., an outdoor environment) and back into a room temperature or indoor environment. Some embodiments include indications that notify users to move the storage system out of a hot or cold environment (e.g., an outdoor environment) and back into a room temperature or indoor environment. For example, some embodiments include moving the storage system to a second environment (e.g., an outdoor environment) that is cooler than the first environment, and then moving the storage system to a warmer environment, relative to the second environment, in response to a first indication provided by at least one of the storage system and a remote computing device. The first indication can be at least one of a sound, a light, a temperature reading, an indicator on a mechanical display, and information on an electronic display. The warmer environment can be a room temperature environment and/or an indoor environment. Several embodiments include moving the storage system to a third environment (e.g., an outdoor environment) that is warmer than the first environment, and then moving the storage system to a cooler environment, relative to the third environment, in response to a second indication provided by at least one of the storage system and the remote computing device. The second indication can also be at least one of a sound, a light, a temperature reading, an indicator on a mechanical display, and information on an electronic display.

FIG. 5 illustrates various ways to communicate the first indication and/or the second indication. For example, the sound can be emitted by the speaker 24 of the storage system and/or by a speaker 24 of the computer 76. The computer 76 can be the remote computing device, and can have an electronic display 62*c* to show warnings and messages regarding the storage system. The storage system can communicate wirelessly with the computer 76. Example remote computing devices include smartphones, computer tablets, laptop computers, and desktop computers. The temperature display 62*b* can be an electronic display that shows information (e.g., a warning message) or emits a notification light (e.g., a flashing red light) when the storage system needs to be returned to room temperature. Of course, the temperature display 62*b* can also show a temperature reading. Once the temperature reading is low or high enough, the user can know it is time to return the storage system to room temperature. In some embodiments, the temperature display 62*b* of the storage system is a mechanical display (e.g., the temperature dial can be the indicator).

The many features described in the context of FIG. 5, including but not limited to the electronic features and the computer 76, can be combined with any of the features described in the context of FIGS. 1-4 and FIGS. 6-37. To reduce redundancy and to increase the clarity of other features in other figures, the features described in the context of FIG. 5 are not repeated for each figure. The lid 18 shown in FIG. 5 can be used with any of the storage systems described herein to combine many electrical elements with many types of storage systems.

Some methods of storing a medicine include obtaining a storage system comprising a first chamber configured to hold the medicine; a phase change system having a first phase change material and a second phase change material, wherein the first phase change material has a first melting temperature greater than 40 degrees Fahrenheit and less than 74 degrees Fahrenheit, and the second phase change material has a second melting temperature greater than 74 degrees Fahrenheit and less than 100 degrees Fahrenheit; and an outer wall system that wraps at least partially around the first chamber and the phase change system. Embodiments can include placing the medicine in the first chamber.

Several embodiments include regulating a temperature of the medicine by utilizing the first phase change material and the second phase change material to protect the medicine from a first external temperature less than a minimum recommended storage temperature and from a second external temperature greater than a maximum recommended storage temperature.

Some methods include maintaining the first chamber in a closed state with the medicine inside the first chamber until an allergic reaction, and then opening the first chamber to retrieve the medicine in response to the allergic reaction (e.g., when the external environment is above the maximum recommended storage temperature or below the minimum recommended storage temperature).

In several embodiments, the medicine comprises at least one of epinephrine, adrenalines, antihistamines, and steroids located within an injection device. Embodiments can include visually inspecting the medicine to determine whether the storage system adequately preserved the medicine (e.g., after removing the medicine from the storage system). This visual inspection can be in response to removing the medicine from the storage system. Some embodiments include treating the allergic reaction with the medicine in response to a determination based on the visual inspection. The determination can be an appearance of the medicine after the medicine has been stored in the storage system and/or removed from the storage system.

Several embodiments include closing the medicine within the first chamber to prepare the storage system for at least one of a first outdoor environment having a first temperature less than a minimum recommended storage temperature and a second outdoor environment having a second temperature greater than a maximum recommended storage temperature.

Some embodiments include closing the medicine within the first chamber to prepare the storage system to protect the medicine from an outdoor environment. Several embodiments include closing the medicine within the first chamber to prepare the storage system to protect the medicine from a first external temperature less than a minimum recommended storage temperature and from a second external temperature greater than a maximum recommended storage temperature by utilizing phase changes to regulate a temperature of the medicine rather than by regulating the temperature using electricity (e.g., via refrigeration electrical systems).

Some embodiments include placing the medicine in the first chamber while located indoors and prior to going outdoors to prepare the storage system for the outdoors. Several embodiments include placing the medicine in the first chamber while located indoors and closing the first chamber from an external environment prior to going outdoors to prepare the storage system for the outdoors.

Several embodiments include maintaining the first chamber in a closed state (e.g., with the lid on the base portion of the storage system) until an allergic reaction, and then opening the first chamber to retrieve the medicine in response to the allergic reaction. Some methods include opening the first chamber to retrieve the medicine in response to the allergic reaction in defiance of an instruction to maintain the first chamber in the closed state until entering an indoor environment.

Some embodiments comprise maintaining the storage system in a room temperature environment until moving the storage system to a hotter or colder environment, and then returning the storage system to the room temperature environment within a predetermined time based at least in part on thermal properties of the storage system. The predetermined time can be at least one hour and/or less than 72 hours.

Several embodiments include maintaining the storage system in a room temperature environment until moving the storage system to an outdoor environment, and then returning the storage system to the room temperature environment within a predetermined time based at least in part on thermal properties of the storage system.

The phase change system can be located inside a vacuum flask. Some embodiments comprise placing the medicine within the vacuum flask and then, in response to an allergic reaction, removing the medicine from the vacuum flask. The medicine can comprise at least one of epinephrine, adrenalines, antihistamines, and steroids located within an injection device. Methods can include treating the allergic reaction with the medicine.

The phase change system can be located inside an insulated bag. Several embodiments include placing the medicine within the insulated bag and then, in response to an allergic reaction, removing the medicine from the insulated bag.

Several embodiments include placing the medicine in the phase change system to protect the medicine from a first external temperature less than a minimum recommended storage temperature and from a second external temperature greater than a maximum recommended storage temperature by utilizing phase changes to regulate a temperature of the medicine rather than by regulating the temperature using electricity.

Some embodiments include maintaining the first chamber in an open state (e.g., with the lid uncoupled from the base portion such that the lid does not shield the medicine's chamber from an external environment) with the medicine inside the first chamber while located indoors and/or in a room temperature environment; and then closing the first chamber in response to going outdoors, in preparation to go outdoors, in preparation to leave the room temperature environment, and/or in preparation to entering a second environment that is hotter or colder than the room temperature environment.

Several embodiments include closing the medicine within the first chamber to prepare the storage system for exiting a room temperature environment and/or opening the first chamber once inside a room temperature environment (e.g., in response to entering a room temperature environment).

Some embodiments include placing the medicine in the phase change system to protect the medicine from a first external temperature less than a room temperature and from a second external temperature greater than the room temperature by utilizing phase changes to regulate a temperature of the medicine. Several embodiments include regulating a temperature of the medicine by utilizing the first phase change material and the second phase change material to protect the medicine from a first external temperature less than a room temperature and from a second external temperature greater than the room temperature.

Many embodiments are described herein to communicate a vast number of features and methods. Describing all of the features and methods in every embodiment would lead to unnecessary redundancy. Each of the features and methods described herein can be included in each of the embodiments described herein. Thus, elements of one embodiment can be combined with elements of other embodiments.

Many embodiments described herein greatly benefit people by enabling them to take their temperature-sensitive medicines outdoors (even in hot or cold weather). Rather than risk being without their medicine (by leaving their medicine behind when going outdoors), the specially constructed storage systems described herein can protect medicines from damage due to hot and cold weather without requiring the bulky structures or expensive components of traditional refrigerators.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

We claim:

1. A storage system comprising:
   a phase change system;
   a first container configured to hold at least a portion of the phase change system; and
   a first chamber located within the first container and configured to hold a medicine,
   wherein the phase change system comprises a first phase change material and a second phase change material, wherein the first phase change material has a first melting temperature greater than 40 degrees Fahrenheit and less than 74 degrees Fahrenheit, and the second phase change material has a second melting temperature greater than 74 degrees Fahrenheit and less than 100 degrees Fahrenheit.

2. The storage system of claim 1, wherein the phase change system is configured to protect the medicine from a first external temperature less than a minimum recommended storage temperature and from a second external temperature greater than a maximum recommended storage temperature by utilizing phase changes to regulate a temperature of the medicine.

3. The storage system of claim 1, wherein an injection device having epinephrine is located in the first chamber.

4. The storage system of claim 3, wherein the injection device comprises a needle configurable to inject the epinephrine into a person.

5. The storage system of claim 1, wherein an injection device having a needle is located in the first chamber such that the storage system shields the injection device from an external environment.

6. The storage system of claim 1, wherein the first container comprises a vacuum chamber configured to thermally insulate the medicine from an external environment.

7. The storage system of claim 6, wherein at least a majority of the first chamber is located radially inward from the vacuum chamber.

8. The storage system of claim 1, wherein the first container comprises a compliant bag having a closeable opening coupled to the first chamber such that the closeable opening is configurable to provide access to the medicine, and wherein the phase change system is located inside of the compliant bag such that insulation of the compliant bag thermally insulates the phase change system from an external environment.

9. The storage system of claim 8, wherein at least a majority of the phase change system is located between a first portion of the insulation and a second portion of the insulation.

10. The storage system of claim 9, wherein at least a majority of the first chamber is located between the first portion and the second portion.

11. The storage system of claim 1, further comprising a second container holding the first phase change material and a third container holding the second phase change material, wherein the second container and the third container are interchangeable within the first container such that the storage system is alternatively configurable to protect the medicine from a first environment below 74 degrees Fahrenheit using the first phase change material and from a second environment above 74 degrees Fahrenheit using the second phase change material.

12. The storage system of claim 11, wherein the first chamber is located in the second container and a second chamber configurable to hold the medicine is located in the third container.

13. The storage system of claim 12, wherein at least one of the first chamber and the second chamber is oriented such that a lid coupled to the first container is removable to provide access to the medicine.

14. The storage system of claim 11, wherein the first container comprises a vacuum chamber configured to thermally insulate the medicine from an external environment.

15. The storage system of claim 11, wherein the first container comprises a compliant bag having insulation configured to thermally insulate the medicine from an external environment.

16. A storage system comprising:
a first container having a first chamber configured to hold a first medicine, wherein the first container comprises a first phase change material having a first melting temperature greater than 40 degrees Fahrenheit and less than 74 degrees Fahrenheit;
a second container having a second chamber configured to hold a second medicine, wherein the second container comprises a second phase change material having a second melting temperature greater than 74 degrees Fahrenheit and less than 100 degrees Fahrenheit; and
a third container, wherein the first container and the second container are located inside the third container.

17. The storage system of claim 16, wherein the first container comprises a vacuum chamber configured to thermally insulate the first medicine from an external environment.

18. The storage system of claim 16, wherein the second container comprises a compliant bag having insulation configured to thermally insulate the first medicine from an external environment.

19. A method of storing a medicine, the method comprising:
obtaining a storage system comprising a phase change system, a first container configured to hold at least a portion of the phase change system, and a first chamber located within the first container, wherein the first chamber is configured to hold a medicine, and wherein the phase change system comprises a first phase change material and a second phase change material, the first phase change material having a first melting temperature greater than 40 degrees Fahrenheit and less than 74 degrees Fahrenheit, and the second phase change material having a second melting temperature greater than 74 degrees Fahrenheit and less than 100 degrees Fahrenheit;

placing the medicine in the first chamber; and storing the storage system in a first environment such that the first phase change material is liquid and the second phase change material is solid.

* * * * *